(12) United States Patent
DiCarlo et al.

(10) Patent No.: US 7,727,555 B2
(45) Date of Patent: Jun. 1, 2010

(54) PARTICLES

(75) Inventors: Paul DiCarlo, Middleboro, MA (US); Janel Lanphere, Pawtucket, RI (US); Thomas V. Casey, II, Grafton, MA (US); Marcia Buiser, Watertown, MA (US); Erin McKenna, Boston, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 11/111,511

(22) Filed: Apr. 21, 2005

(65) Prior Publication Data

US 2006/0199010 A1 Sep. 7, 2006

Related U.S. Application Data

(63) Continuation-in-part of application No. 11/070,967, filed on Mar. 2, 2005.

(51) Int. Cl.
*A61K 9/16* (2006.01)
*A61K 9/32* (2006.01)

(52) U.S. Cl. ...................... 424/489; 424/501

(58) Field of Classification Search .... 428/402–402.24; 427/213.3–213; 264/4–4.7; 347/54, 75; 239/4, 102.1
See application file for complete search history.

(56) References Cited

U.S. PATENT DOCUMENTS

| | | | |
|---|---|---|---|
| 2,275,154 A | 3/1942 | Merrill et al. | |
| 2,609,347 A | 9/1952 | Wilson | |
| 3,252,623 A * | 5/1966 | Corbin et al. | 222/59 |
| 3,663,470 A | 5/1972 | Nishimura et al. | |
| 3,737,398 A | 6/1973 | Yamaguchi | |
| 3,907,429 A * | 9/1975 | Kuhn et al. | 356/28 |
| 3,957,933 A | 5/1976 | Egli et al. | |
| 4,025,686 A | 5/1977 | Zion | |
| 4,034,759 A | 7/1977 | Haerr | |
| 4,055,377 A | 10/1977 | Erickson et al. | |
| 4,076,640 A | 2/1978 | Forgensi et al. | |
| 4,094,848 A | 6/1978 | Naito | |
| 4,096,230 A | 6/1978 | Haerr | |
| 4,098,728 A | 7/1978 | Rosenblatt | |
| 4,110,529 A | 8/1978 | Stoy | |
| 4,159,719 A | 7/1979 | Haerr | |
| 4,191,672 A | 3/1980 | Salome et al. | |
| 4,198,318 A | 4/1980 | Stowell et al. | |
| 4,243,794 A | 1/1981 | White et al. | |
| 4,246,208 A | 1/1981 | Dundas | |
| 4,266,030 A | 5/1981 | Tschang et al. | |
| 4,268,495 A | 5/1981 | Muxfeldt et al. | |
| 4,271,281 A | 6/1981 | Kelley et al. | |
| 4,402,319 A | 9/1983 | Handa et al. | |
| 4,413,070 A | 11/1983 | Rembaum | |
| 4,427,794 A | 1/1984 | Lange et al. | |
| 4,428,869 A | 1/1984 | Munteanu et al. | |
| 4,429,062 A | 1/1984 | Pasztor et al. | |
| 4,442,843 A | 4/1984 | Rasor et al. | |
| 4,444,961 A | 4/1984 | Timm | |
| 4,452,773 A | 6/1984 | Molday | |
| 4,456,693 A | 6/1984 | Welsh | |
| 4,459,145 A | 7/1984 | Elsholz | |
| 4,472,552 A | 9/1984 | Blouin | |
| 4,477,255 A | 10/1984 | Pasztor et al. | |
| 4,492,720 A | 1/1985 | Moiser | |
| 4,515,906 A | 5/1985 | Friesen et al. | |
| 4,522,953 A | 6/1985 | Barby et al. | |
| 4,542,178 A | 9/1985 | Zimmermann et al. | |
| 4,551,132 A | 11/1985 | Pasztor et al. | |
| 4,551,436 A | 11/1985 | Johnson et al. | |
| 4,573,967 A | 3/1986 | Hargrove et al. | |
| 4,622,362 A | 11/1986 | Rembaum | |
| 4,623,706 A | 11/1986 | Timm et al. | |
| 4,629,464 A | 12/1986 | Takata et al. | |
| 4,640,807 A | 2/1987 | Afghan et al. | |
| 4,657,756 A | 4/1987 | Rasor et al. | |
| 4,661,137 A | 4/1987 | Garnier et al. | |
| 4,663,358 A | 5/1987 | Hyon et al. | |
| 4,671,954 A | 6/1987 | Goldberg et al. | |
| 4,674,480 A | 6/1987 | Lemelson | |
| 4,675,113 A | 6/1987 | Graves et al. | |
| 4,678,710 A | 7/1987 | Sakimoto et al. | |
| 4,678,814 A | 7/1987 | Rembaum | |

(Continued)

FOREIGN PATENT DOCUMENTS

AU       A-76186/98       10/1998

(Continued)

OTHER PUBLICATIONS

Gibbs, Marylu B., United States Statutory Invention Registration H915, May 7, 1991.

(Continued)

*Primary Examiner*—James Seidleck
*Assistant Examiner*—Saira Haider
(74) *Attorney, Agent, or Firm*—Fish & Richardson, P.C.

(57) ABSTRACT

Particles and related methods are disclosed. In some embodiments, a method of making particles can include forming a stream of a mixture including first and second materials, exposing the stream to a vibration, and treating the stream to form particles. The vibration can have, for example, a sinusoidal, triangular, and/or sawtooth waveform.

26 Claims, 33 Drawing Sheets

U.S. PATENT DOCUMENTS

| | | | |
|---|---|---|---|
| 4,680,320 A | 7/1987 | Uku et al. | |
| 4,681,119 A | 7/1987 | Rasor et al. | |
| 4,695,466 A | 9/1987 | Morishita et al. | |
| 4,713,076 A | 12/1987 | Draenert | |
| 4,742,086 A | 5/1988 | Masamizu et al. | |
| 4,743,507 A | 5/1988 | Franses et al. | |
| 4,752,459 A * | 6/1988 | Pepper | 423/338 |
| 4,772,635 A | 9/1988 | Mitschker et al. | |
| 4,782,097 A | 11/1988 | Jain et al. | |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | |
| 4,804,366 A | 2/1989 | Zdeb et al. | |
| 4,819,637 A | 4/1989 | Dormandy, Jr. et al. | |
| 4,822,535 A | 4/1989 | Ekman et al. | |
| 4,833,237 A | 5/1989 | Kawamura et al. | |
| 4,850,978 A | 7/1989 | Dudar et al. | |
| 4,859,711 A | 8/1989 | Jain et al. | |
| 4,863,972 A | 9/1989 | Itagaki et al. | |
| 4,897,255 A | 1/1990 | Fritzberg et al. | |
| 4,929,400 A | 5/1990 | Rembaum et al. | |
| 4,933,372 A | 6/1990 | Feibush et al. | |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | |
| 4,999,188 A | 3/1991 | Sloldovnik et al. | |
| 5,007,940 A | 4/1991 | Berg | |
| 5,011,677 A | 4/1991 | Day et al. | |
| 5,015,423 A | 5/1991 | Eguchi et al. | |
| 5,032,117 A | 7/1991 | Motta | |
| 5,034,324 A | 7/1991 | Shinozaki et al. | |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | |
| 5,114,421 A | 5/1992 | Polak | |
| 5,116,387 A | 5/1992 | Berg | |
| 5,120,349 A | 6/1992 | Stewart et al. | |
| 5,125,892 A | 6/1992 | Drudik | |
| 5,147,631 A | 9/1992 | Glajch et al. | |
| 5,147,937 A | 9/1992 | Frazza et al. | |
| 5,149,543 A | 9/1992 | Cohen et al. | |
| 5,158,573 A | 10/1992 | Berg | |
| 5,165,580 A * | 11/1992 | Rosenthal | 222/251 |
| 5,171,214 A | 12/1992 | Kolber et al. | |
| 5,171,217 A | 12/1992 | March et al. | |
| 5,181,921 A | 1/1993 | Makita et al. | |
| 5,190,760 A | 3/1993 | Baker | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | |
| 5,253,991 A | 10/1993 | Yokota et al. | |
| 5,260,002 A | 11/1993 | Wang | |
| 5,262,176 A | 11/1993 | Palmacci et al. | |
| 5,263,992 A | 11/1993 | Guire | |
| 5,278,626 A * | 1/1994 | Poole et al. | 356/36 |
| 5,288,763 A | 2/1994 | Li et al. | |
| 5,292,814 A | 3/1994 | Bayer et al. | |
| 5,302,369 A | 4/1994 | Day et al. | |
| 5,314,974 A | 5/1994 | Ito et al. | |
| 5,316,774 A | 5/1994 | Eury et al. | |
| RE34,640 E | 6/1994 | Kennedy et al. | |
| 5,320,639 A | 6/1994 | Rudnick | |
| 5,328,936 A | 7/1994 | Leifholtz et al. | |
| 5,336,263 A | 8/1994 | Ersek et al. | |
| 5,344,452 A | 9/1994 | Lemperle | |
| 5,344,867 A | 9/1994 | Morgan et al. | |
| 5,354,290 A | 10/1994 | Gross | |
| 5,369,133 A | 11/1994 | Ihm et al. | |
| 5,369,163 A | 11/1994 | Chiou et al. | |
| 5,382,260 A | 1/1995 | Dormandy, Jr. et al. | |
| 5,384,124 A | 1/1995 | Courteille et al. | |
| 5,397,303 A | 3/1995 | Sancoff et al. | |
| 5,398,851 A | 3/1995 | Sancoff et al. | |
| 5,403,870 A | 4/1995 | Gross | |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,456,693 A | 10/1995 | Conston et al. | |
| 5,468,801 A | 11/1995 | Antonelli et al. | |
| 5,469,854 A | 11/1995 | Unger et al. | |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | |
| 5,494,940 A | 2/1996 | Unger et al. | |
| 5,512,604 A | 4/1996 | Demopolis | |
| 5,514,090 A | 5/1996 | Kriesel et al. | |
| 5,525,334 A | 6/1996 | Ito et al. | |
| 5,534,589 A | 7/1996 | Hager et al. | |
| 5,541,031 A | 7/1996 | Yamashita et al. | |
| 5,542,935 A | 8/1996 | Unger et al. | |
| 5,553,741 A | 9/1996 | Sancoff et al. | |
| 5,556,391 A | 9/1996 | Cercone et al. | |
| 5,556,610 A | 9/1996 | Yan et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,567,415 A | 10/1996 | Porter | |
| 5,569,193 A | 10/1996 | Hofstetter et al. | |
| 5,569,449 A | 10/1996 | Klaveness et al. | |
| 5,569,468 A | 10/1996 | Modi | |
| 5,571,182 A | 11/1996 | Ersek et al. | |
| 5,580,575 A | 12/1996 | Unger et al. | |
| 5,583,162 A | 12/1996 | Li et al. | |
| 5,585,112 A | 12/1996 | Unger et al. | |
| 5,595,821 A | 1/1997 | Hager et al. | |
| 5,622,657 A | 4/1997 | Takada et al. | |
| 5,624,685 A | 4/1997 | Takahashi et al. | |
| 5,635,215 A | 6/1997 | Boschetti et al. | |
| 5,637,087 A | 6/1997 | O'Neil et al. | |
| 5,639,710 A | 6/1997 | Lo et al. | |
| 5,648,095 A | 7/1997 | Illum et al. | |
| 5,648,100 A | 7/1997 | Boschetti et al. | |
| 5,650,116 A | 7/1997 | Thompson | |
| 5,651,990 A | 7/1997 | Takada et al. | |
| 5,653,922 A | 8/1997 | Li et al. | |
| 5,657,756 A | 8/1997 | Vrba | |
| 5,681,576 A | 10/1997 | Henry | |
| 5,695,480 A | 12/1997 | Evans et al. | |
| 5,695,740 A | 12/1997 | Porter | |
| 5,698,271 A | 12/1997 | Liberti et al. | |
| 5,701,899 A | 12/1997 | Porter | |
| 5,715,824 A | 2/1998 | Unger et al. | |
| 5,716,981 A | 2/1998 | Hunter et al. | |
| 5,718,884 A | 2/1998 | Klaveness et al. | |
| 5,723,269 A | 3/1998 | Akagi et al. | |
| 5,725,534 A | 3/1998 | Rasmussen | |
| 5,733,925 A | 3/1998 | Kunz et al. | |
| 5,741,331 A | 4/1998 | Pinchuk | |
| 5,746,734 A | 5/1998 | Dormandy, Jr. et al. | |
| 5,752,974 A | 5/1998 | Rhee et al. | |
| 5,756,127 A | 5/1998 | Grisoni et al. | |
| 5,760,097 A | 6/1998 | Li et al. | |
| 5,766,147 A | 6/1998 | Sancoff et al. | |
| 5,770,222 A | 6/1998 | Unger et al. | |
| 5,779,668 A | 7/1998 | Grabenkort | |
| 5,785,642 A | 7/1998 | Wallace et al. | |
| 5,785,682 A | 7/1998 | Grabenkort | |

| | | |
|---|---|---|
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,048,908 A | 4/2000 | Kitagawa |
| 6,051,247 A | 4/2000 | Hench et al. |
| 6,056,721 A | 5/2000 | Shulze |
| 6,056,844 A | 5/2000 | Guiles et al. |
| 6,059,766 A | 5/2000 | Greff |
| 6,063,068 A | 5/2000 | Fowles et al. |
| 6,071,495 A | 6/2000 | Unger et al. |
| 6,071,497 A | 6/2000 | Steiner et al. |
| 6,073,759 A | 6/2000 | Lamborne et al. |
| 6,090,925 A | 7/2000 | Woiszwillo et al. |
| 6,096,344 A | 8/2000 | Liu et al. |
| 6,099,864 A | 8/2000 | Morrison et al. |
| 6,100,306 A | 8/2000 | Li et al. |
| 6,139,963 A | 10/2000 | Fujii et al. |
| 6,149,623 A | 11/2000 | Reynolds |
| 6,160,084 A | 12/2000 | Langer et al. |
| 6,162,377 A | 12/2000 | Ghosh et al. |
| 6,165,193 A | 12/2000 | Greene, Jr. et al. |
| 6,179,817 B1 | 1/2001 | Zhong |
| 6,191,193 B1 | 2/2001 | Lee et al. |
| 6,214,331 B1 | 4/2001 | Vanderhoff et al. |
| 6,214,384 B1 | 4/2001 | Pallado et al. |
| 6,224,630 B1 | 5/2001 | Bao et al. |
| 6,224,794 B1 | 5/2001 | Amsden et al. |
| 6,235,224 B1 | 5/2001 | Mathiowitz et al. |
| 6,238,403 B1 | 5/2001 | Greene, Jr. et al. |
| 6,245,090 B1 | 6/2001 | Gilson et al. |
| 6,251,661 B1 | 6/2001 | Urabe et al. |
| 6,258,338 B1 | 7/2001 | Gray |
| 6,261,585 B1 | 7/2001 | Sefton et al. |
| 6,264,861 B1 | 7/2001 | Tavernier et al. |
| 6,267,154 B1 | 7/2001 | Felicelli et al. |
| 6,268,053 B1 | 7/2001 | Woiszwillo et al. |
| 6,277,392 B1 | 8/2001 | Klein |
| 6,280,457 B1 | 8/2001 | Wallace et al. |
| 6,291,605 B1 | 9/2001 | Freeman et al. |
| 6,296,604 B1 | 10/2001 | Garibaldi et al. |
| 6,296,622 B1 | 10/2001 | Kurz et al. |
| 6,296,632 B1 | 10/2001 | Luscher et al. |
| 6,306,418 B1 | 10/2001 | Bley |
| 6,306,419 B1 | 10/2001 | Vachon et al. |
| 6,306,425 B1 | 10/2001 | Tice et al. |
| 6,306,427 B1 | 10/2001 | Annonier et al. |
| 6,312,407 B1 | 11/2001 | Zadno-Azizi et al. |
| 6,312,942 B1 | 11/2001 | Plüss-Wenzinger et al. |
| 6,315,709 B1 | 11/2001 | Garibaldi et al. |
| 6,335,384 B1 | 1/2002 | Evans et al. |
| 6,344,182 B1 | 2/2002 | Sutton et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,394,965 B1 | 5/2002 | Klein |
| 6,423,332 B1 | 7/2002 | Huxel et al. |
| 6,432,437 B1 | 8/2002 | Hubbard |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,575,896 B2 | 6/2003 | Silverman et al. |
| 6,602,261 B2 | 8/2003 | Greene, Jr. et al. |
| 6,602,524 B2 | 8/2003 | Batich et al. |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,680,046 B1 | 1/2004 | Boschetti |
| 6,699,222 B1 | 3/2004 | Jones et al. |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1* | 5/2002 | Kim et al. .................. 424/489 |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0071134 A1* | 4/2003 | Shekarriz et al. ................ 239/4 |
| 2003/0108614 A1 | 6/2003 | Volkonsky et al. |
| 2003/0183962 A1 | 10/2003 | Buiser et al. |
| 2003/0185895 A1* | 10/2003 | Lanphere et al. ............ 424/493 |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0203985 A1 | 10/2003 | Baldwin et al. |
| 2003/0206864 A1 | 11/2003 | Mangin |
| 2003/0215519 A1 | 11/2003 | Schwarz et al. |
| 2003/0233150 A1 | 12/2003 | Bourne et al. |
| 2004/0076582 A1 | 4/2004 | DiMatteo et al. |
| 2004/0091543 A1 | 5/2004 | Bell et al. |
| 2004/0092883 A1 | 5/2004 | Casey, III et al. |
| 2004/0096662 A1 | 5/2004 | Lanphere et al. |
| 2004/0101564 A1 | 5/2004 | Rioux et al. |
| 2004/0117010 A1 | 6/2004 | Houston et al. |
| 2004/0186377 A1 | 9/2004 | Zhong et al. |
| 2005/0025800 A1 | 2/2005 | Tan |
| 2005/0037047 A1 | 2/2005 | Song |
| 2005/0095428 A1 | 5/2005 | DiCarlo et al. |
| 2005/0129775 A1 | 6/2005 | Lanphere et al. |
| 2005/0171510 A1 | 8/2005 | DiCarlo et al. |

| | | | |
|---|---|---|---|
| 2005/0196449 | A1 | 9/2005 | DiCarlo et al. |
| 2005/0226935 | A1 | 10/2005 | Kamath et al. |
| 2005/0238870 | A1 | 10/2005 | Buiser et al. |
| 2005/0263916 | A1 | 12/2005 | Lanphere et al. |

FOREIGN PATENT DOCUMENTS

| | | |
|---|---|---|
| DE | 3834705 | 4/1990 |
| DE | 94 14 868.6 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/32241 | 6/2000 |
| WO | WO 00/40259 | 7/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 02/062271 | 8/2002 |
| WO | 03/013552 | 2/2003 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | 2004/040972 | 5/2004 |
| WO | WO 2004/073688 | 9/2004 |
| WO | WO 2004/075989 | 9/2004 |
| WO | 2006/093972 | 9/2006 |

OTHER PUBLICATIONS

Huang et al., "Hydrophilic-hydrophobic biodegradable polymers: release characteristics of hydrogen-bonded, ring-containing polymer matrices," Biomaterials, 15(15):1243-1247 (1994).

U.S. Appl. No. 10/927,868, filed Aug. 27, 2004, Richard et al.

U.S. Appl. No. 11/000,741, filed Dec. 1, 2004, Elliott et al.

U.S. Appl. No. 11/070,967, filed Mar. 2, 2005, Anderson et al.

Abbara et al., "Transcervical Expulsion of a Fibroid as a Result of Uterine Artery Embolization for Leiomyomata", *JVIR*, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al., "Polyvinyl Alcohol Foam Particles Sizes and Concentrations Injectable through Microcatheters", *JVIR*, vol. 9, No. 1, pp. 113-118; 1998.

Barton, P. et al., "Embolization of Bone Metastases," *Journal of Vascular and Interventional Radiology*, 7(1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994.

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Concentric Medical, Inc.—Product Information (3 pages), 2002.

Cruise et al., "In Vitro and In Vivo Characterization of a Hydrogel-Based Aneurysm Embolization System," *Society for Biomaterials 28$^{th}$ Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection For Unilateral Vocal Fold Paralysis: Functional Results," *Ann. Otol. Rhinol Laryngol.*, 99(8):598-604 (Aug. 1990).

Horak et al., "Hydrogels in endovascular embolization. I. Spherical particles of poly (2-hydroxyethyl methacrylate) and their medico-biological properties", *Biomaterials*, 7(3):188-192 (May 1986).
Horak et al., "Hydrogels in endovascular embolization. II. Clinical use of spherical particles", *Biomaterials*, 7(6):467-470 (Nov. 1986).
Huang, et al., "Percutaneous endovascular embolization of intracerebral arteriovenous malformations. Experience in 72 cases", *Chin Med J*, vol. 108, No. 6, pp. 413-419, 1995.
"Injectable Tissue Implant Could Repair Ravages of Surgery", Clemson University, Biotech Week, Oct. 22, 2003, p. 117.
Jack, et al., "Radiolabeled polyvinyl alcohol particles: a potential agent to monitor embolization procedures", *Int J Rad Appl Instrum B*, vol. 13, No. 3, pp. 235-243, 1986.
Jiaqi, Y. et al., "A New Embolic Material: Super Absorbent Polymer (SAP) Microsphere and Its Embolic Effects," *Nippon Acta Radiologica*, 56:19-24 (1996).
Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.
Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.
Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).
Kai, et al., "The utility of the microcrystalline cellulose sphere as a particulate embolic agent: an experimental study", *American Journal of Radiology*, vol. 21, No. 6, pp. 1160-1163, 2000.
Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.
Kan, et al., "In vivo microscopy of the liver after injection of lipiodol into the hepatic artery and portal vein in the rat", *Acta Radiologica*, vol. 30, pp. 419-425, 1989.
Kerber, C., "Balloon Catheter with a Calibrated Leak", *Radiology*, vol. 120, pp. 547-550, Sep. 1976.
Kerber et al., "Polyvinyl Alcohol Foam: Prepackaged Emboli for Therapeutic Embolization", *American Journal Roentgenol*, vol. 130, pp. 1193-1194, Jun. 1978.
Kerber, "Flow-Controlled Therapeutic Embolization: A Physiologic and Safe Technique", *AJR*, vol. 134, pp. 557-561, Mar. 1980.
Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).
Kim, et al., "Composite poly(vinyl alcohol) beads for controlled drug delivery", *Pharm Res*, vol. 9. No. 1, pp. 10-16, 1992.
Kim et al., "Hollow Silica Spheres of Controlled Size and Porosity by Sol-Gel Processing," *J. Am. Ceram. Soc.*, 74(8):1987-1992 (Aug. 1991).
Kim et al., "Poly(vinyl alcohol) beads with core-shell structure for drug delivery," *Cosmetic and Pharmaceutical Applications of Polymers*, Plenum Press, New York, pp. 209-214 (1991).
Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).
Kochan, J.P. et al., "Interventional Neuroradiology: Current Practices and Techniques at Temple University Hospital," http://www.temple.edu/radiology/stroke.html, 5 pages.
Krinick et al., "A polymeric drug delivery system for the simultaneous delivery of drugs activatable by enzymes and/or light," *J. Biomater. Sci. Polymer Edn*, 5(4):303-324 (1994).
Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.
Kurata, et al., "Preoperative embolization for meningiomas using PVA particles", *No Shinkei Geka*, vol. 20, No. 4, pp. 367-373, 1992 (Abstract).
Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (Abstract).
Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.
Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.
Labarre et al., "Complement activation by substituted polyacrylamide hydrogels for embolisation and implantation", *Biomaterials*, vol. 23, pp. 2319-2327, 2002.
Lammer, et al., "Transcatheteral embolization with polyvinyl alcohol—technic and experimental studies", *Rontgenblatter*, vol. 36, No. 1, pp. 10-14, 1983 (Abstract).
Latchaw et al., "Polyvinyl Foam Embolization of Vascular and Neoplastic Lesions of the Head, Neck, and Spine", *Radiology*, vol. 131, pp. 669-679, Jun. 1979.
Laurent, "Materials and biomaterials for interventional radiology," *Biomed. & Pharmacother.*, 52:76-88 (1998).
Lemperle et al., "PMMA Microspheres for Intradermal Implantation: Part I. Animal Research," *Annals of Plastic Surgery*, 26(1):56-63 (Jan. 1991).
Lendlein, A. et al., "Biodegradable, Elastic Shape-Memory Polymers for Potential Biomedical Applications", *Science*, vol. 296, pp. 1673-1676, May 31, 2002.
Leung et al., "Determinants of Postembolization Syndrome after Hepatic Chemoembolization", *Journal of Vascular and Interventional Radiology*, vol. 12, No. 3, pp. 320-326, Mar. 2001.
Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.
Levy et al., "Transcatheter Uterine Artery Embolization for the Treatment of Symptomatic Uterine Fibroid Tumors," *Journal of Women's Imaging*, 2(4):168-175 (2000).
Lipman, "Uterine artery embolization for the treatment of symptomatic uterine fibroids: A review," *Applied Radiology*, 29(7):15-20 (Jul. 2000).
Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.
Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.
Markoff, et al., "Uterine arteriovenous malformation successfully embolized with a liquid polymer, isobutyl 2-cyanoacrylate", *Am. J. Obstet. Gynecol.*, 155:659-660 (Sep. 1986).
Markus et al., "Experimental Aspects of High-Intensity Transient Signals in the Detection of Emboli," *J. Clin. Ultrasound.*, 23(2):81-87 (Feb. 1995).
Maruhashi, "Modified Polyvinyl Alcohols I and II," *Polyvinyl Alcohol—Developments*, John Wiley & Sons, Chichester, England, pp. 160-161 and pp. 186-191 (1992).
Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.
Mather, P.T., Research Group Homepage, Basic Goals and Methods, http://www.ims.uconn.edu/~mather, 4 pages.
Matsumaru, et al., "Embolic materials for endovascular treatment of cerebral lesions", *J Biomater Sci Polym Ed*, vol. 8, No. 7, pp. 555-569, 1997.
Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.
Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

"New Advances in RF Sputtering," Aultimut International Inc., http://www.aultimut.com/rf_sput.html, 3 pages (Retrieved from the Internet on Apr. 12, 2005).

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

"Tektronix AFG300 Series Function/Arbitrary Waveform Generator," TestEquity Electronic Test Equipment, 3 pages (Retrieved from the Internet on Apr. 12, 2005).

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (Abstract).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (Abstract).

Vogel, F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

"What is Sputtering?" D2 Inline Solutions, LLC, http://www.d2inlinesolutions.com/sputtering.htm, 3 pages (Retrieved from the Internet on Apr. 12, 2005).

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

* cited by examiner

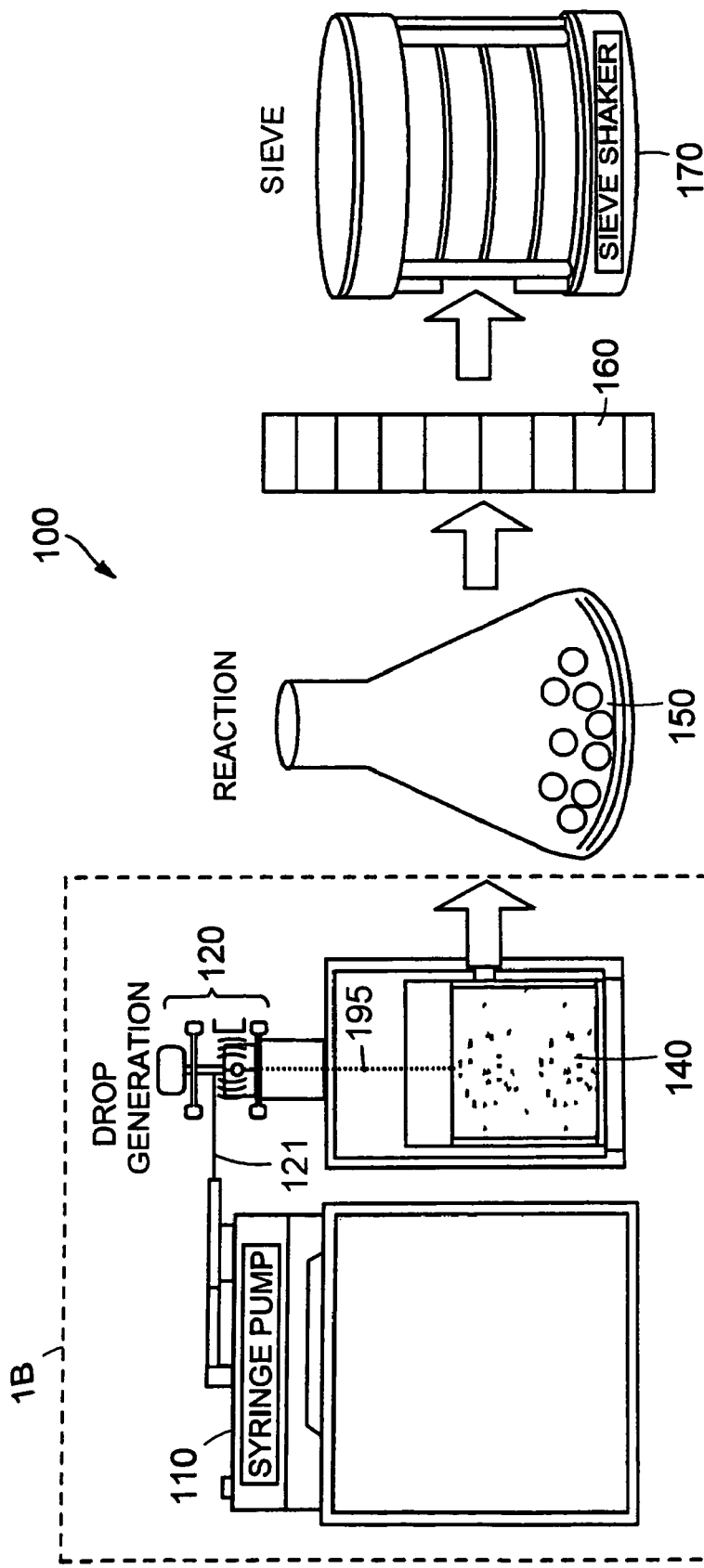

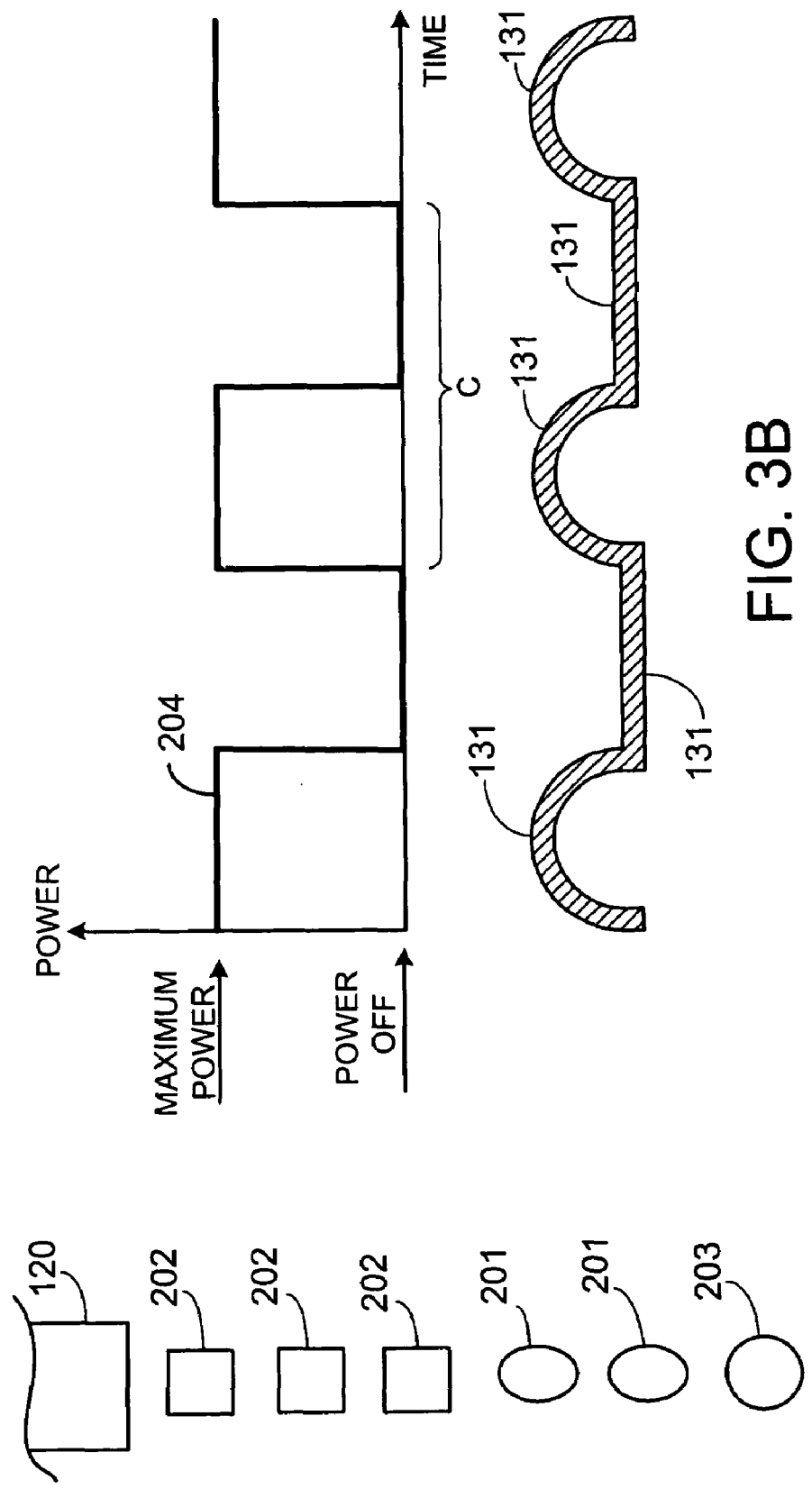

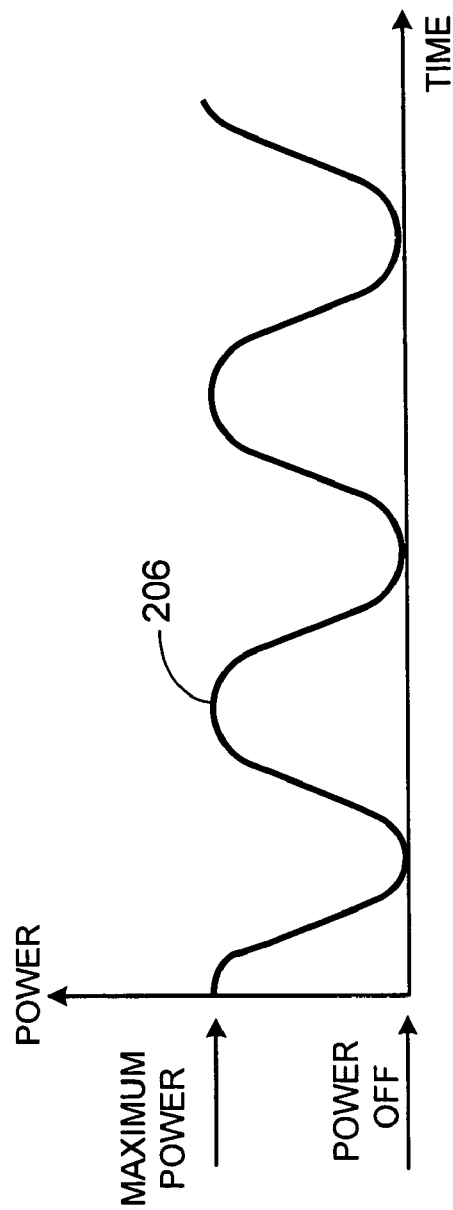
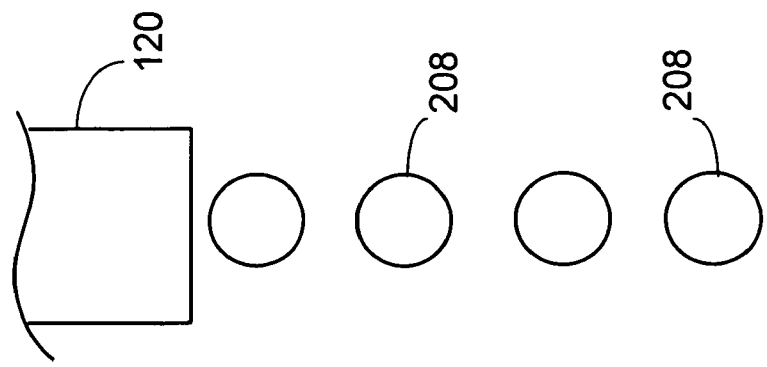
FIG. 3D
FIG. 3C

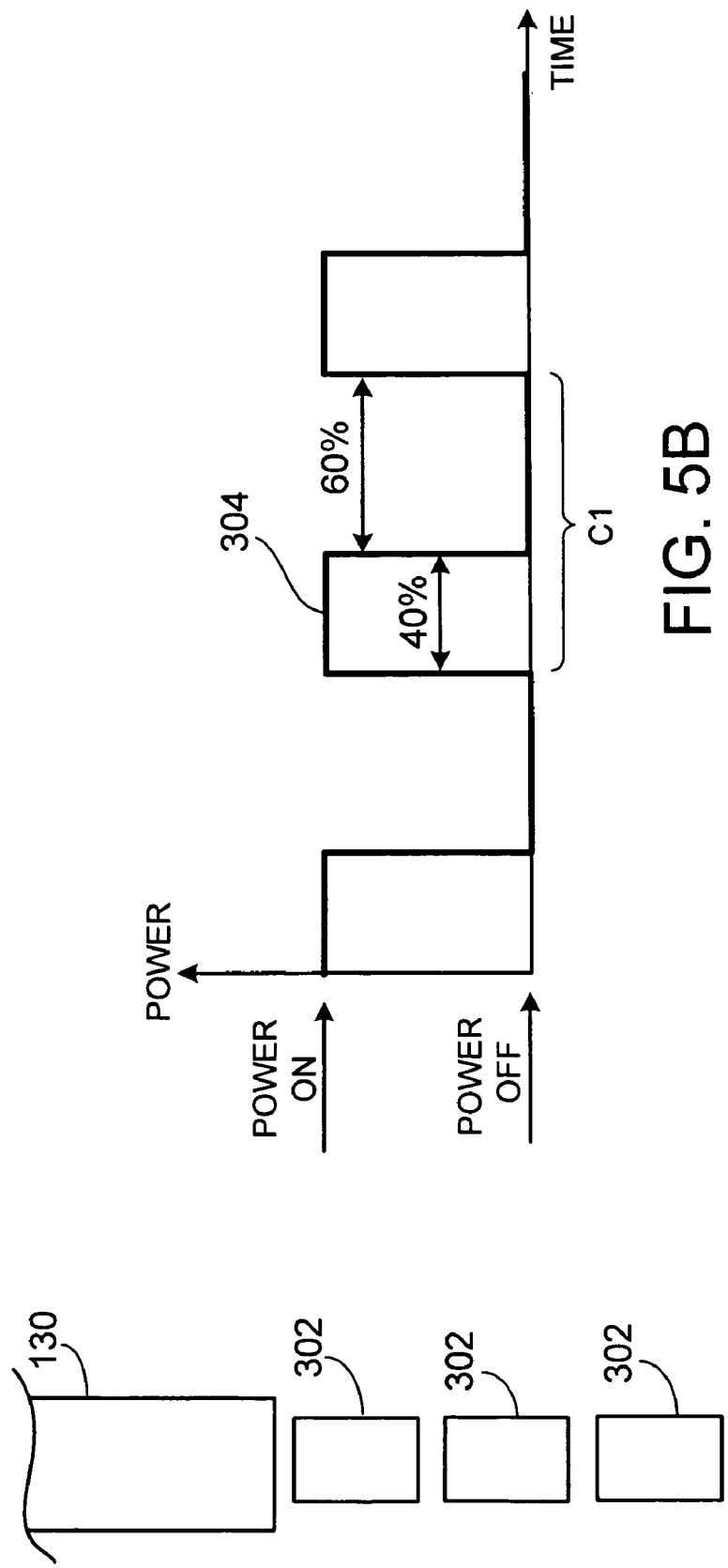

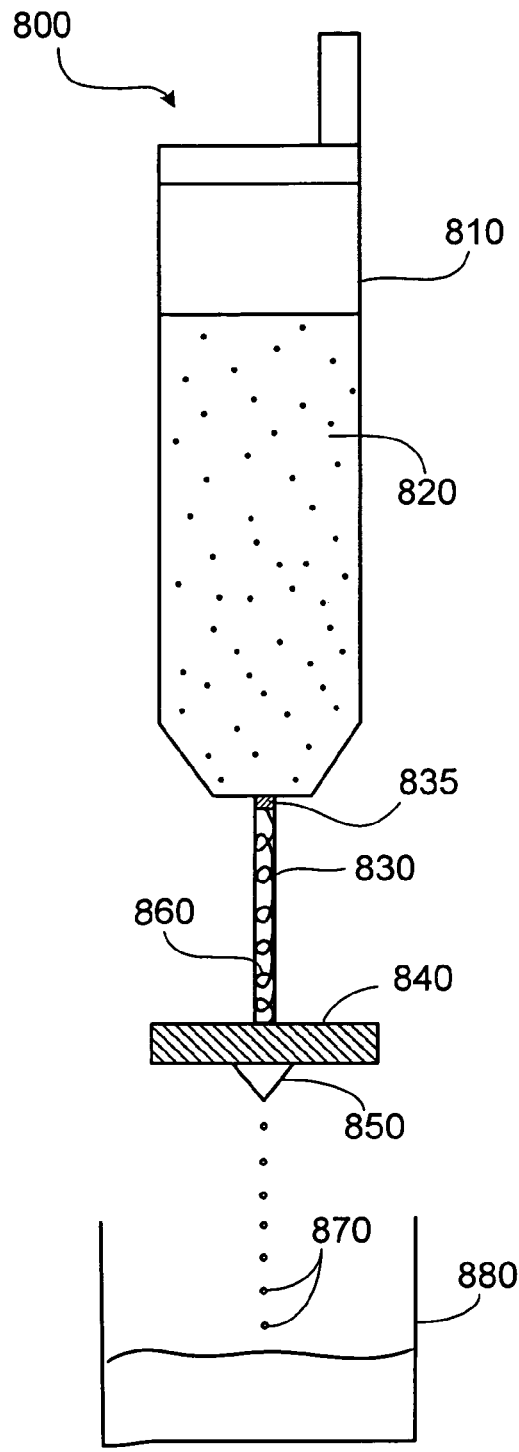
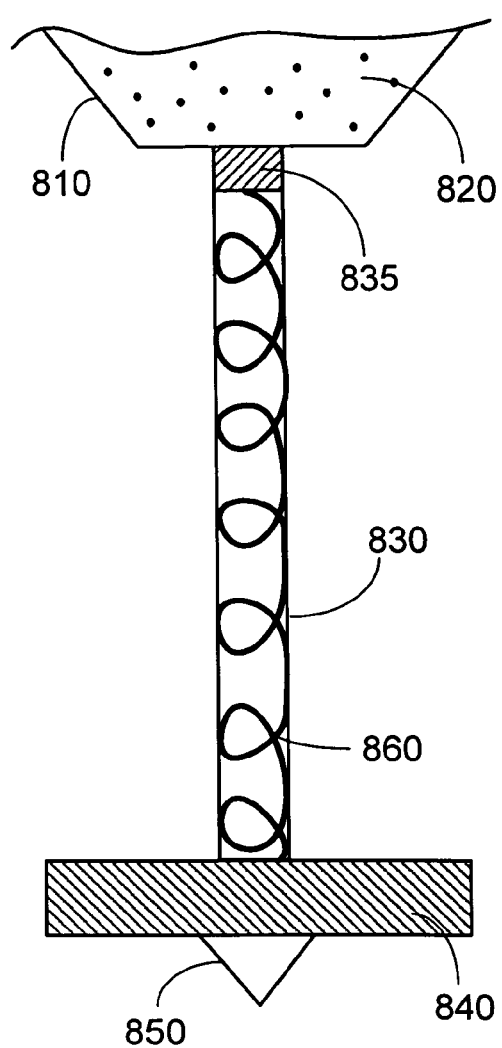
FIG. 14A
FIG. 14B

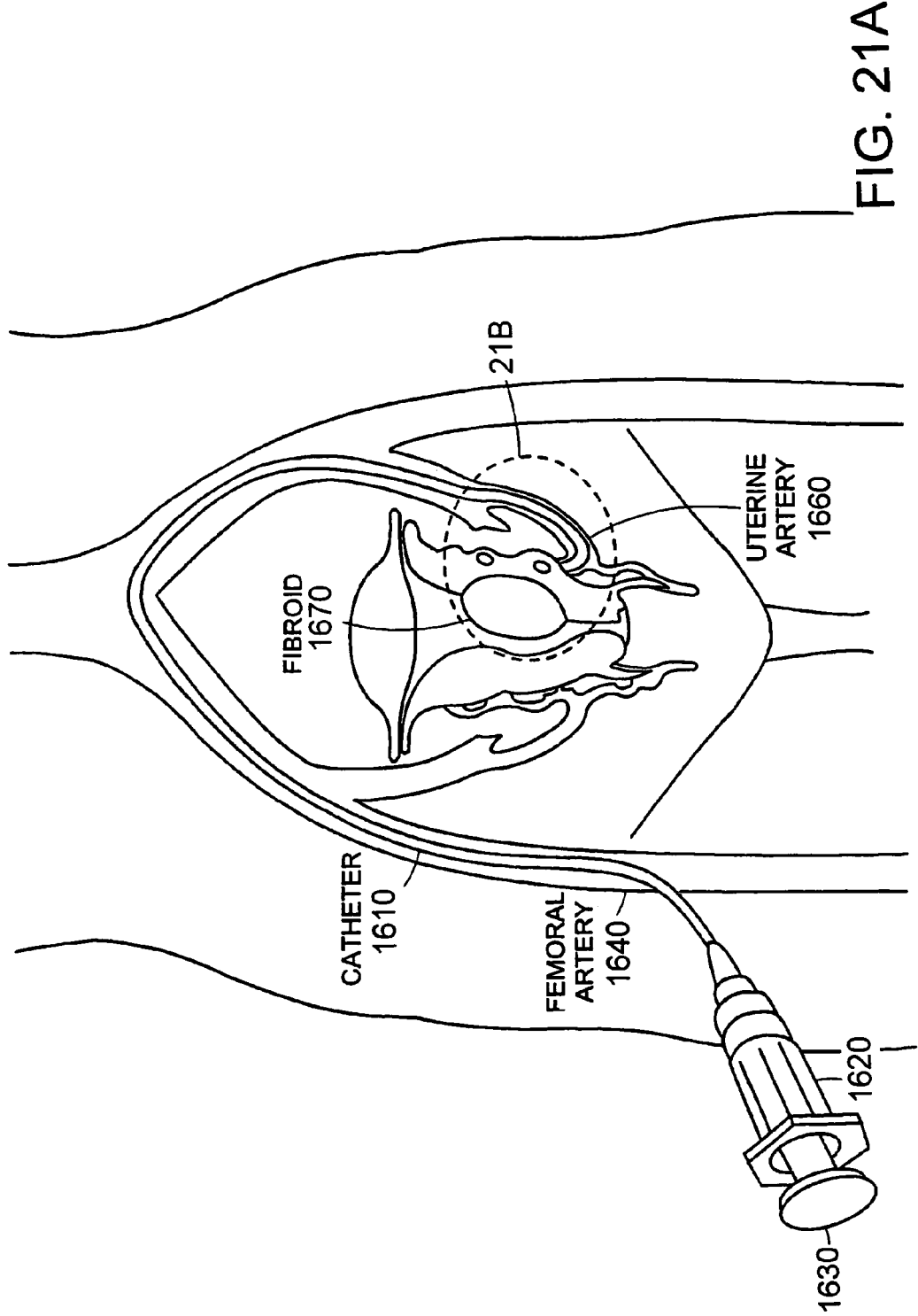

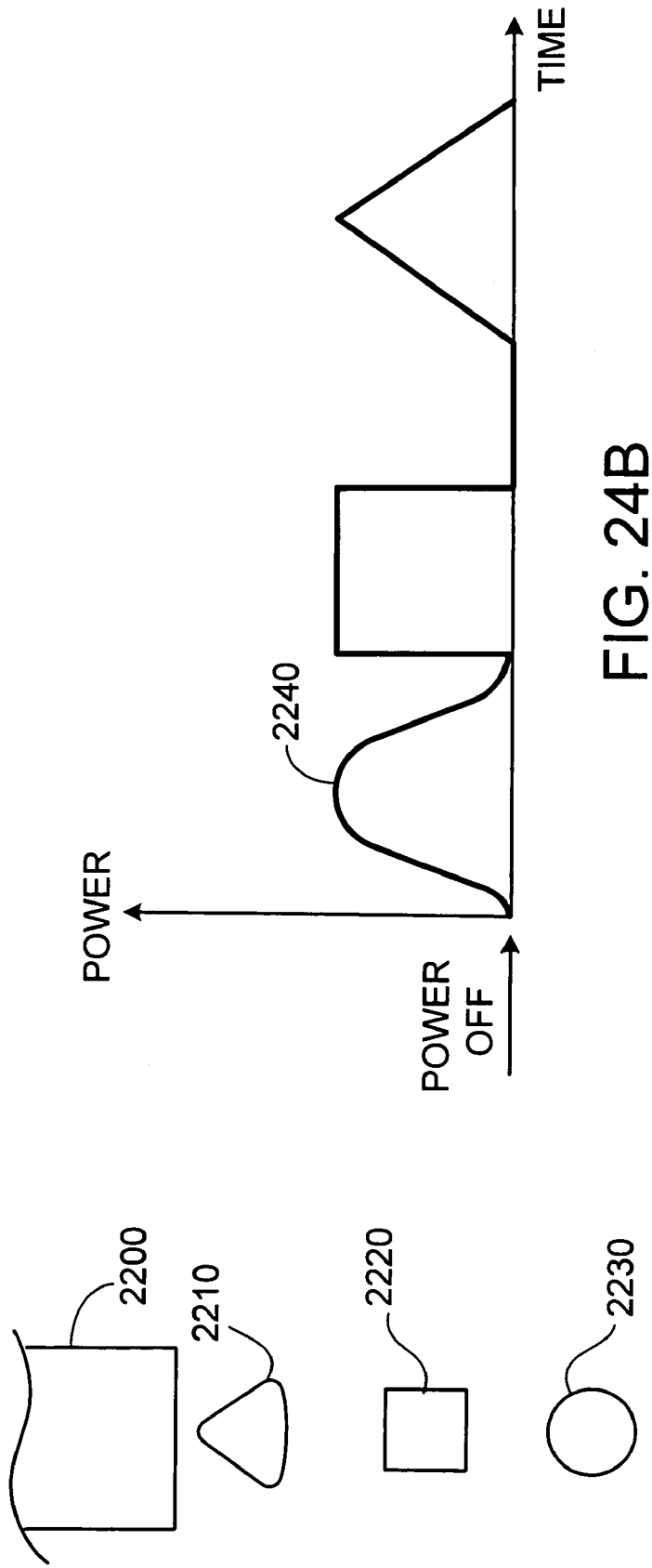

PARTICLES

CROSS-REFERENCE TO RELATED APPLICATIONS

This application is a continuation-in-part of, and claims priority under 35 U.S.C. §120 to, U.S. patent application Ser. No. 11/070,967, filed on Mar. 2, 2005 and entitled "Particles", which is incorporated herein by reference in its entirety.

TECHNICAL FIELD

The invention relates to particles, such as embolic particles, and to related methods.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a method of making particles. The method includes forming a stream of a mixture including first and second materials (e.g., a polymer and a gelling precursor), exposing the stream to a vibration having a non-uniform frequency, and treating the stream to form a plurality of particles including the first material.

In some embodiments, exposing a stream to a vibration having a non-uniform frequency can result in the formation of particles of different sizes and/or shapes. In certain embodiments, particles of different sizes and/or shapes can be used in an embolization procedure and/or a tissue bulking procedure. The different sizes and/or shapes of the particles may enhance the ability of the particles to, for example, fit together to fill a space in the tissue of a subject or to embolize a lumen of a subject.

In another aspect, the invention features a method of making particles. The method includes forming a stream of a mixture including first and second materials, exposing the stream to a vibration having a non-square (e.g., triangular, sinusoidal, sawtooth) waveform, and treating the stream to form particles.

In a further aspect, the invention features a method of making particles. The method includes forming a stream of a mixture including first and second materials, exposing the stream to a vibration having a triangular, sinusoidal, or sawtooth waveform, and treating the stream to form particles.

In an additional aspect, the invention features a method of making particles. The method includes forming a stream of a mixture including first and second materials, exposing the stream to a vibration having a non-rectangular waveform, and treating the stream to form particles.

In certain embodiments, exposing a stream to a non-square or non-rectangular waveform can result in the formation of non-spherical (e.g., conical, cylindrical, diamond-shaped, spheroidal) particles. In some embodiments, non-spherical particles may fit together to fill a space in the tissue of a subject or to embolize a lumen of a subject.

In a further aspect, the invention features a method that includes forming a stream of drops at a first frequency, observing the stream of drops at a second frequency, and treating the stream of drops to form particles.

In some embodiments, the first frequency can be different from the second frequency. In certain embodiments, the first frequency can be the same as the second frequency.

In some embodiments, using one frequency to form a stream of drops and another frequency to observe (e.g., view) the stream of drops can enhance the ability of an operator and/or observer to observe drop formation while still using an appropriate frequency for drop formation.

In another aspect, the invention features a drop generator including a nozzle, a membrane, and a frequency generator that has at least two channels. The nozzle and the membrane are configured to form drops with a diameter of at most about 3,000 microns.

In certain embodiments, a frequency generator that includes at least two channels can be used to form a stream of drops at one frequency and to observe the stream of drops at another frequency. In some embodiments, a frequency generator with at least two channels can be used to generate at least two drop generator membrane vibration waveforms that can combine to form one hybrid waveform. Thus, the frequency generator may provide an operator with enhanced flexibility in operating a drop generator. For example, in certain embodiments, the operator may use the frequency generator to form a hybrid drop generator membrane vibration waveform that the operator might not be able to form using a different frequency generator.

In an additional aspect, the invention features a method that includes forming a stream of drops, observing (e.g., viewing) the stream of drops under magnification (e.g., using a magnifying lens and/or an endoscope), and treating the stream of drops to form particles having an arithmetic mean diameter of at most about 3,000 microns.

In some embodiments, magnification can provide a better view of the features (e.g., size, shape, color, surface morphology) of the drops in a stream of drops. This can, for example, enhance quality control during a drop formation process by helping an operator to determine whether drops with desirable features are being formed. Observing a stream of drops under magnification may increase operator efficiency by, for example, allowing an operator to quickly determine whether the apparatus has been properly set up. In some embodiments, a stream of drops can be photographed and/or videotaped.

The resulting photographs and/or videotapes can be used, for example, for training (e.g., to demonstrate what a properly formed stream of drops looks like). In a further aspect, the invention features a method that includes monitoring the temperature of a mixture including first and second materials, forming a stream of drops from the mixture, and treating the stream of drops to form particles having an arithmetic mean diameter of at most about 3,000 microns.

In another aspect, the invention features a drop generator that includes a vessel, a temperature sensor (e.g., a thermocouple) in the vessel, a nozzle, and a membrane. The vessel contains a mixture including first and second materials, and the nozzle and the membrane are configured to form drops with a diameter of at most about 3,000 microns.

In an additional aspect, the invention features a method that includes forming a stream of drops from a mixture contained in a vessel and including first and second materials, and treating the stream of drops to form particles having a mean arithmetic diameter of at most about 3,000 microns. The vessel includes a thermistor.

In a further aspect, the invention features a drop generator that includes a vessel, a thermistor in the vessel, a nozzle, and a membrane. The vessel contains a mixture including first and second materials, and the nozzle and the membrane are configured to form drops with a diameter of at most about 3,000 microns.

In an additional aspect, the invention features a drop generator including a vessel containing a mixture including first and second materials, a nozzle, a membrane, a shaft connecting the vessel to the nozzle, and a heater connected to the shaft. The nozzle and the membrane are configured to form drops with a diameter of at most about 3,000 microns.

In some embodiments, the temperature of a mixture that is used to form a stream of drops and/or the temperature of a vessel containing the mixture can be monitored. The temperature of the mixture and/or vessel can be monitored using, for example, a temperature sensor and/or thermistor. By monitoring the temperature of the mixture and/or vessel, an operator may be able to maintain the temperature at a relatively constant level and/or ensure that the temperature is not too high or low. In certain embodiments, the temperature of the mixture and/or vessel can be adjusted (e.g., using a heater, such as a heating coil). In some embodiments, the use of a heater (e.g., a heating coil) with a drop generator can help to maintain the temperature and/or viscosity of a mixture and/or drops at a desirable level.

In another aspect, the invention features a method that includes monitoring the pressure of a gas in a vessel (e.g., using a pressure sensor) containing a mixture including first and second materials. The method further includes forming a stream of drops from the mixture and treating the stream of drops to form particles that have an arithmetic mean diameter of at most about 3,000 microns.

In an additional aspect, the invention features a drop generator including a vessel, a pressure sensor (e.g., a strain gauge, a piezoelectric element) in the vessel, a nozzle, and a membrane. The vessel contains a gas and a mixture including first and second materials. The nozzle and the membrane are configured to form drops with a diameter of at most about 3,000 microns.

In certain embodiments, by monitoring the pressure of a gas, an operator can maintain that pressure at a relatively constant level and/or ensure that the pressure of the gas is not too high or too low. In some embodiments, when the pressure of the gas is maintained at a relatively constant level, the flow rate of the mixture from the vessel can also be relatively constant.

In a further aspect, the invention features a method that includes monitoring the pressure differential between a source containing a mixture that includes first and second materials and a vessel that is in fluid communication with the source. The method also includes flowing the mixture from the source to the vessel, forming a stream of drops from the mixture, and treating the stream of drops to form particles. In some embodiments, the method includes flowing the mixture from the source to the vessel when the pressure differential reaches a predetermined value. In certain embodiments, the method includes flowing the mixture from the source to the vessel when the pressure differential is at least about 0.125 psi (e.g., at least about 0.5 psi, at least about one psi, at least about two psi, at least about five psi, at least about seven psi, at least about 10 psi, at least about 15 psi, at least about 20 psi, at least about 25 psi).

In some embodiments, the source can be used to maintain a relatively constant amount of the mixture in the vessel. In certain embodiments, the source and the vessel can be releasably attached to each other. Thus the source can be detached from the vessel to, for example, change, refill, and/or clean the source.

In another aspect, the invention features a method that includes forming a non-laminar stream of a mixture, flowing the non-laminar stream from a vessel to a drop generator, forming drops from the stream, and treating the drops to form particles having an arithmetic mean diameter of at most about 3,000 microns.

In a further aspect, the invention features a method that includes forming a helical stream of a mixture, flowing the helical stream from a vessel to a drop generator, forming drops from the stream, and treating the drops to form particles having an arithmetic mean diameter of at most about 3,000 microns.

In certain embodiments, a non-laminar and/or helical stream of a mixture may be relatively homogeneous. In some embodiments, the use of a non-laminar and/or helical stream of a mixture during drop generation can lead to a relatively low amount of drag on the mixture during drop generation, and/or can limit stagnation of the mixture (e.g., within a shaft between the vessel and the drop generator). In certain embodiments, as the drag on the mixture and/or the stagnation of the mixture decreases, the homogeneity of the composition of the resulting particles can increase.

In an additional aspect, the invention features a method of making particles. The method includes forming a stream of drops and spraying the stream of drops with a first material (e.g., a gelling agent, a therapeutic agent, a polymer, a gelling precursor, a porosity-enhancing agent). The particles have an arithmetic mean diameter of at most about 3,000 microns.

In some embodiments, forming a stream of drops and spraying the stream of drops with a material (e.g., a gelling agent, a therapeutic agent, a polymer, a gelling precursor, a porosity-enhancing agent) can cause a coating of the material to be formed on the drops. In certain embodiments, particles that are formed from the stream of drops may retain this coating. In some embodiments, coated particles may therefore be relatively easily formed.

In an additional aspect, the invention features a method of making particles. The method includes forming a stream of drops in an atmosphere having a relative humidity of at least about 20 percent and/or at most about 100 percent (e.g., at most about 90 percent), and treating the stream of drops to form particles that have an arithmetic mean diameter of at most about 3,000 microns.

In a further aspect, the invention features a method of making particles. The method includes forming a stream of drops in an atmosphere having a relative humidity of at least about 70 percent and/or at most about 100 percent, and treating the stream of drops to form particles that have an arithmetic mean diameter of at most about 3,000 microns.

In an additional aspect, the invention features a method of making particles. The method includes forming a stream of drops in an atmosphere having a relative humidity of at most about 40 percent, and treating the stream of drops to form particles that have an arithmetic mean diameter of at most about 3,000 microns.

In some embodiments, the relative humidity of an atmosphere in which drops are formed can be controlled (e.g., maintained at a relatively consistent level). In certain embodiments, maintaining the relative humidity of an atmosphere in which drops are formed at a relatively consistent level may result in the formation of drops and/or particles having a relatively uniform size and/or composition. In some embodiments, drops that are formed in an atmosphere with a relatively high relative humidity may, for example, be relatively easily coated (e.g., by spraying) during drop formation, and/or may retain coatings relatively well. In certain embodiments, drops that are formed in an atmosphere with a relatively low relative humidity and that include one or more bioerodible materials may be unlikely to experience significant premature erosion.

In another aspect, the invention features a method of making particles. The method includes forming a stream of drops in an atmosphere having a pressure that is greater than one atmosphere, and treating the stream of drops to form particles that have an arithmetic mean diameter of at most about 3,000 microns (e.g., at most about 1,000 microns, at most about 500 microns, at most about 400 microns, at most about 300 microns, at most about 200 microns, at most about 100 microns).

In some embodiments, particles formed from drops that are generated in an atmosphere having a pressure that is greater than one atmosphere may be smaller than particles formed from drops that are generated in an atmosphere having a pressure of about one atmosphere. Relatively small particles may be used, for example, in chemembolization and/or delivery of therapeutic agents (intravascularly and/or by direct injection). In certain embodiments, relatively small particles may be used as bulking agents (e.g., as injectable dermal treatments for wrinkles and/or scars). In some embodiments, relatively small particles may be used in neurological applications.

In an additional aspect, the invention features a method of making particles. The method includes forming a stream of drops from a mixture including a first polymer and cross-linking a second polymer that is in and/or on the drops (e.g., by applying a laser, ultraviolet radiation, and/or heat to the stream of drops). After the second polymer is cross-linked, the stream of drops is treated to form the particles.

In certain embodiments, cross-linking a stream of drops before treating the stream of drops to form particles may stabilize the drops prior to their treatment.

In a further aspect, the invention features a method of making particles. The method includes forming a stream of drops from a first mixture including a polymer and a gelling precursor, and contacting the stream of drops with a moving (e.g., vibrating, circulating) mixture comprising a gelling agent (e.g., calcium chloride). The particles have an arithmetic mean diameter of at most about 3,000 microns.

In some embodiments, the motion of the gelling agent mixture can limit the amount of settling by the mixture and/or can increase the amount of reaction between the mixture and the drops.

In a further aspect, the invention features a method of making particles. The method includes forming a stream of drops from a first mixture including a polymer and a gelling precursor, and flowing the stream of drops into a moving (e.g., vibrating) vessel. The particles have an arithmetic mean diameter of at most about 3,000 microns.

In certain embodiments, the moving vessel may contain a mixture including a gelling agent. In some embodiments, the motion of the vessel can cause the mixture to move which can, for example, limit the amount of settling by the mixture and/or increase the amount of reaction between the mixture and the drops.

In another aspect, the invention features a method of making particles. The method includes forming a stream of drops from a mixture including a polymer and a gelling precursor, contacting some of the drops with a first cavity in a housing, and contacting some of the drops with a second cavity in the housing. The particles have an arithmetic mean diameter of at most about 3,000 microns.

In an additional aspect, the invention features a method of making particles. The method includes forming a stream of drops from a mixture including a polymer and a gelling precursor, contacting some of the drops with a first cavity in a housing, and contacting some of the drops with a second cavity in the housing. The first cavity contains a mixture including a gelling agent, and the second cavity contains a mixture including a gelling agent. The particles have an arithmetic mean diameter of at most about 3,000 microns.

In certain embodiments, the cavities can be used to collect the drops relatively easily and/or to segregate different types of drops (e.g., based on the size, shape, and/or age of the drops). In some embodiments, the housing may move (e.g., rotate) so that, for example, the housing can move after a certain duration of time (e.g., every ten minutes) to collect a new set of drops in a different cavity.

In an additional aspect, the invention features a method of making particles. The method includes contacting a stream of drops including a polymer and a gelling precursor with a gelling agent and a cross-linking agent both contained in a vessel. The particles have an arithmetic mean diameter of at most about 3,000 microns.

In some embodiments, contacting drops that include a polymer and a gelling precursor with both a cross-linking agent and a gelling agent to form particles can allow the particles to be formed relatively quickly and/or efficiently.

In certain embodiments, drops that include a polymer and a gelling precursor can be contacted with a vessel that includes a gelling agent. After at least some of the gelling precursor in the drops has been gelled by the gelling agent, the gelling agent can be removed (e.g., drained) from the vessel and a cross-linking agent can be added to the vessel, which can cross-link the polymer in the drops. Thus, the same vessel can be used for both the gelling and the cross-linking of the drops.

In a further aspect, the invention features a method of making particles. The method includes forming a stream of a mixture including first and second materials, flowing the stream through an angle of less than 90 degrees (e.g., less than about 70 degrees, less than about 50 degrees, less than about 30 degrees), and treating the stream to form a plurality of particles having an arithmetic mean diameter of at most about 3,000 microns.

In some embodiments, a stream that is flowed through an angle of less than 90 degrees (e.g., less than about 70 degrees) may have a higher flow rate than a stream that is flowed through an angle of at least 90 degrees. The higher flow rate may, for example, cause the stream to reach a drop generator relatively quickly, and/or to be relatively unlikely to experience significant fluctuations in temperature prior to reaching a drop generator. In certain embodiments, increasing the flow rate of the stream may result in a reduced likelihood of stagnation by the stream. In some embodiments, increasing the flow rate of the stream may result in the stream being less turbulent than it would be at a lower flow rate.

Features and advantages are in the description, drawings, and claims.

DESCRIPTION OF DRAWINGS

FIG. 1A is a schematic of an embodiment of a process for manufacturing particles.

FIGS. 3A-3L are illustrations of embodiments of a process for manufacturing particles.

FIGS. 5A-5D are illustrations of embodiments of a process for manufacturing particles.

FIGS. 14A and 14B are side views of an embodiment of a process for manufacturing particles.

FIG. 21A is a schematic illustrating injection of a composition including particles into a vessel.

FIGS. 24A and 24B are illustrations of embodiments of a process for manufacturing particles.

DETAILED DESCRIPTION

Figure 1B:
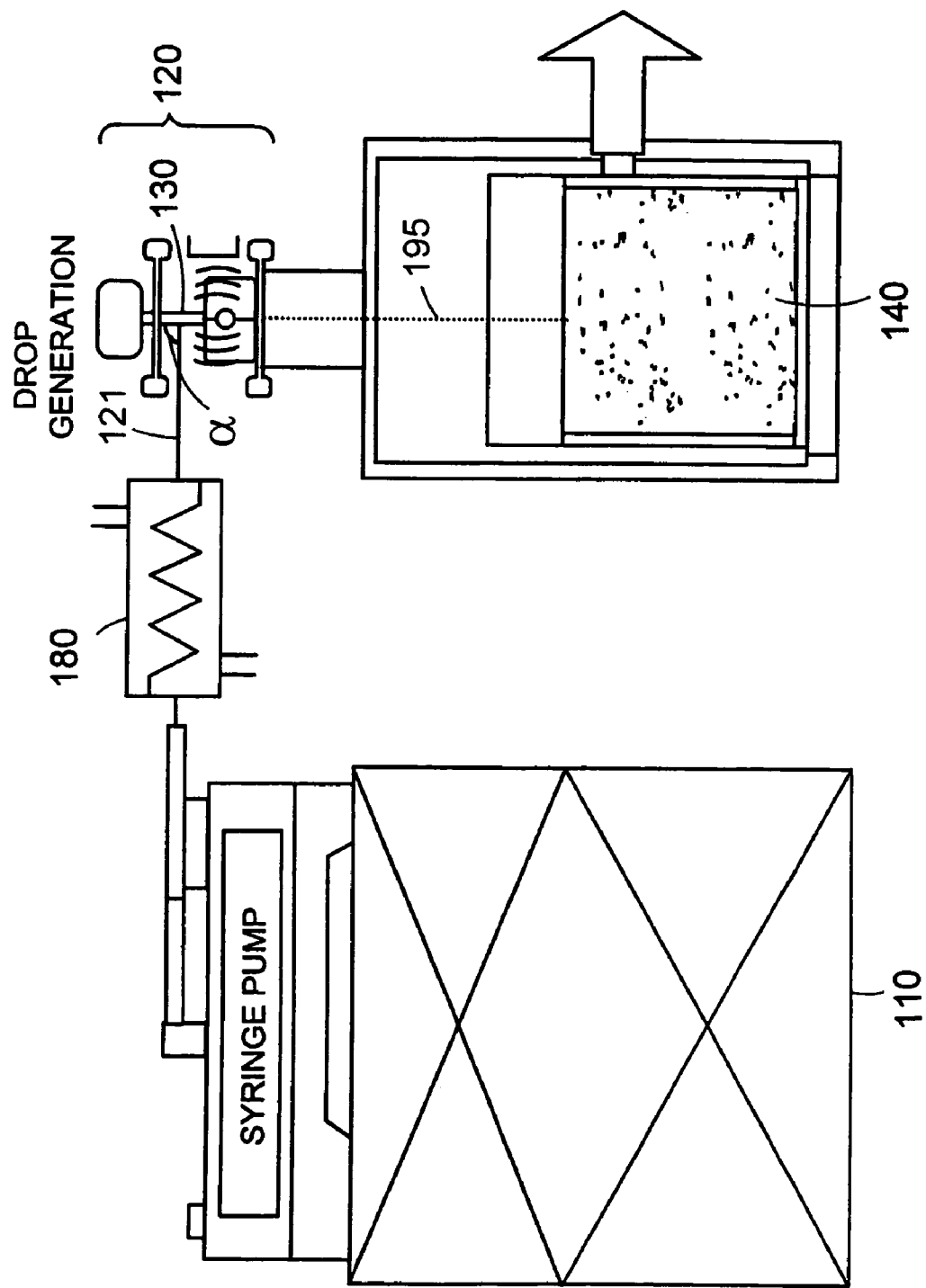
FIG. 1B is an enlarged schematic of region 1B in FIG. 1A.
Figure 2:
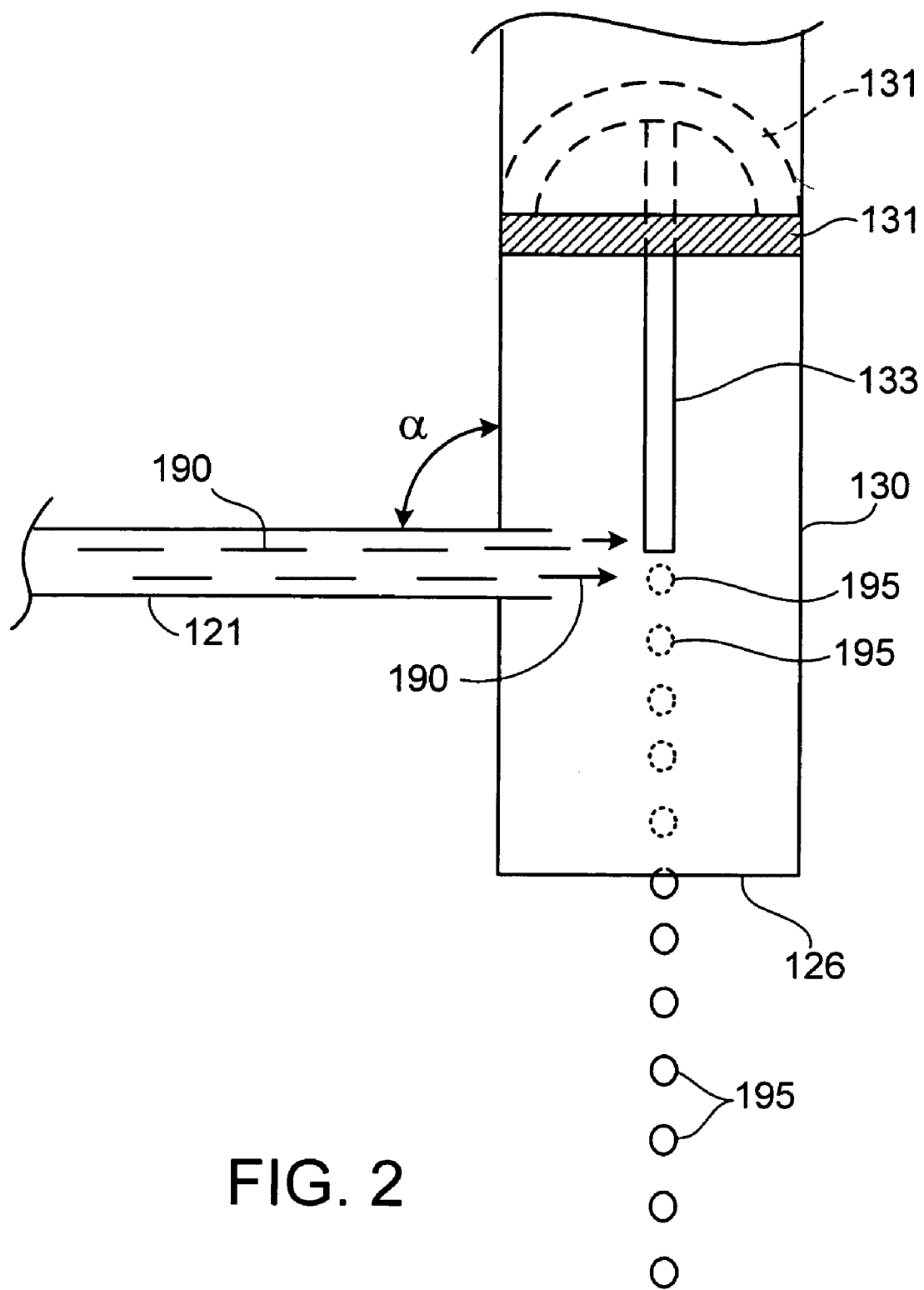
FIG. 2 is a side view of an embodiment of an apparatus for manufacturing particles.

FIGS. 1A, 1B, and 2 show a system 100 for producing particles. System 100 includes a flow controller 110, a drop generator 120 including a nozzle 130, a gelling vessel 140, a reactor vessel 150, an optional gel dissolution chamber 160, and a filter 170. An example of a commercially available drop generator is the model NISCO Encapsulation unit VAR D (NISCO Engineering, Zurich, Switzerland).

Flow controller 110 includes a high pressure pumping apparatus, such as a syringe pump (e.g., model PHD4400, Harvard Apparatus, Holliston, Mass.). Flow controller 110 delivers a stream 190 of a solution including a polymer and a gelling precursor to a viscosity controller 180, which heats the solution to reduce its viscosity prior to delivery to drop generator 120. Viscosity controller 180 is connected to nozzle 130 of drop generator 120 via tubing 121. After stream 190 has traveled from flow controller 180 through tubing 121, stream 190 flows around a corner having an angle α, and enters nozzle 130. As shown, angle α is about 90 degrees. However, in some embodiments, angle α can be less than 90 degrees (e.g., less than about 70 degrees, less than about 50 degrees, less than about 30 degrees).

As stream 190 enters nozzle 130, a membrane 131 in nozzle 130 is subjected to a periodic disturbance (a vibration). The vibration causes membrane 131 to pulse upward (to the position shown in phantom in FIG. 2) and then return back to its original position. Membrane 131 is connected to a rod 133 that transmits the vibration of membrane 131, thereby periodically disrupting the flow of stream 190 as stream 190 enters nozzle 130. This periodic disruption of stream 190 causes stream 190 to form drops 195. Drops 195 fall into gelling vessel 140, where drops 195 are stabilized by gel formation. During gel formation, the gelling precursor in drops 195 is converted from a solution to a gel form by a gelling agent contained in gelling vessel 140. The gel-stabilized drops are then transferred from gelling vessel 140 to reactor vessel 150, where the polymer in the gel-stabilized drops is reacted (e.g., with a cross-linking agent), to form particles. Thereafter, the particles are transferred to gel dissolution chamber 160. In gel dissolution chamber 160, the gelling precursor (which was converted to a gel) in the particles is dissolved. After the particle formation process has been completed, the particles can be filtered in filter 170 to remove debris, and sterilized and packaged as a composition including particles.

Methods of making particles are described, for example, in U.S. Patent Application Publication No. US 2004/0096662 A1, published on May 20, 2004, and entitled "Embolization", and in U.S. patent application Ser. No. 10/858,253, filed on Jun. 1, 2004, and entitled "Embolization", both of which are incorporated herein by reference.

One or more aspects of a particle formation process can be varied to, for example, form particles of a particular size and/or shape, and/or to enhance the efficiency of the particle formation process.

As an example, in some embodiments, a drop generation process can be manipulated to form particles of different shapes. In some such embodiments, a drop generator can be used to form drops according to the procedure described above with reference to FIGS. 1A, 1B, and 2. However, the membrane vibration waveform of the drop generator can be selected to cause particles of a particular shape to be formed.

For example, FIGS. 3A-3L show how different membrane vibration waveforms can be applied to drop generator 120 to form differently shaped particles.

First, FIG. 3A shows the formation of non-spherical drops 202 using drop generator 120. Non-spherical drops 202 are formed by vibrating membrane 131 of drop generator 120 at a vibration represented by a square waveform 204, as shown in FIG. 3B. One drop is formed during each cycle (C) of the waveform, which includes an amount of time during which drop generator 120 is turned on, followed by an equal amount of time during which drop generator 120 is turned off. When a square waveform is used, the power of drop generator 120 is either turned to maximum power or to no power (power off). Switching back and forth between maximum power and no power causes membrane 131 to pulse, as shown in FIG. 3B.

Waveform 204 is a square waveform because it switches back and forth between only two phases (maximum power and no power) and each of its "maximum power" phases lasts for the same amount of time as each of its "no power" phases. As shown in FIG. 3A, square waveform 204 leads to the formation of discrete non-spherical drops 202. For purposes of discussion, non-spherical drops 202 are shown as having a cylindrical shape. The shape of drops 202 may depend on the viscosity and/or temperature of the mixture used to form drops 202. For example, in some embodiments, a mixture with a higher viscosity and/or a lower temperature may lead to the formation of drops that are cylindrical, while a mixture with a lower viscosity and/or a higher temperature may lead to the formation of drops that are somewhat cylindrical but that include a taper at one or both of their ends. Drops 202 form during the "no power" phases of the membrane vibration. As drops 202 fall from drop generator 120, they eventually change in shape, forming spheroidal drops 201 that later turn into spherical drops 203.

In certain embodiments, a non-square or non-rectangular membrane vibration waveform can be used to vibrate the membrane of a drop generator. In general, non-square or non-rectangular waveforms can be angular (e.g., triangular) or non-angular (e.g., sinusoidal) in shape. FIGS. 3C-3L show various examples of drop generation occurring as a result of non-square and non-rectangular membrane vibration waveforms.

For example, FIG. 3C shows the formation of spherical drops 208 through drop generator 120 when membrane 131 vibrates at a frequency having a sinusoidal waveform 206, shown in FIG. 3D. When sinusoidal waveform 206 is used to vibrate membrane 131, the power of drop generator 120 follows a sinusoidal path between no power and maximum power. The use of sinusoidal waveform 206 to vibrate membrane 131 results in the formation of substantially spherical and discrete drops 208.

Figure 3F:
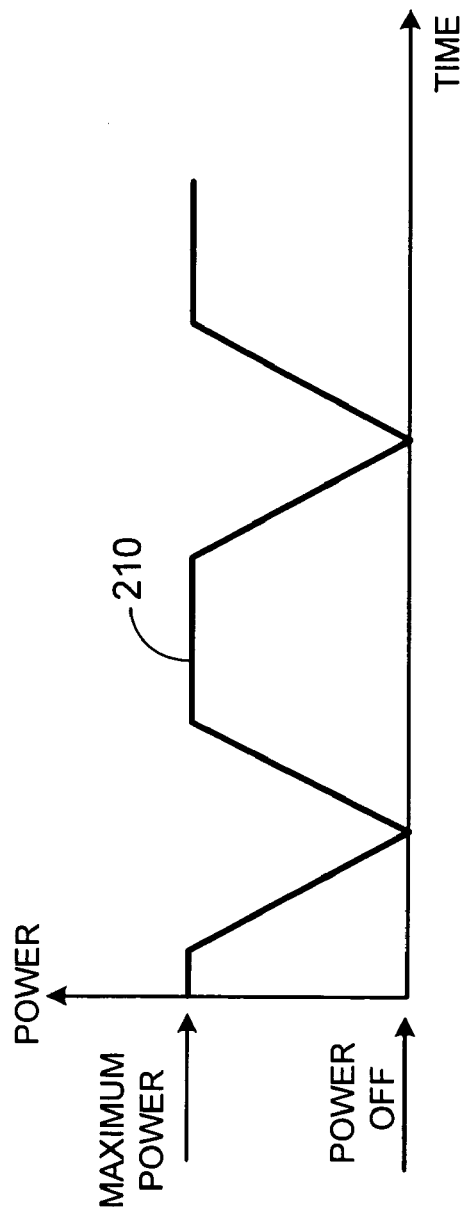
Figure 3E:
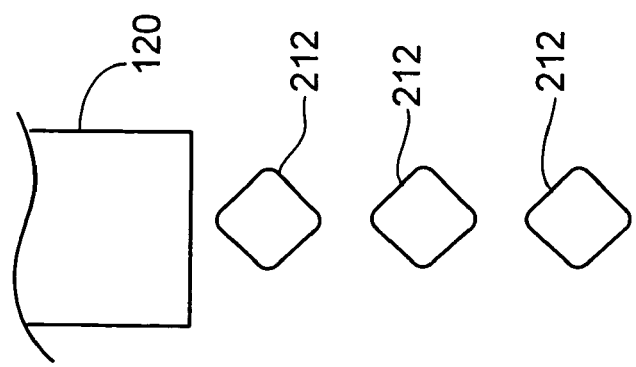

FIG. 3E shows the formation of drops 212 when membrane 131 vibrates at a frequency having an on-interval triangular waveform 210, as shown in FIG. 3F. On-interval triangular waveform 210 may result in the formation of diamond-shaped drops, as shown.

Figure 3H:
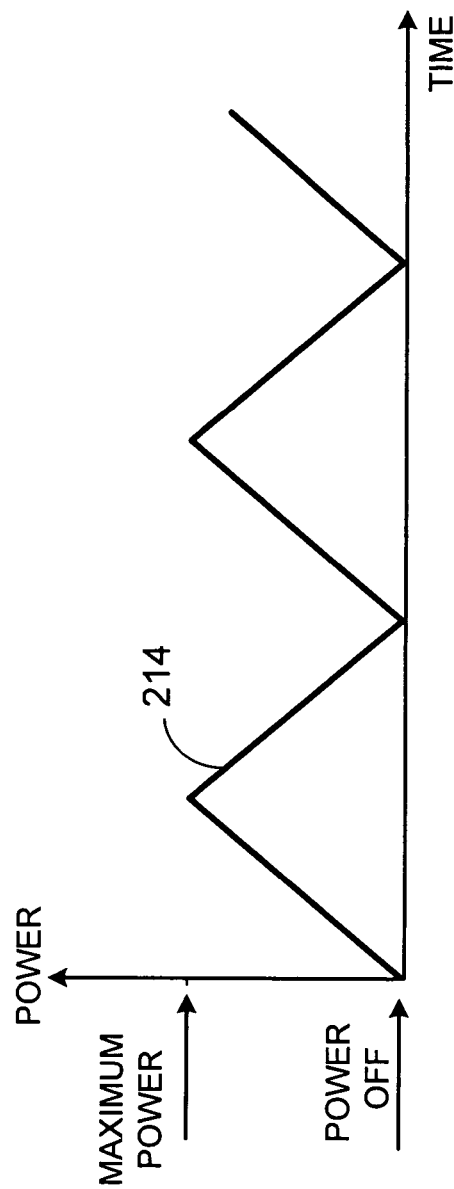
Figure 3G:
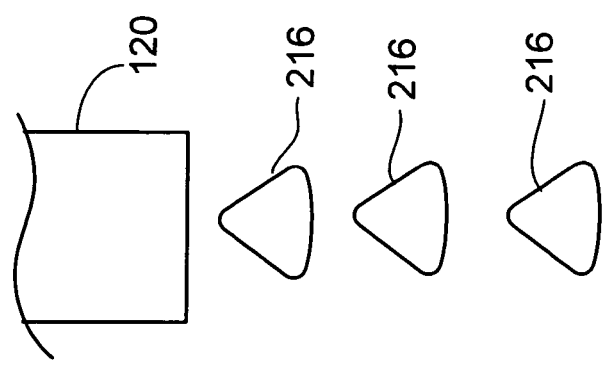

FIG. 3G shows the formation of drops 216 when membrane 131 vibrates at a frequency having a sawtooth waveform 214, as shown in FIG. 3H. Sawtooth waveform 214 may result in the formation of conical drops, as shown.

Figure 3J:
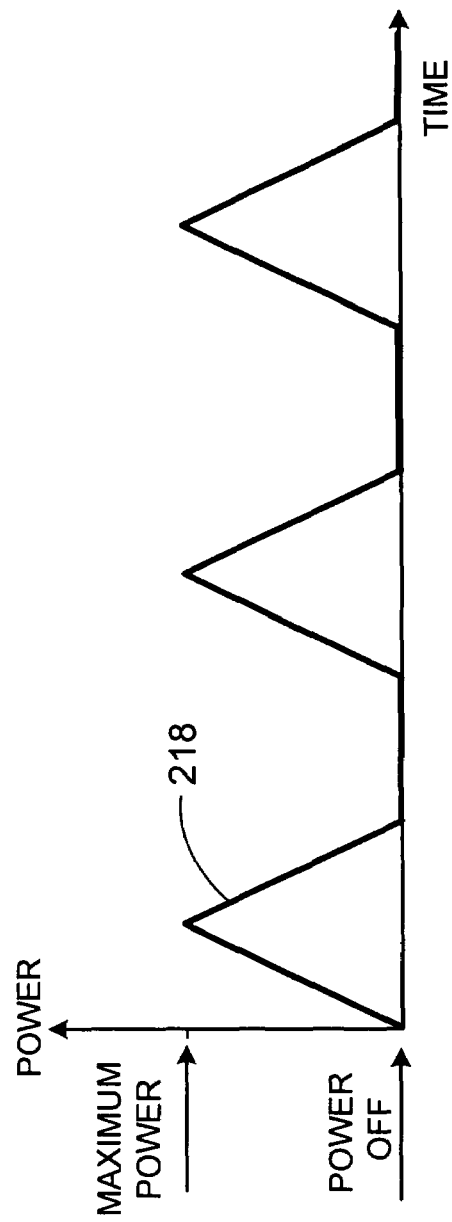
Figure 3I:
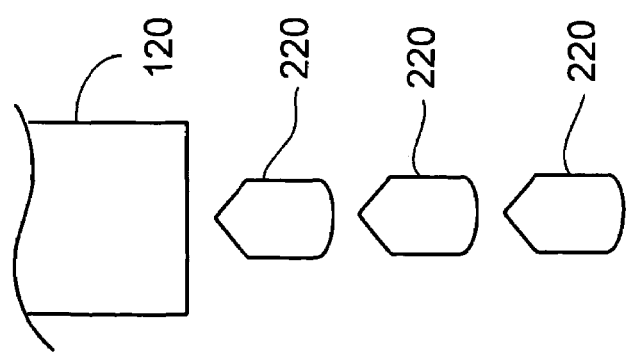

FIG. 3I shows the formation of drops 220 when membrane 131 vibrates at a frequency having an off-interval triangular waveform 218, as shown in FIG. 3J. Off-interval triangular waveform 218 may result in the formation of drops that are cylindrical and that have a conical top, as shown.

Figure 3L:
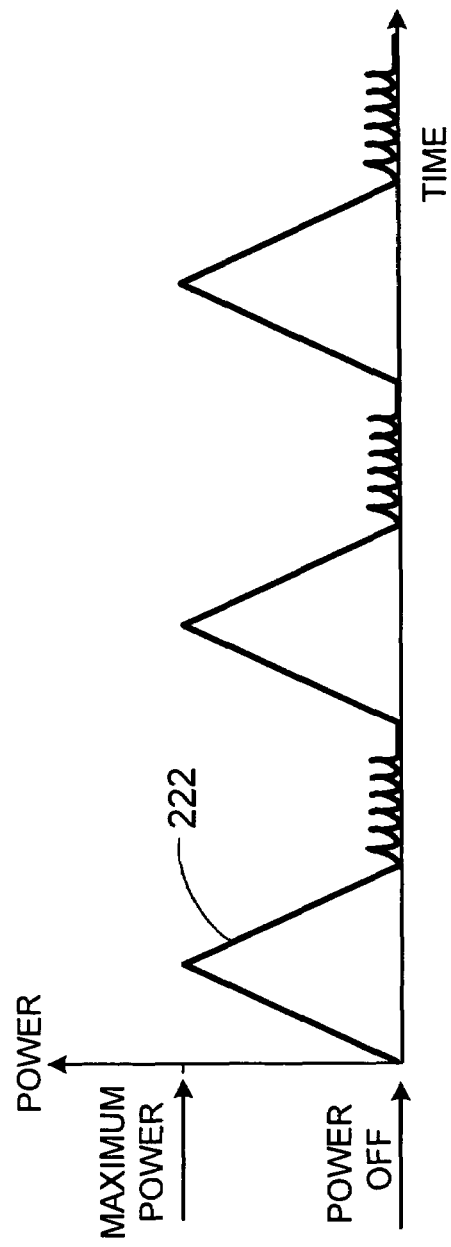
Figure 3K:
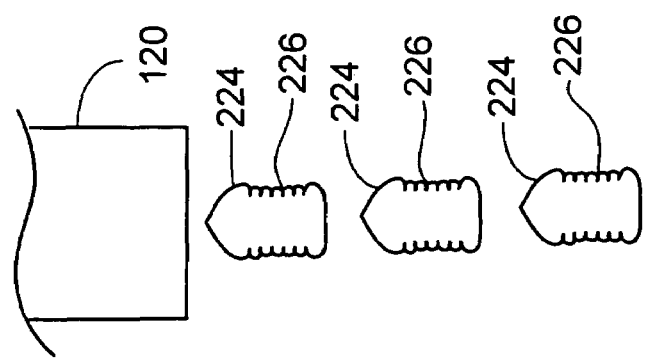

FIG. 3K shows the formation of drops 224 when membrane 131 vibrates at a frequency having a modified off-interval triangular waveform 222, as shown in FIG. 3L. Modified off-interval triangular waveform 222 may result in the formation of drops with a shape similar to those of drops 220 (FIG. 3I), but further including grooves 226, as shown.

In some embodiments in which non-spherical (e.g., conical, spheroidal, cylindrical) drops are formed, a vessel that captures the drops (e.g., a vessel containing a gelling agent solution) may be located relatively close to the bottom of the drop generator. In certain embodiments, locating the vessel relatively close to the bottom of the drop generator may limit the likelihood of the drops turning into spherical drops.

Figure 4:
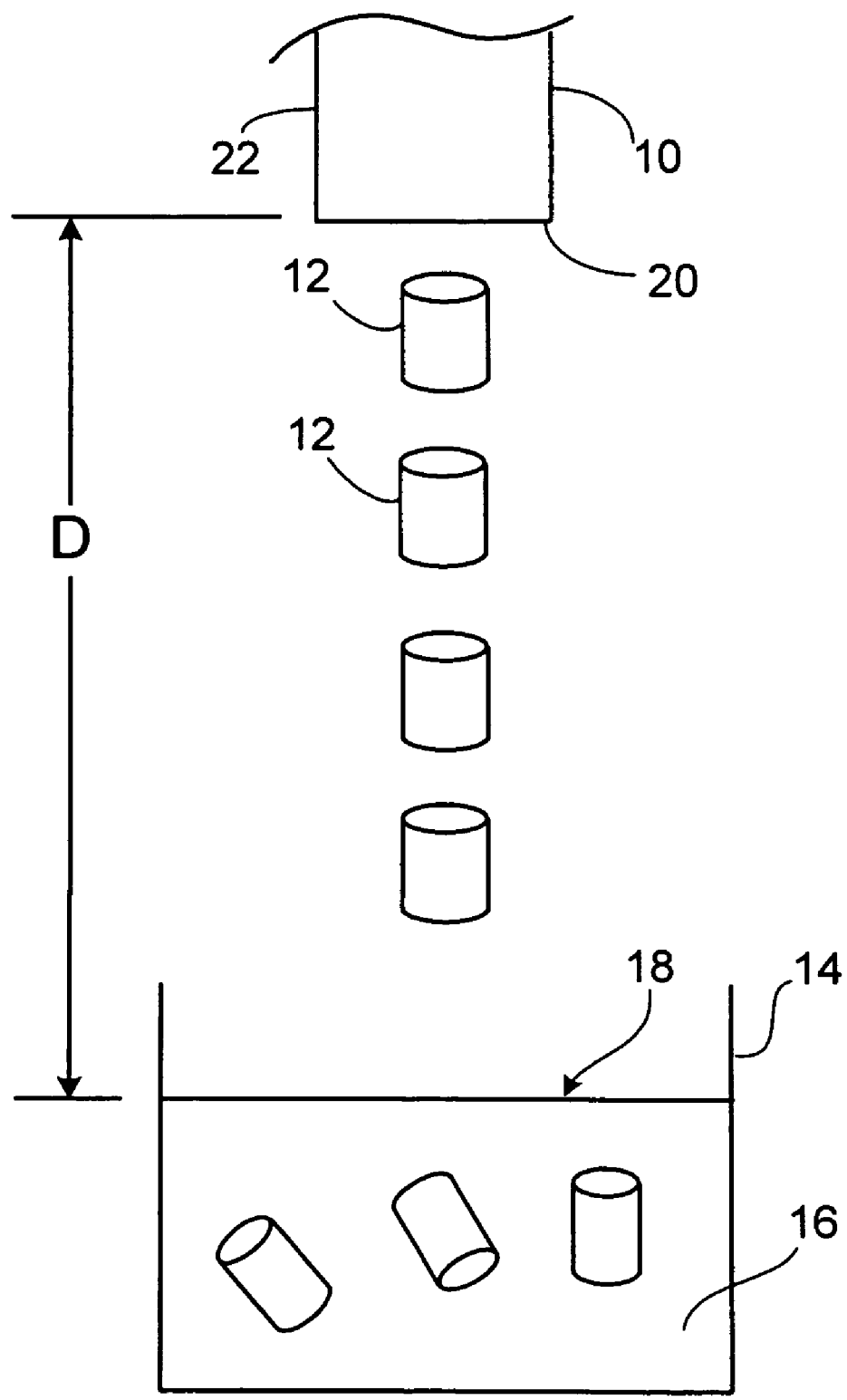
FIG. 4 is a side view of an embodiment of an apparatus for manufacturing particles.

For example, FIG. 4 shows a drop generator 10 that includes a nozzle 22 and that produces substantially cylindrical drops 12. A vessel 14 containing a gelling agent solution 16 is disposed beneath drop generator 10, such that the surface 18 of gelling agent solution 16 is located at a distance "D" from the bottom 20 of nozzle 22. Distance "D" can be selected to limit the likelihood of cylindrical drops 12 turning into spherical drops as they fall. In some embodiments, distance "D" can be at least about 0.5 inch (e.g., at least about one inch, at least about two inches, at least about three inches, at least about four inches), and/or at most about five inches (e.g., at most about four inches, at most about three inches, at most about two inches, at most about one inch).

In certain embodiments, a non-uniform membrane vibration frequency can be used with a drop generator to form particles of different sizes. In some embodiments, a non-uniform membrane vibration frequency can be used to form drops of at least two different sizes during the same drop generation process. Thus, in certain embodiments, one drop generation process can be used to produce differently sized particles that can, for example, be used for different applications.

FIG. 5A shows the formation of drops 302 using a drop generator nozzle 300, at a uniform membrane vibration frequency that is represented by a rectangular waveform 304, as shown in FIG. 5B. Waveform 304 is a rectangular waveform because it switches back and forth between only two phases (power on and power off) and each of its "power on" phases lasts for a different amount of time from each of its "power off" phases. Rectangular waveform 304 causes drops 302 to have a cylindrical shape.

The membrane vibration frequency of the drop generation process shown in FIGS. 5A and 5B is uniform because each cycle (C1) of rectangular waveform 304 is identical to the other cycles. As shown in FIG. 5B, rectangular waveform 304 has a duty cycle of 40/60. The duty cycle of a membrane vibration waveform represents the amount of time it takes for the drop generator to produce one drop (cycle C1), and the percentage of that time during which the power of the drop generator is turned on, followed by the percentage of time during which the power of the drop generator is turned off. For example, if a membrane vibration waveform has a duty cycle of 70/30, then during the cycle of time it takes to produce one drop, the power of the drop generator is on for the first 70 percent of the cycle and off for the remaining 30 percent of the cycle. Rectangular waveform 304 has a uniform membrane vibration duty cycle of 40/60 because each cycle (C1) of rectangular waveform 304 has a membrane vibration duty cycle of 40/60.

Figure 5D:
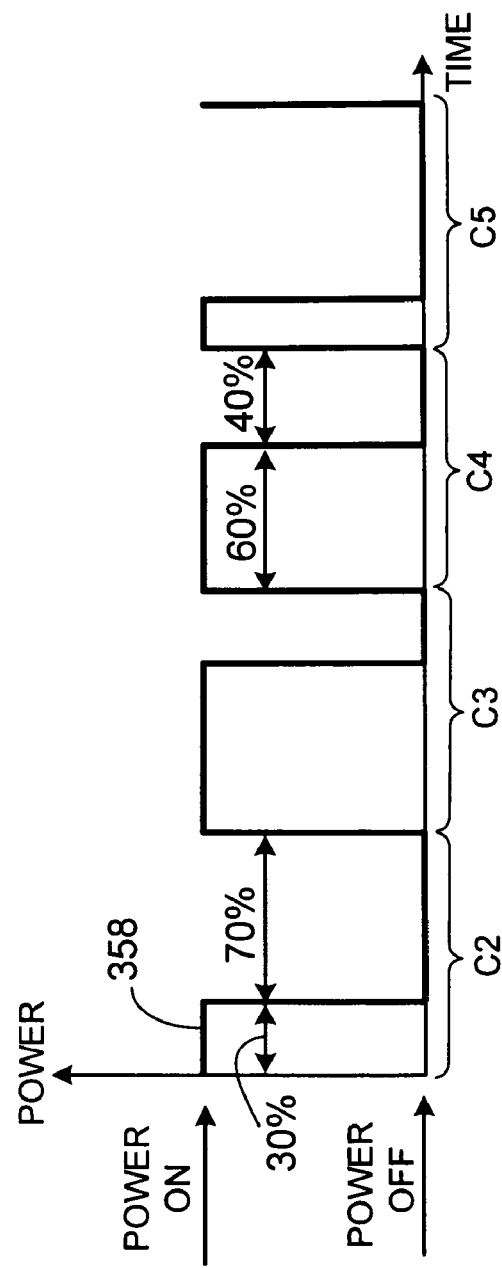
Figure 5C:
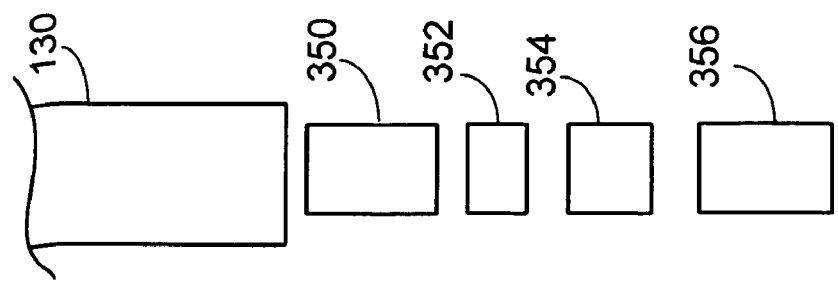

By contrast, FIGS. 5C and 5D show the formation of differently sized drops 350, 352, 354, and 356 using drop generator 120 (FIGS. 1A, 1B, and 2) and vibrating membrane 131 at a non-uniform membrane vibration frequency represented by a waveform 358, shown in FIG. 5D. A non-uniform membrane vibration frequency is any membrane vibration frequency that is not a uniform membrane vibration frequency. As shown in FIG. 5D, each cycle (C2, C3, C4, and C5) of waveform 358 lasts for a different length of time and has a different duty cycle. For example, cycle C2 has a duty cycle of 30/70, while cycle C4 has a duty cycle of 60/40. The size of a drop that forms during a cycle depends on the length of the cycle and the duty cycle. Thus, drops 350, 352, 354, and 356 all have different sizes. Accordingly, using a non-uniform membrane vibration frequency to generate drops can allow differently sized particles to be formed during one particle formation process.

Figure 6:
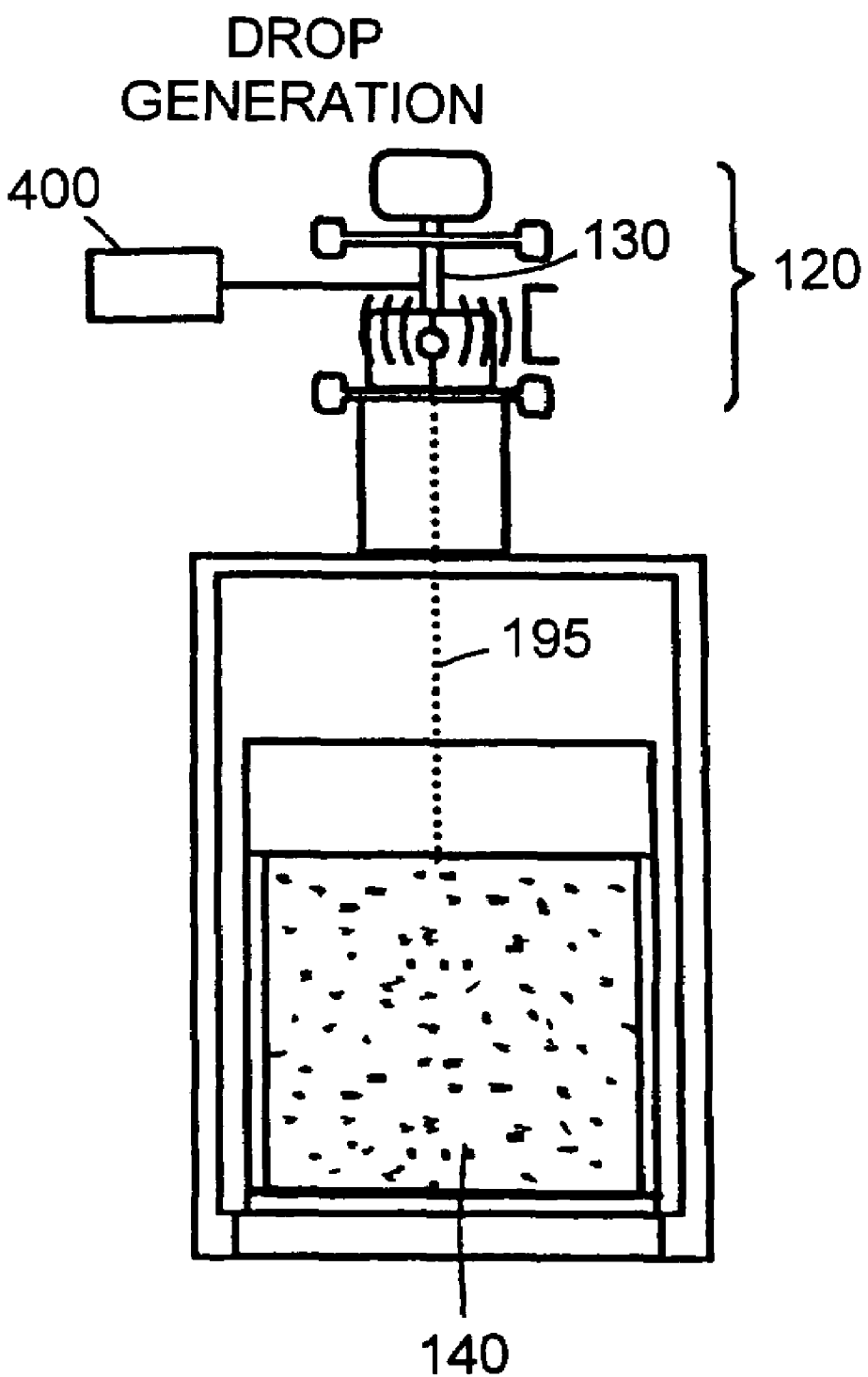
FIG. 6 is a side view of an embodiment of an apparatus for manufacturing particles.

In some embodiments, a dual-channel frequency generator can be used with a drop generator. FIG. 6 shows a dual-channel frequency generator 400 being used in conjunction with drop generator 120 (FIGS. 1A, 1B, and 2). Examples of commercially available dual-channel frequency generators include the Dual Channel Tektronix AFG300 Series Function/Arbitrary Waveform Generator and the Tektronix AFG320 Generator, both available from Tektronix.

In certain embodiments, dual-channel frequency generator 400 can be used to generate two separate membrane vibration frequencies (e.g., having differently shaped waveforms), which can together form one hybrid membrane vibration frequency. In some embodiments, at least one of the membrane vibration frequencies can have a non-square or non-rectangular waveform.

In certain embodiments, dual-channel frequency generator 400 can be used to generate one frequency for a device that is used to observe (e.g., view) drops 195 as they are formed and/or as they fall from drop generator 120, and can be used to generate another frequency to vibrate membrane 131. Examples of devices that can be used to observe drops 195 include lights (e.g., strobe lights), cameras, and videocameras. In some embodiments, combinations of observation devices (e.g., a strobe light and a videocamera) can be used. A device that is used to observe drops 195 can operate at frequency that is the same as, or different from, the vibration frequency of the drop generator nozzle.

In some embodiments, the frequency that is used to operate an observation device can be at least about one Hertz (e.g., at least about five Hertz, at least about 10 Hertz, at least about 25 Hertz, at least about 50 Hertz, at least 50.1 Hertz, at least about 100 Hertz, at least about 500 Hertz, at least about 1,000 Hertz, at least about 2,000 Hertz, at least about 3,000 Hertz, at least about 4,000 Hertz), and/or at most 5,000.1 Hertz (e.g., at most about 5,000 Hertz, at most about 4,000 Hertz, at most about 3,000 Hertz, at most about 2,000 Hertz, at most about 1,000 Hertz, at most about 500 Hertz, at most about 100 Hertz, at most 50.1 Hertz, at most about 50 Hertz, at most about 25 Hertz, at most about 10 Hertz, at most about five Hertz). For example, the frequency that is used to operate an observation device may be about one Hertz.

In some embodiments, the frequency that is used to operate an observation device may depend on the material(s) included in the drops that are being formed. As an example, in certain embodiments, the frequency used to operate an observation device to observe drops that do not contain an additive may be different from the frequency that is used to operate an observation device to observe drops that contain one or more additives, such as iron, iridium, and/or yttrium. As an example, the frequency used to observe drops that are formed of a given material or materials may be different from the frequency used to observe drops that are formed of the same material or materials and that further include an additive.

In certain embodiments, the frequency that is used to vibrate a membrane can be at least about one Hertz (e.g., at least about five Hertz, at least about 10 Hertz, at least about 25 Hertz, at least about 50 Hertz, at least about 100 Hertz, at least about 500 Hertz, at least about 800 Hertz, at least about 1,000 Hertz, at least about 2,000 Hertz, at least about 3,000 Hertz, at least about 4,000 Hertz), and/or at most about 5,000 Hertz (e.g., at most about 4,000 Hertz, at most about 3,000 Hertz, at most about 2,000 Hertz, at most about 1,000 Hertz, at most about 800 Hertz, at most about 500 Hertz, at most about 100 Hertz, at most about 50 Hertz, at most about 25 Hertz, at most about 10 Hertz, at most about five Hertz). For example, the frequency that is used to vibrate a membrane may be about one Hertz.

In some embodiments, the difference between the frequency that is used to vibrate a membrane and the frequency that is used to operate an observation device can be at most about 10 Hertz (e.g., at most about eight Hertz, at most about six Hertz, at most about four Hertz, at most about two Hertz, at most about one Hertz, at most about 0.9 Hertz, at most about 0.5 Hertz, at most about 0.1 Hertz), and/or at least about 0.05 Hertz (e.g., at least about 0.1 Hertz, at least about 0.5 Hertz, at least about 0.9 Hertz, at least about one Hertz, at least about two Hertz, at least about four Hertz, at least about six Hertz, at least about eight Hertz).

Figure 7:
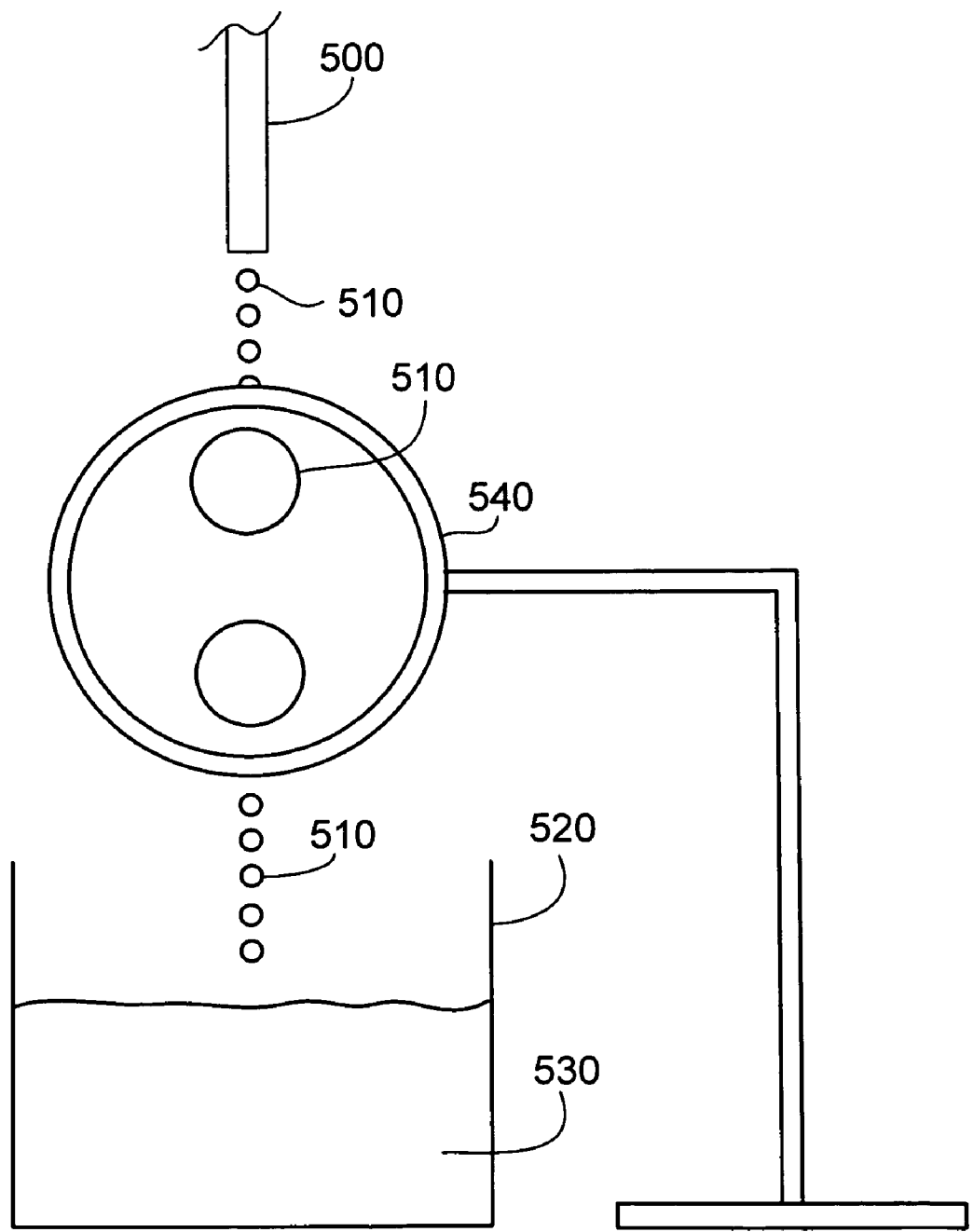
FIG. 7 is an illustration of an embodiment of a process for observing drop formation.

In some embodiments, an observation device can magnify the size of drops during observation. For example, FIG. 7 shows a drop generator 500 producing drops 510 that fall toward a vessel 520 containing a solution 530. A magnifying lens 540 is situated so that drops 510 are magnified as they fall from drop generator 500. This magnification of drops 510 can provide an observer with a better view of drops 510, allowing the observer to, for example, view the shape (e.g., sphericity), surface morphology, and/or color of drops 510.

Other magnifying devices that can be used to observe drops include, for example, endoscopes (e.g., arthroscopes).

In some embodiments, an observation device can be used to store data relating to the drops. For example, drops can be photographed and their images can be transmitted to a computer. Images of the drops can then be stored on the computer and can be used, for example, for training (e.g., to show what well-formed drops look like). In certain embodiments, the drops can be videotaped.

In certain embodiments, drops can be generated by vibrating a drop generator membrane, and can also be viewed using a magnifying device. In some embodiments, drops that are formed without using vibration may be viewed using a magnifying device.

In certain embodiments, a scale (e.g., a ruler) can be situated next to a magnifying lens, such that the operator can determine the approximate sizes of the drops as they fall.

Figure 8:
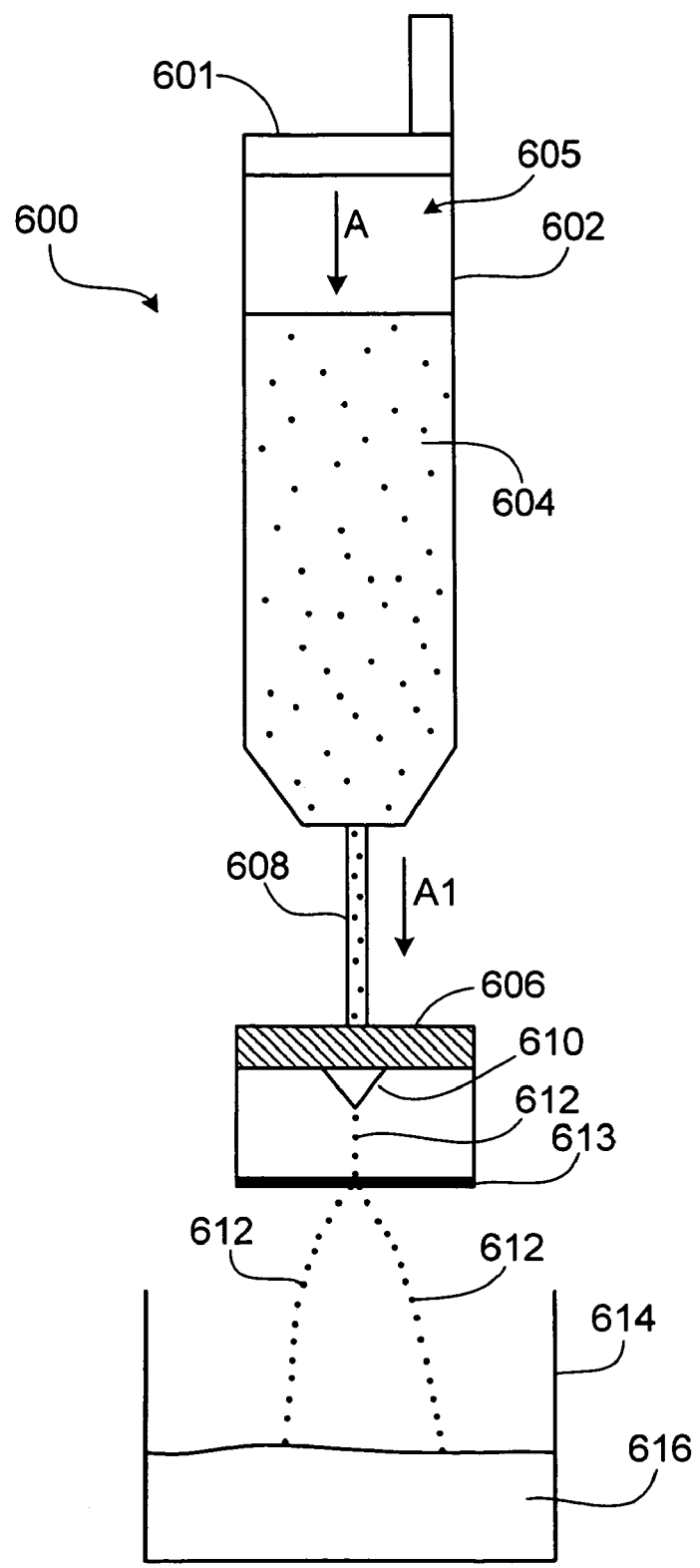
FIG. 8 is a side view of an embodiment of a process for manufacturing particles.

While certain embodiments of drop generator 120 have been described, other types of drop generators can be used to form drops. For example, FIG. 8 shows a drop generator 600 including a vessel 602 with a lid 601. Vessel 602 contains a gas 605 and a solution 604 including a polymer and a gelling precursor. Examples of gases include carbon dioxide, nitrogen, and oxygen. In some embodiments, vessel 602 can include a mixture of one or more gasses (e.g., air). Drop generator 600 further includes a vibrating membrane 606 connected to vessel 602 by a shaft 608, a nozzle 610, and an electrostatic ring 613.

To form drops using drop generator 600, the pressure of gas 605 is increased (e.g., by pressing downward on lid 601 in the direction of arrow A), thereby causing solution 604 to flow out of vessel 602 and through shaft 608 in the direction of arrow A1. Solution 604 then flows through vibrating membrane 606, which causes solution 604 to break apart into drops 612. As drops 612 exit drop generator 600 via nozzle 610, they pass through electrostatic ring 613. Electrostatic ring 613 causes drops 612 to become charged and repel each other. Drops 612 then fall into a vessel 614 containing a solution 616 (e.g., a gelling agent solution). In some embodiments, solution 616 can be grounded. An example of a commercially available drop generator is the Inotech Encapsulator unit IE-50R/NS (Inotech AG, Dottikon, Switzerland).

In some embodiments, the temperature of a mixture (e.g., a solution) used to form drops in a drop generator can be monitored and/or regulated using, for example, one or more temperature sensors (e.g., thermocouples, thermistors), and/or one or more heaters.

Figure 9:
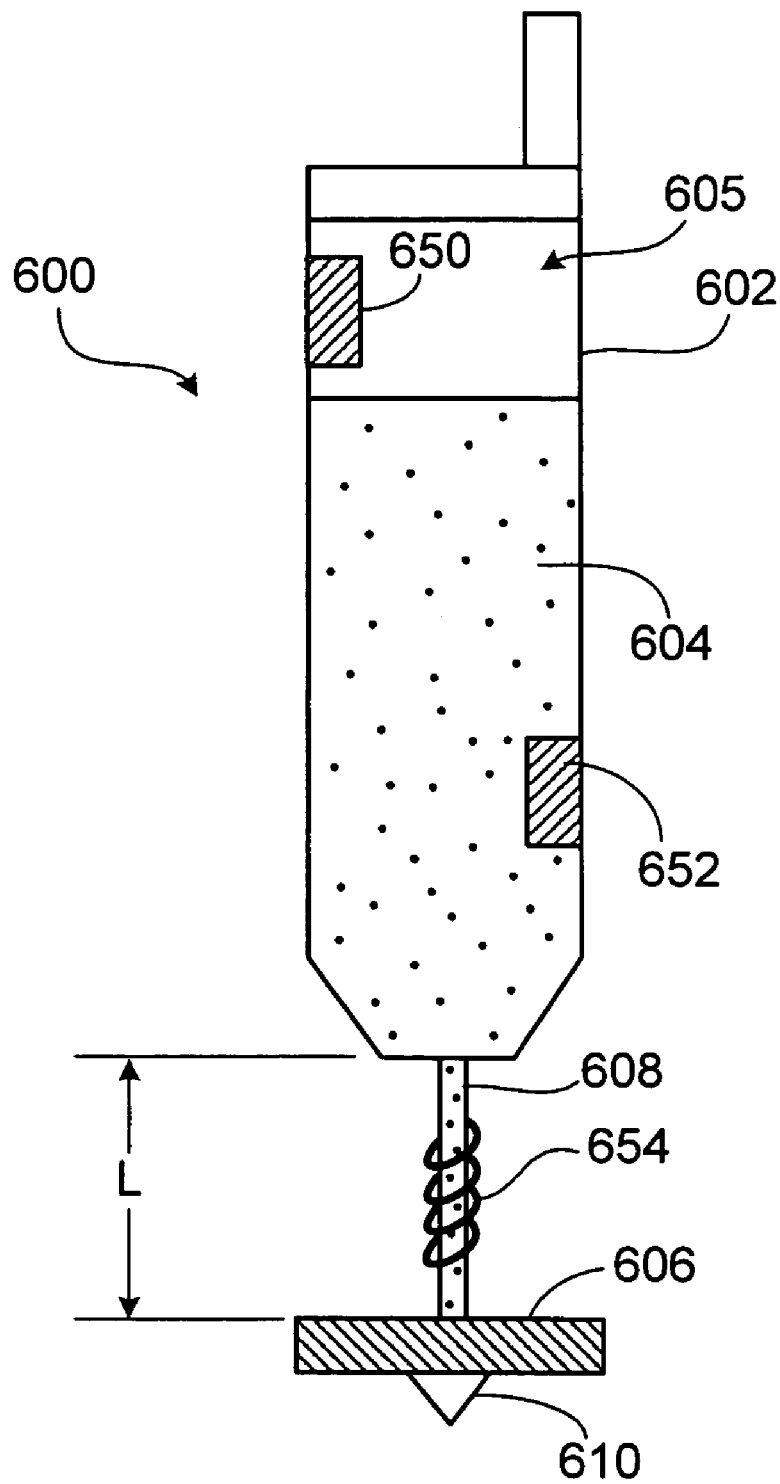
FIG. 9 is a side view of an embodiment of an apparatus for manufacturing particles.

As an example, FIG. 9 shows drop generator 600. As shown in FIG. 9, in some embodiments, drop generator 600 can include a temperature sensor 650 in vessel 602 that can sense the temperature of gas 605. In certain embodiments, drop generator 600 can include a temperature sensor 652 in vessel 602, in contact with solution 604, so that the temperature of solution 604 can be sensed.

After the temperature of gas 605 and/or solution 604 has been sensed, in some embodiments the temperature may then be adjusted accordingly. In certain embodiments, the temperature may be adjusted by one or more heaters. For example, FIG. 9 shows a heating coil 654 wrapped around shaft 608. Heaters such as heating coil 654 can be used to regulate the temperature of solution 604 (e.g., as solution 604 flows through shaft 608). In certain embodiments, the temperature of gas 605 and/or solution 604 can be adjusted using one or more cooling devices.

As shown in FIG. 9, shaft 608 has a length "L". In some embodiments, length "L" can be selected to limit the extent by which the temperature of solution 604 changes (e.g., decreases) in traveling from vessel 602 to nozzle 610. In certain embodiments, length "L" can be at most about 12 inches (e.g., at most about 10 inches, at most about eight inches, at most about six inches, at most about four inches, at most about two inches, at most about one inch, at most about 0.5 inch) and/or at least about 0.1 inch (e.g., at least about 0.5 inch, at least about one inch, at least about two inches, at least about four inches, at least about six inches, at least about eight inches, at least about 10 inches).

Figure 10:
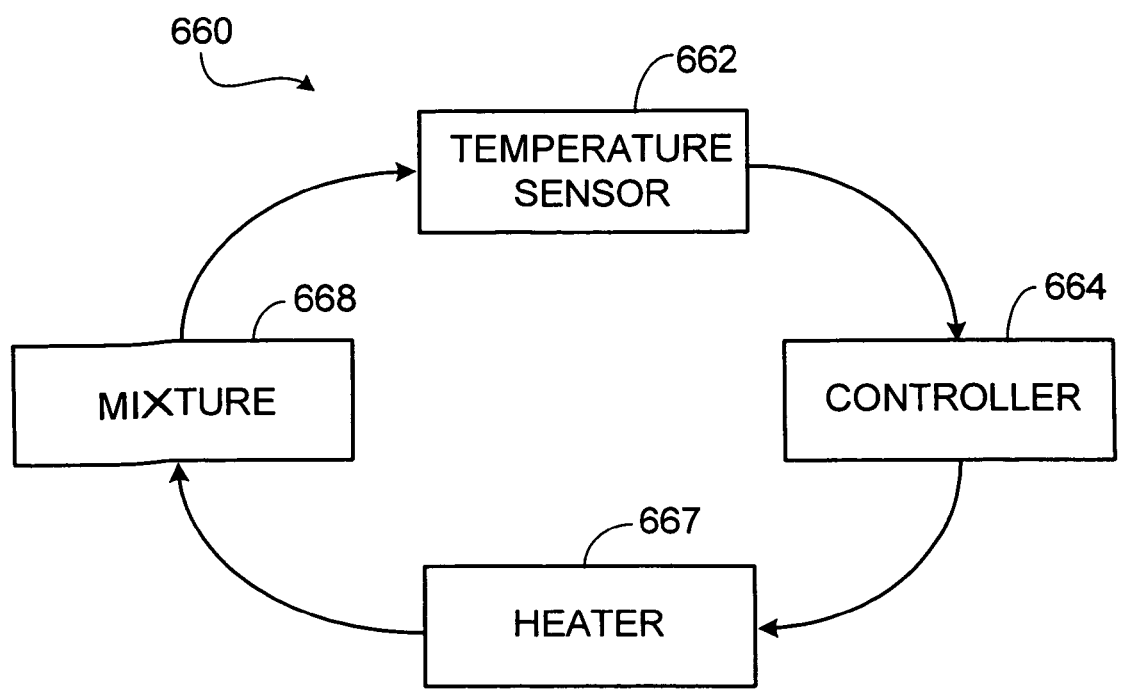
FIG. 10 is a schematic of a feedback loop.

In certain embodiments, a temperature sensor can be a part of a feedback loop. For example, FIG. 10 shows a feedback loop 660 including a temperature sensor 662, a controller 664, a heater 667, and a mixture 668. Temperature sensor 662 provides information about the temperature of mixture 668 to controller 664, which then activates or deactivates heater 667 accordingly. For example, if the temperature of mixture 668 is too low, then controller 664 can activate heater 667, which can heat mixture 668 to the desired temperature.

In certain embodiments, the viscosity of a mixture can be regulated by monitoring and/or regulating the temperature of the mixture. Typically, the viscosity of a mixture can decrease as the temperature of the mixture increases. In some embodiments, the viscosity of a mixture used in a drop formation process (such as a solution containing a polymer and a gelling precursor) can be at least about 60 centipoise (e.g., at least about 70 centipoise, at least about 80 centipoise, at least about 90 centipoise) and/or at most about 100 centipoise (e.g., at most about 90 centipoise, at most about 80 centipoise, at most about 70 centipoise).

Figure 11:
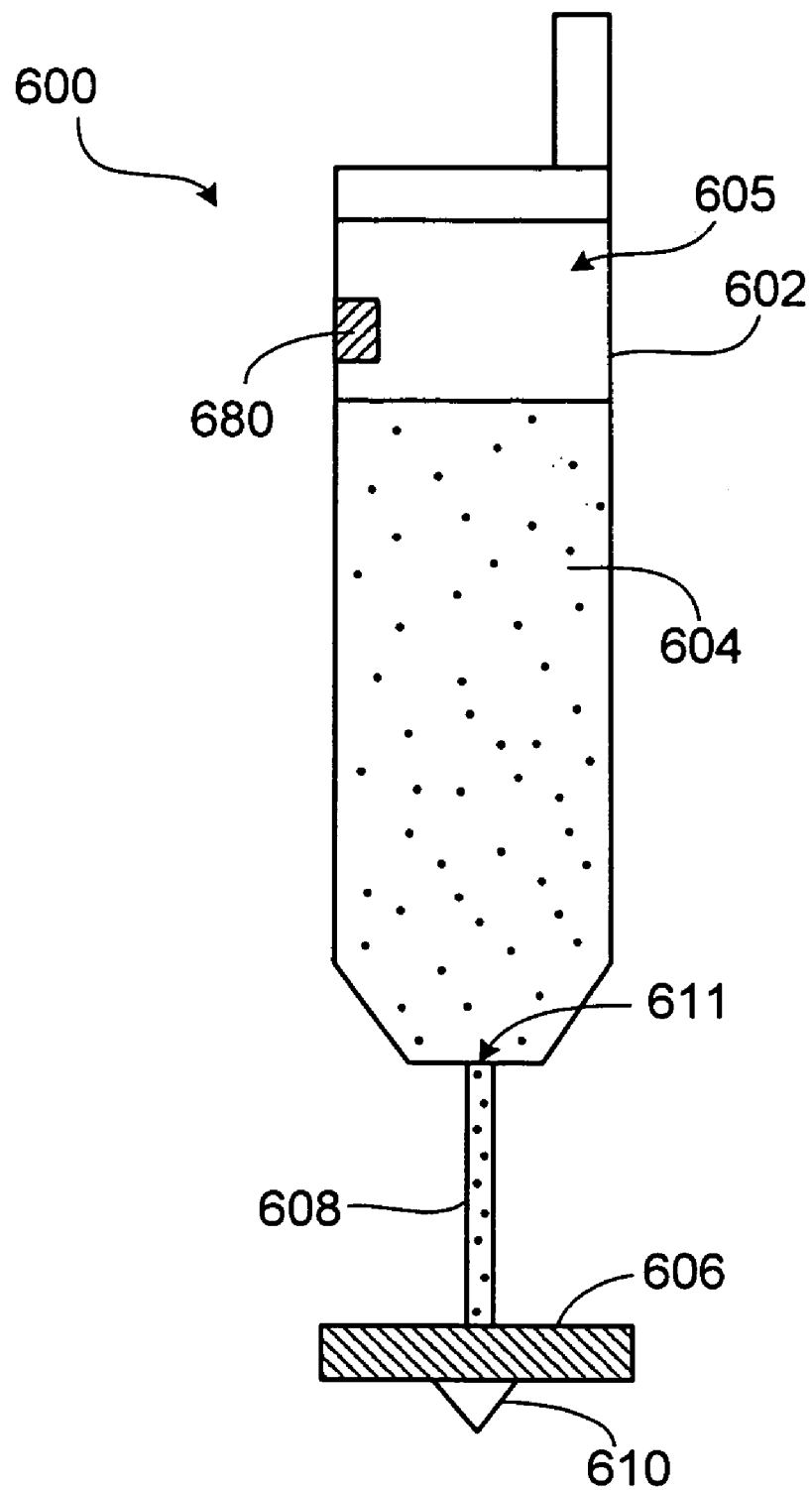
FIG. 11 is a side view of an embodiment of an apparatus for manufacturing particles.

In some embodiments, the pressure within a drop generator can be monitored and/or regulated. For example, as shown in FIG. 11, a pressure sensor 680 (e.g., a strain gauge, a piezoelectric element) is located within vessel 602 of drop generator 600. Pressure sensor 680 is in contact with gas 605, and thus can be used to measure the pressure of gas 605.

Figure 12:
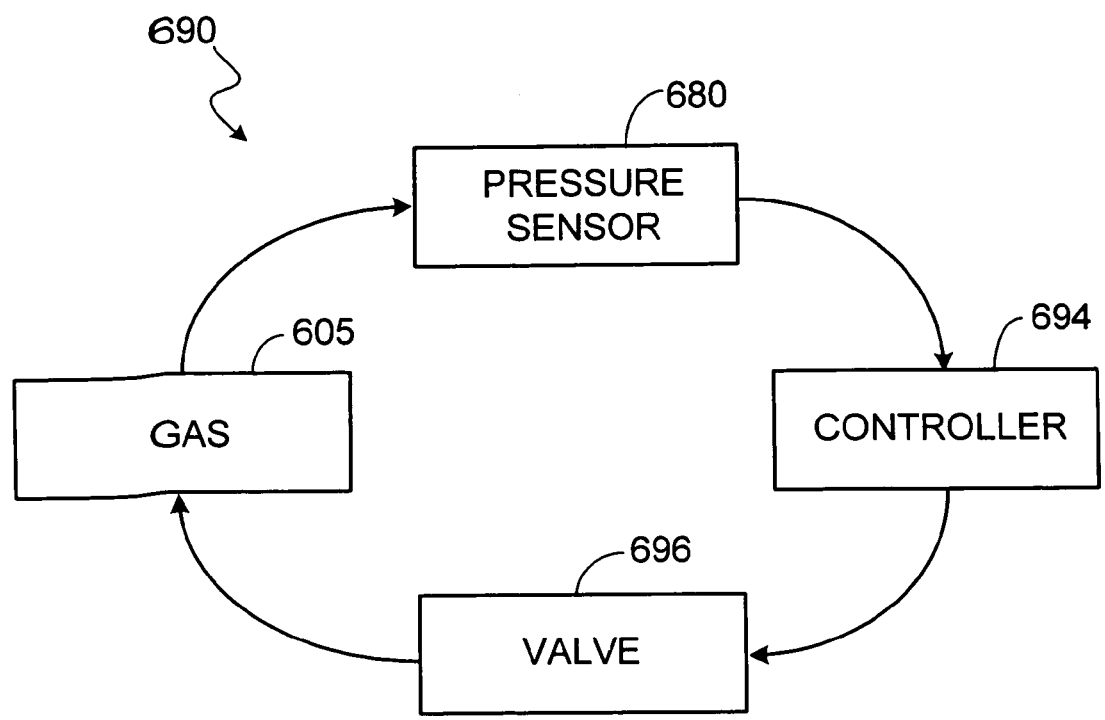
FIG. 12 is a schematic of a feedback loop.

In certain embodiments, a pressure sensor can be a part of a feedback loop. For example, FIG. 12 shows a feedback loop 690 including pressure sensor 680, a controller 694, a valve 696, and gas 605. Valve 696 can be located, for example, in area 611 (FIG. 11) of drop generator 600, so that valve 696 can be used to control the release of solution 604 through nozzle 610. Pressure sensor 680 can provide information to controller 694 about the pressure of gas 605, so that controller 694 can control valve 696 accordingly. For example, if the pressure of gas 605 too high, then controller 694 can cause valve 696 to open, thereby releasing some of solution 604 from vessel 602 and causing the pressure of gas 605 to decrease.

In some embodiments, a drop generator vessel can be supplied by an external source. The external source may be releasably attached to the drop generator so that the external source can be detached from the drop generator and cleaned, refilled, and/or replaced.

Figure 13:
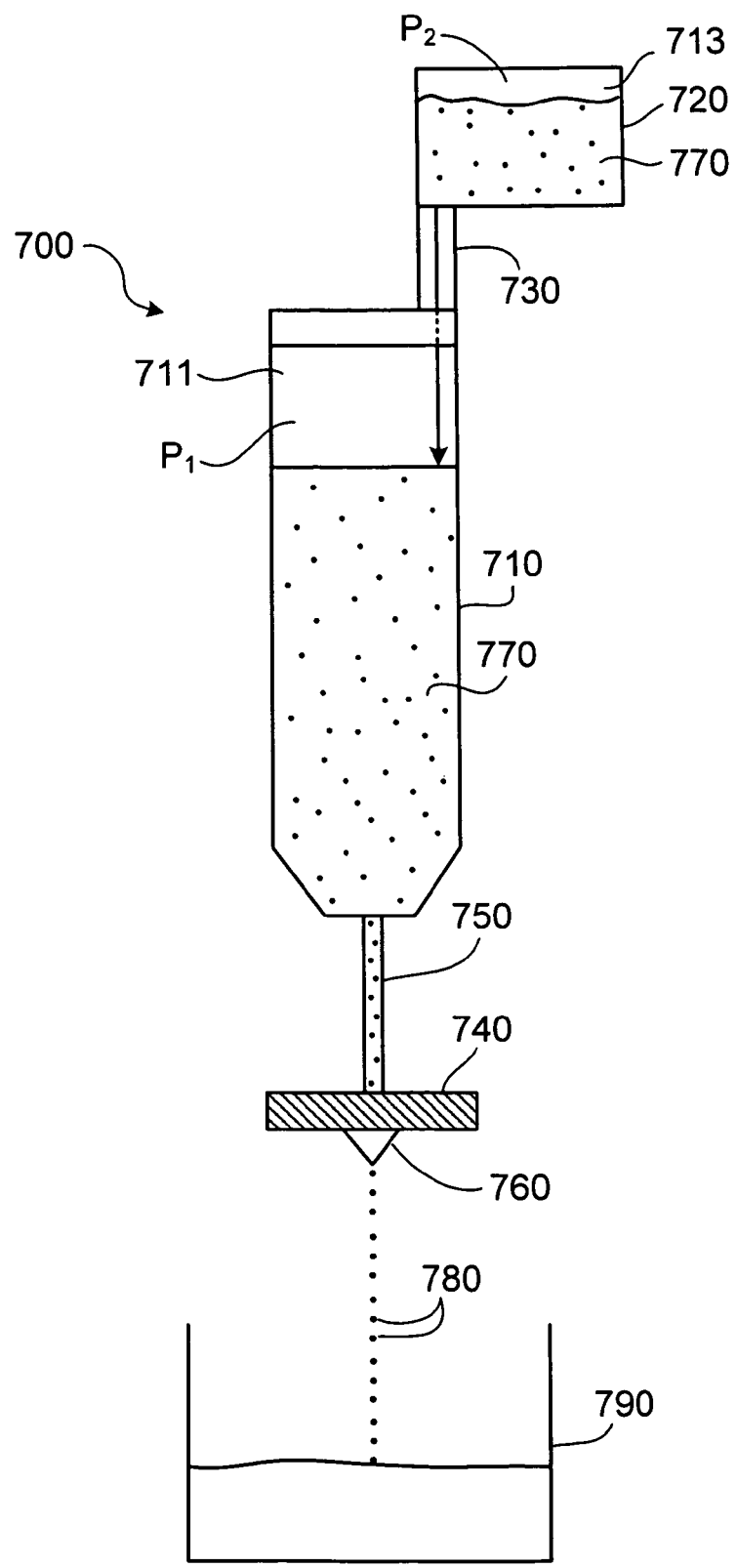
FIG. 13 is a side view of an embodiment of a process for manufacturing particles.

As an example, FIG. 13 shows a drop generation apparatus 700 including a vessel 710, a source 720 connected to vessel 710 by a shaft 730, a vibrating membrane 740 connected to vessel 710 by a shaft 750, and a nozzle 760. Vessel 710 and source 720 both contain a solution 770.

As shown in FIG. 13, during use of drop generation apparatus 700, solution 770 flows from vessel 710 through shaft 750 and contacts vibrating membrane 740, forming drops 780 that fall into a vessel 790. As the level of solution 770 in vessel 710 decreases, the pressure $P_1$ of a gas 711 in vessel 710 also decreases. A gas 713 in source 720 has a pressure $P_2$. During use of drop generation apparatus 700, the difference between $P_2$ and $P_1$ increases. Eventually, this difference can become high enough to cause solution 770 from source 720 to flow into vessel 710 via shaft 730. Thus, source 720 can be used to replenish vessel 790 with solution 770.

In certain embodiments, solution 770 can flow from source 720 into vessel 710 when the difference between $P_2$ and $P_1$ is at least about 0.125 psi (e.g., at least about 0.2 psi, at least about 0.25 psi, at least about 0.3 psi, at least about 0.4 psi, at least about 0.5 psi, at least about 0.6 psi, at least about 0.8 psi, at least about one psi, at least about two psi, at least about five psi, at least about seven psi, at least about 10 psi, at least about 15 psi, at least about 20 psi, at least about 25 psi), and/or at most about 30 psi (e.g., at most about 25 psi, at most about 20 psi, at most about 15 psi, at most about 10 psi, at most about seven psi, at most about five psi, at most about two psi, at most about one psi, at most about 0.8 psi, at most about 0.6 psi, at most about 0.5 psi, at most about 0.4 psi, at most about 0.3 psi, at most about 0.25 psi, at most about 0.2 psi). In some embodiments, solution 770 can flow from source 720 into vessel 710 when the difference between $P_2$ and $P_1$ is from about 7.25 psi to about 26.5 psi.

In some embodiments, an operator can determine when to allow solution 770 from source 720 to flow into vessel 710. For example, if the difference between $P_2$ and $P_1$ reaches a certain level, the operator can open a valve in shaft 730 to allow solution 770 to flow from source 720 into vessel 710.

In some embodiments, source 720 may be an integral part of drop generation apparatus 700. In certain embodiments, source 720 can be releasably attached (e.g., locked) to shaft 730 and/or shaft 730 can be releasably attached (e.g., locked) to vessel 710. In some such embodiments, source 720 can be detached from vessel 710 such that, for example, source 720 can be changed, cleaned, and/or refilled. In certain embodiments, source 720 can be detached from vessel 710 and replaced with another source. The use of an integral or detachable source of solution can allow vessel 710 to have a relatively constant supply of solution during a drop generation process, can allow the source to be exchanged with another source, and/or can allow the solution in the source to be changed.

In certain embodiments, shaft 730 can be flexible. This can, for example, allow shaft 730 to be moved when detaching and/or attaching source 720.

In some embodiments, a filter can be located between source 720 and vessel 710 (e.g., in shaft 730). In certain embodiments, the filter can be used to filter debris or other material from solution 770 before solution 770 enters vessel 710.

The flow of solution through a drop generator can be laminar or non-laminar. One type of non-laminar flow is turbulent flow. In some embodiments, the flow of solution through a drop generator can be helical. In general, helical flow can be laminar or non-laminar (e.g., turbulent).

FIGS. 14A and 14B show a drop generator 800 including a vessel 810 containing a solution 820, a shaft 830, a vibrating membrane 840, and a nozzle 850. Shaft 830 contains a membrane 835. As solution 820 flows out of vessel 810, it flows through membrane 835, which causes solution 820 to follow a flow path 860 within shaft 830. As solution 820 flows through shaft 830 and vibrating membrane 840, drops 870 form, which then fall into a vessel 880. In certain embodiments, drops 870 may be substantially spherical. In some embodiments, non-laminar (e.g., turbulent) and/or helical flow can limit stagnation of solution 820 as solution 820 travels through shaft 830, and/or can en In certain embodiments, solution 820 can have a flow rate of at least about one milliliter per minute (e.g., at least about two milliliters per minute, at least about five milliliters per minute, at least about 10 milliliters per minute) and/or at most about 12 milliliters per minute (e.g., at most about 10 milliliters per minute, at most about five milliliters per minute, at most about two milliliters per minute).

Figure 14C:
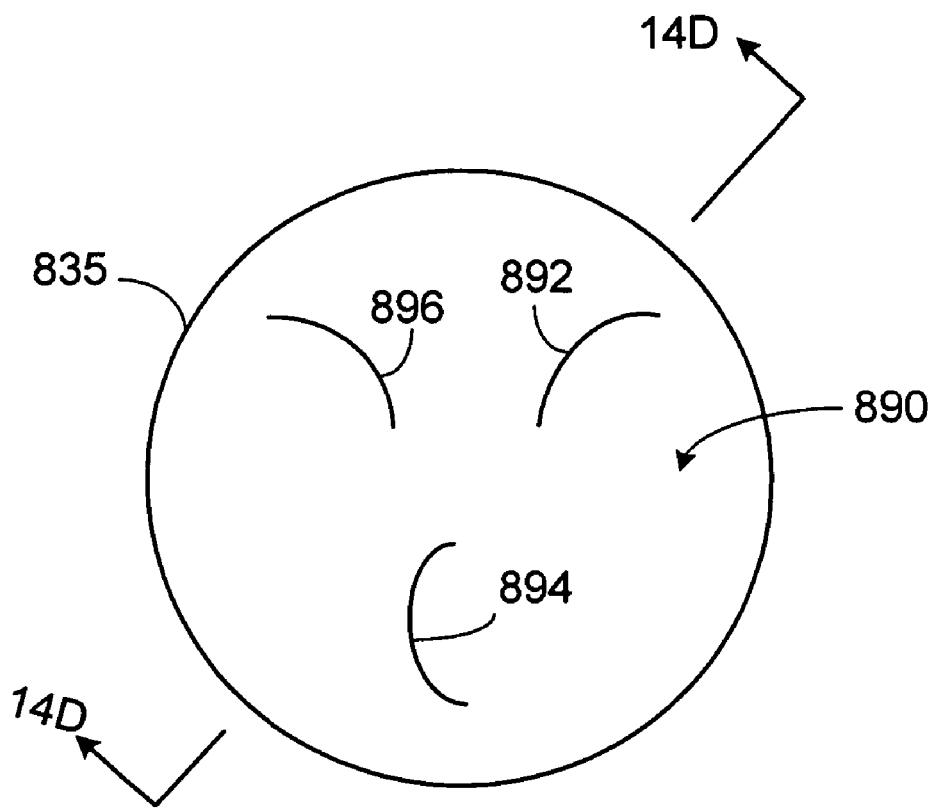
FIG. 14C is a top view of an embodiment of a membrane.
Figure 14D:
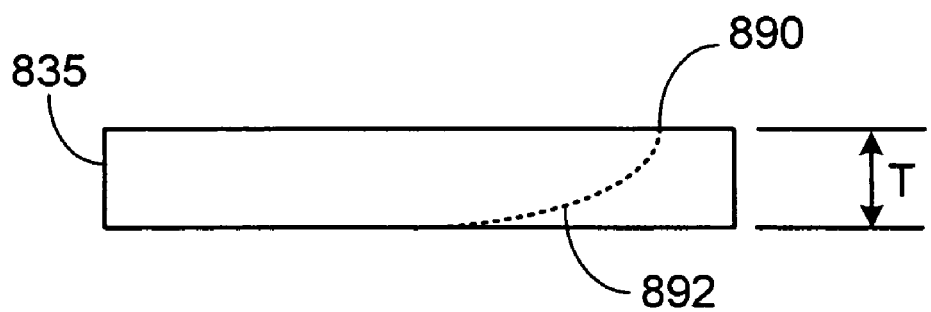
FIG. 14D is a side cross-sectional view of the membrane of FIG. 14C, taken along line 14D-14D.

FIGS. 14C and 14D show membrane 835, which has a structure that causes solution 820 to follow flow path 860 within shaft 830. Membrane 835 has a surface plane 890 and three curved slits 892, 894, and 896 in surface plane 890. Slits 892, 894, and 896 also have a curvature through the thickness "T" of membrane 835, as shown (for slit 892) in FIG. 14D. In some embodiments, thickness "T" can be at least about 0.04 inch (e.g., at least about 0.06 inch, at least about 0.08 inch, at least about 0.1 inch, at least about 0.15 inch) and/or at most about 0.2 inch (e.g., at most about 0.15 inch, at most about 0.1 inch, at most about 0.08 inch, at most about 0.06 inch). In certain embodiments, thickness "T" can be 0.0625 inch.

Helical flow, which can be laminar or non-laminar, is described, for example, in U.S. patent application Ser. No. 10/768,855, filed on Jan. 29, 2004, and entitled "Pressure Actuated Safety Valve With Spiral Flow Membrane", which is incorporated herein by reference. PCT Application Publication No. WO 02/062271 A1, published on Aug. 15, 2002, and entitled "Valve", discloses, for example, a heart valve with a configuration that allows blood to assume a helical flow path after flowing through the valve, which can reduce or eliminate turbulence and/or dead flow regions in the blood flow. PCT Application Publication No. WO 00/32241, published on Jun. 8, 2000, and entitled "Stents for Blood Vessels", discloses a stent that can be used to support part of a blood vessel and that can be used to cause flow within the vessel to assume a swirling pattern to mimic a flow pattern that can normally be found in arteries.

Figure 15:
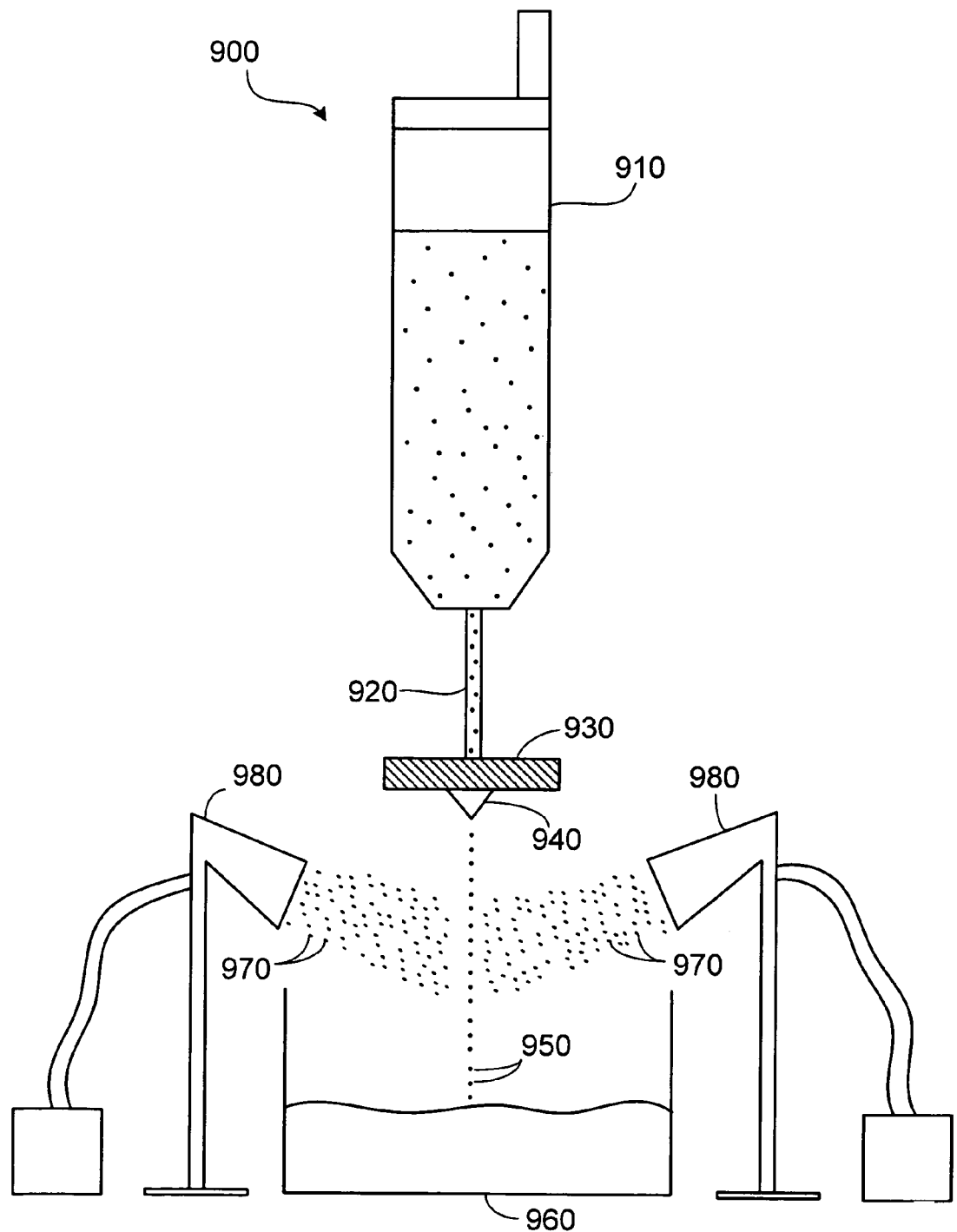
FIG. 15 is a side view of an embodiment of a process for manufacturing particles.

In some embodiments, sprayers (e.g., atomizers) can be used in a drop generation process. For example, FIG. 15 shows a drop generator 900 including a vessel 910, a shaft 920, a vibrating membrane 930, and a nozzle 940. Drop generator 900 forms drops 950 that fall into a vessel 960. As drops 950 are falling, they are sprayed with a material 970 using sprayers 980.

Material 970 can be, for example, a therapeutic agent, a gelling agent, a polymer, a gelling precursor, and/or a cross-linking agent. In some embodiments, drops 950 can include a polymer, and material 970 can be a cross-linking agent that cross-links the polymer in drops 950 as drops 950 fall. In certain embodiments, material 970 can be a porosity-enhancing agent, such as starch, sodium chloride, or calcium chloride. Porosity-enhancing agents can increase the number and/or sizes of pores in particles. In some embodiments, material 970 can be the same material (e.g., a polymer) out of which drops 950 are formed. In certain embodiments, material 970 and drops 950 can be formed of different materials (e.g., different polymers).

In some embodiments, more than one material can be sprayed onto drops 950 as drops 950 fall. As an example, one of sprayers 980 can spray one material onto drops 950, and another of sprayers 980 can spray another material onto drops 950. As another example, sprayers 980 can spray a mixture of multiple (e.g., two, three) different materials onto drops 950. In some embodiments, as material 970 is sprayed onto drops 950, material 970 can form a coating on drops 950.

In certain embodiments, drops 950 can include a polymer, and sprayers 980 can spray a polymer onto drops 950. The polymer included in drops 950 can be the same as, or different from, the polymer sprayed onto drops 950 by sprayers 980.

Figure 16:
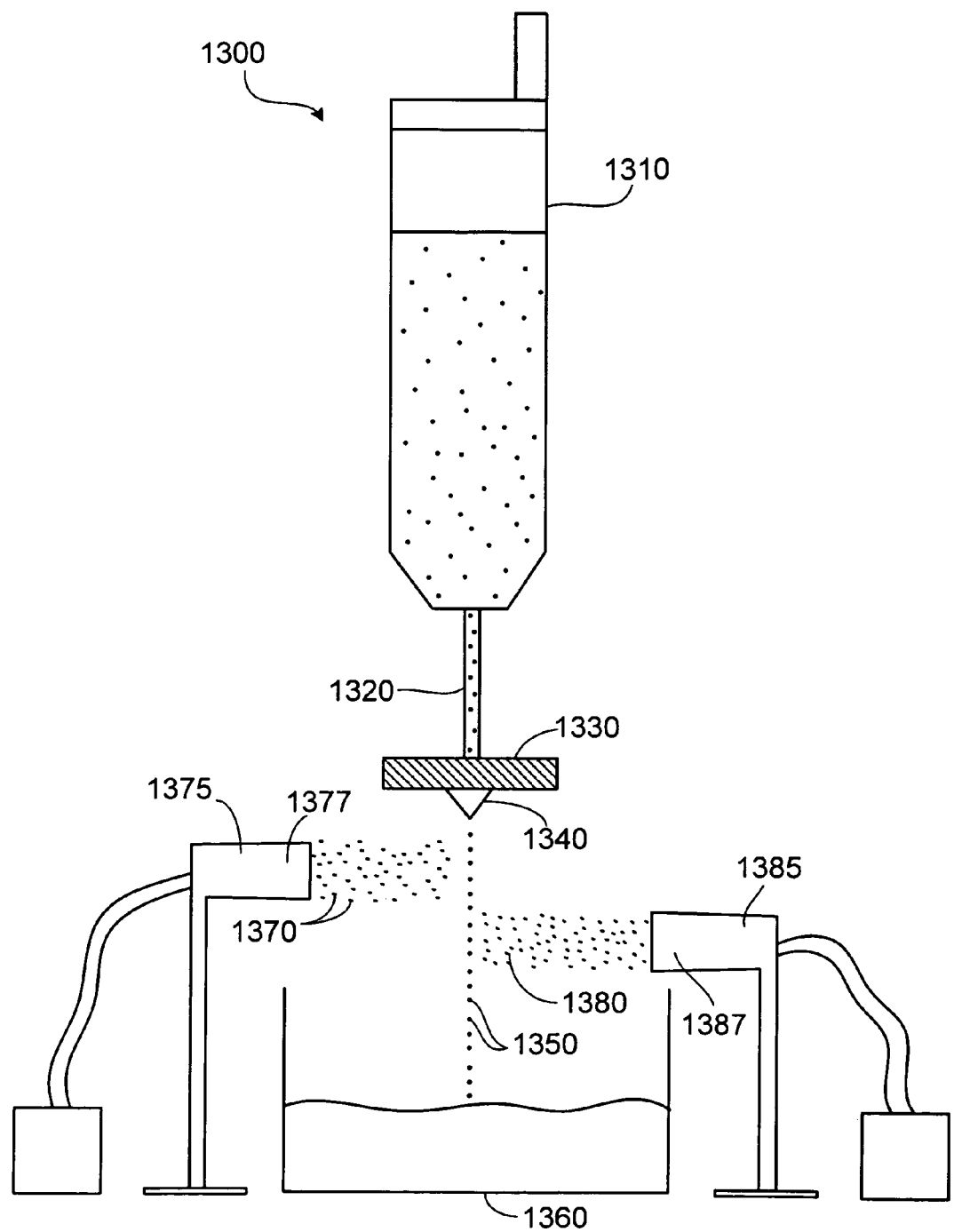
FIG. 16 is a side view of an embodiment of a process for manufacturing particles.

While sprayers 980 are shown in FIG. 15 as being at approximately the same level, in some embodiments, sprayers can be located at different levels. For example, FIG. 16 shows a drop generator 1300 including a vessel 1310, a shaft 1320, a vibrating membrane 1330, and a nozzle 1340. Drop generator 1300 forms drops 1350 that fall into a vessel 1360. As drops 1350 are falling, they are sprayed with a material 1370 using a sprayer 1375, and with a material 1380 using a sprayer 1385. The head 1377 of sprayer 1375 is located at a higher level than the head 1387 of sprayer 1385. Materials 1370 and 1380 may be the same as, or different from, each other.

Figure 17:
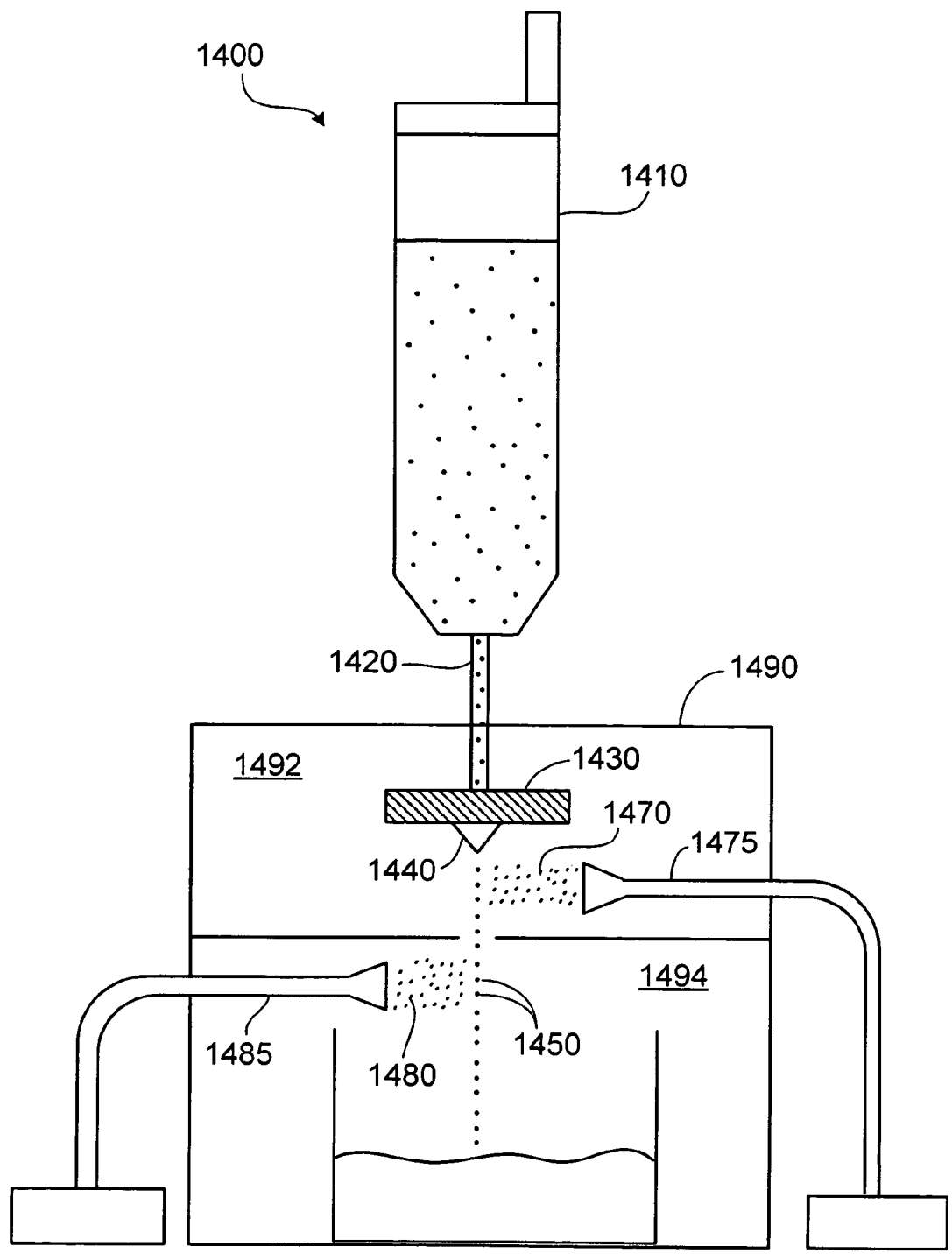
FIG. 17 is a side view of an embodiment of a process for manufacturing particles.

In certain embodiments, sprayers can be separated from each other. For example, FIG. 17 shows a drop generator 1400 including a vessel 1410, a shaft 1420, a vibrating membrane 1430, and a nozzle 1440. Drop generator 1400 forms drops 1450 that fall into a vessel 1460. As drops 1450 are falling, they are sprayed first with a material 1470 (e.g., a gelling agent) using a sprayer 1475, and then with a material 1480 (e.g., a therapeutic agent) using a sprayer 1485. Materials 1470 and 1480 may be the same as, or different from, each other. The area in which drops 1450 fall is enclosed by a housing 1490 including two spaces 1492 and 1494. Sprayer 1475 sprays drops 1450 as drops 1450 fall through space 1492, and sprayer 1485 sprays drops 1450 as drops 1450 fall through space 1494. In some embodiments, segregating sprayer 1475 from sprayer 1485 may limit the amount of interaction between material 1470 and material 1480.

While spraying has been described, in some embodiments other methods can be used to apply one or more materials to drops. Examples of other methods include sputtering (e.g., physical vapor deposition). As an example, in certain embodiments, drops can be generated in a sputter chamber so that one or more materials can be added to the drops via sputtering during and/or after generation of the drops.

Figure 18:
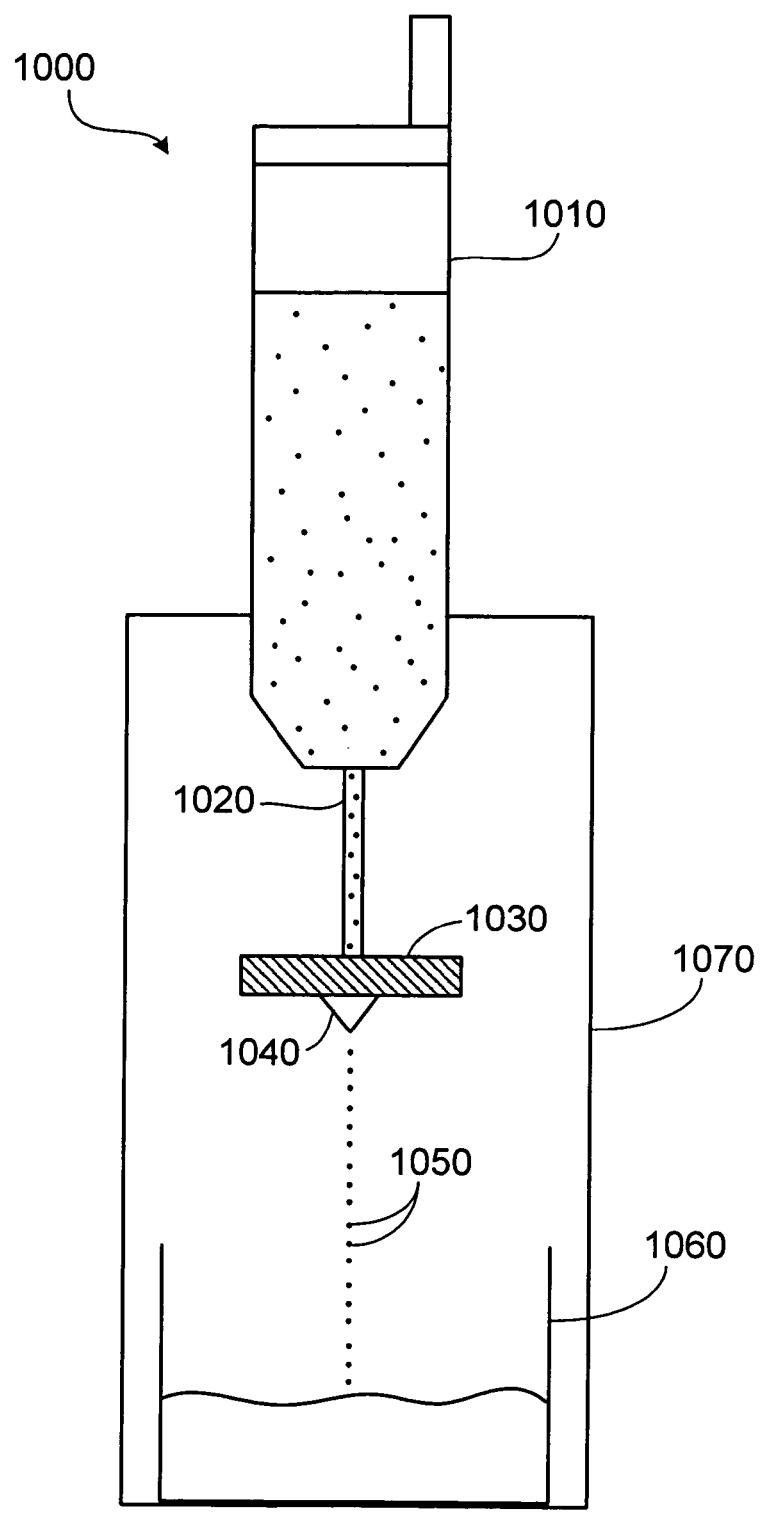
FIG. 18 is a side view of an embodiment of a process for manufacturing particles.

In certain embodiments, the drops can be exposed to a controlled environment during the drop generation process. For example, FIG. 18 shows a drop generator 1000 including a vessel 1010, a shaft 1020, a vibrating membrane 1030, and a nozzle 1040. Drop generator 1000 forms drops 1050 that fall into a vessel 1060. A housing 1070 encloses a portion of drop generator 1000 and all of vessel 1060. Housing 1070 provides a controlled environment for drop generation by drop generator 1000.

As an example, in some embodiments, housing 1070 can be used to provide a relatively humid environment for drop generation. In certain embodiments, the relative humidity of the atmosphere within housing 1070 can be at least about 20 percent (e.g., at least about 30 percent, at least about 40 percent, at least about 50 percent, at least about 60 percent, at least about 70 percent, at least about 75 percent, at least about 80 percent, at least about 85 percent, at least about 90 percent, at least about 95 percent), and/or at most about 100 percent (e.g., at most about 95 percent, at most about 90 percent, at most about 85 percent, at most about 80 percent, at most about 75 percent, at most about 70 percent, at most about 60 percent, at most about 50 percent, at most about 40 percent, at most about 30 percent). In some embodiments, drops 1050 can be sprayed with one or more materials as drops 1050 fall from drop generator 1000 (e.g., as described above with reference to FIGS. 15-17). The relatively high relative humidity provided within housing 1070 can cause the material(s) to adhere more easily to drops 1050 than they might otherwise. For example, in some embodiments, a relatively high relative humidity may help a hydrophilic material to adhere to the drops as the drops are formed.

As another example, in certain embodiments, housing 1070 can be used to provide a drop generation environment having a relatively low humidity. In some embodiments, the drop generation environment can have a humidity of at most about 40 percent (e.g., at most about 35 percent, at most about 30 percent, at most about 25 percent, at most about 20 percent, at most about 15 percent, at most about 10 percent), and/or at least about five percent (e.g., at least about 10 percent, at least about 15 percent, at least about 20 percent, at least about 25 percent, at least about 30 percent, at least about 35 percent). For example, in certain embodiments in which drops including one or more bioerodible materials (such as those described below) are generated, the drop generation environment may have a relatively low relative humidity. The relatively low humidity of the drop generation environment may limit or prevent premature erosion by the bioerodible material(s). In some embodiments in which drops including one or more therapeutic agents (such as those described below) are generated, the drop generation environment may have relatively low relative humidity which can, for example, limit or prevent dilution of the therapeutic agent(s).

In some embodiments, housing 1070 can be used to provide a drop generation environment that includes one or more gases, such as oxygen and/or nitrogen. In certain embodiments, housing 1070 can be used to provide a drop generation environment that includes one or more inert gases, such as argon. In some embodiments, a drop generation environment that includes one or more inert gases may be relatively unlikely to react with one or more of the materials that are being used to form the drops.

In certain embodiments, housing 1070 can be used to provide a drop generation atmosphere that has a pressure of greater than one atmosphere. In certain embodiments, housing 1070 can be used to provide an atmosphere having a pressure of at least about 1.1 atmospheres (e.g., at least about 1.2 atmospheres, at least about 1.3 atmospheres, at least about 1.4 atmospheres, at least about 1.5 atmospheres, at least about two atmospheres, at least about 2.5 atmospheres, at least about three atmospheres), and/or at most about five atmospheres (e.g., at most about three atmospheres, at most about 2.5 atmospheres, at most about two atmospheres, at most about 1.5 atmospheres, at most about 1.4 atmospheres, at most about 1.3 atmospheres, at most about 1.2 atmospheres). Without wishing to be bound by theory, it is believed that as the pressure of a drop generation atmosphere increases, the size of the drops that form may decrease.

Figure 19:
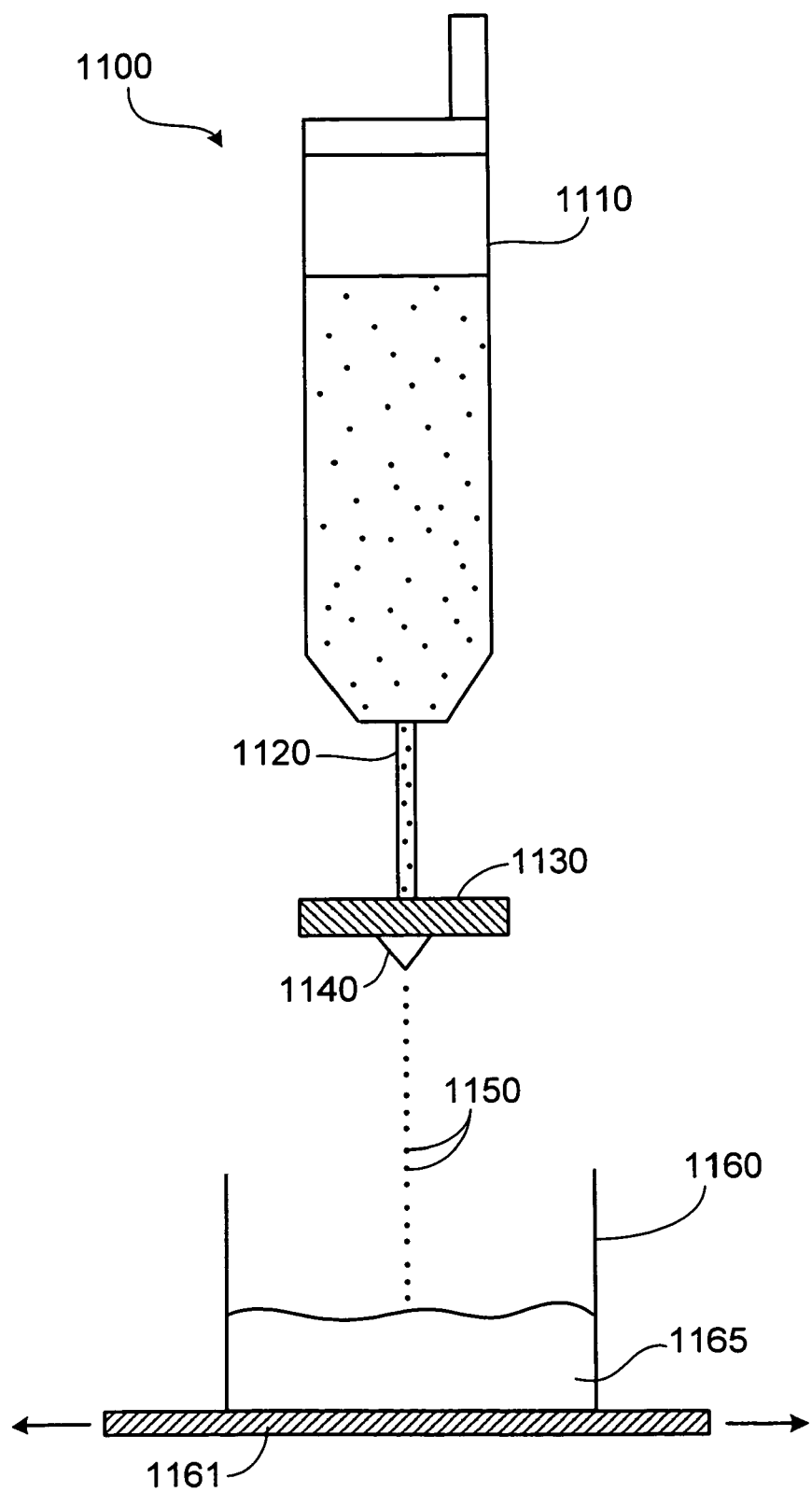
FIG. 19 is a side view of an embodiment of a process for manufacturing particles.

In some embodiments, drops that are formed by a drop generator may fall into a moving vessel. For example, FIG. 19 shows a drop generator 1100 including a vessel 1110, a shaft 1120, a vibrating membrane 1130, and a nozzle 1140. Drop generator 1100 forms drops 1150 that fall into a vibrating vessel 1160 containing a solution 1165. Vessel 1160 is made to vibrate by being situated on a vibrating pad 1161. The vibration of vessel 1160 can cause solution 1165 to move which can, for example, provide enhanced uniformity and/or decreased stagnation of solution 1165, and/or lead to a more uniform distribution of drops 1150 in solution 1165.

While vessel 1160 is shown as vibrating, in certain embodiments, vessel 1160 can move in other ways. For example, in some embodiments, vessel 1160 can be disposed on a turntable that causes vessel 1160 to rotate, thereby making solution 1165 circulate. Alternatively or additionally, a mixture (e.g., a solution) contained within a vessel can be made to circulate using a magnetic stirrer. In some embodiments, a mixture contained within a vessel can be made to circulate using a pump (e.g., a pump including one or more filters), such as a Fluval circulation pump or a VWR Immersion Circulator (from PolyScience).

In some embodiments, multiple vessels or multiple cavities within a vessel can be used to collect drops that form during a drop generation process.

Figure 20A:
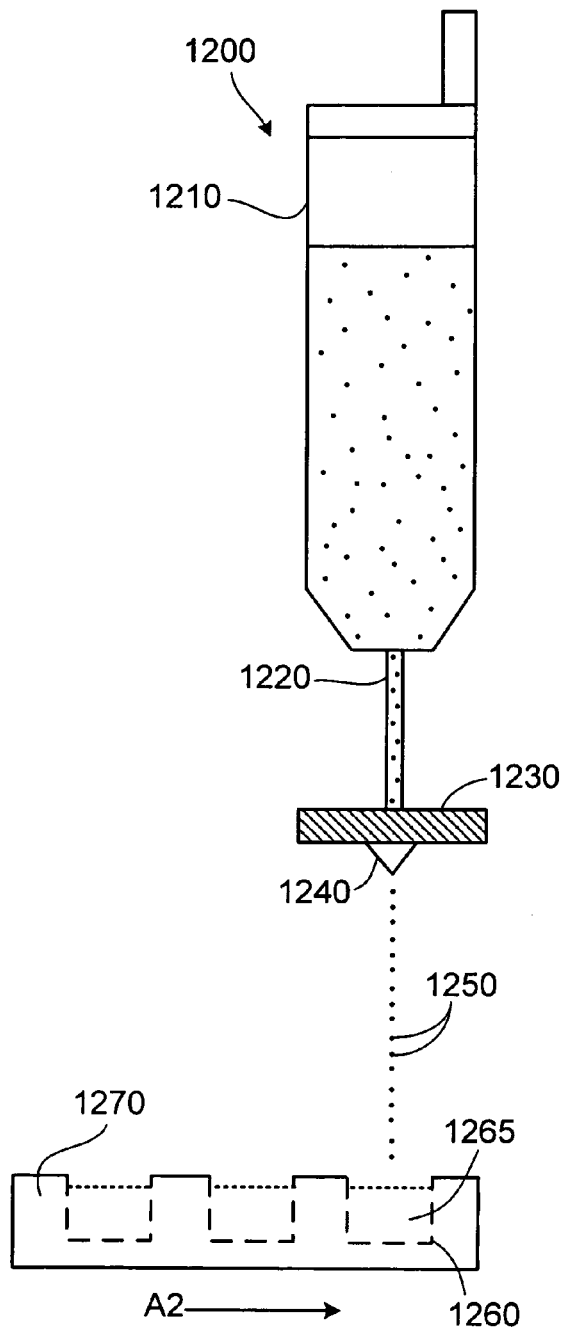
FIGS. 20A and 20B are side views of an embodiment of a process for manufacturing particles.
Figure 20B:
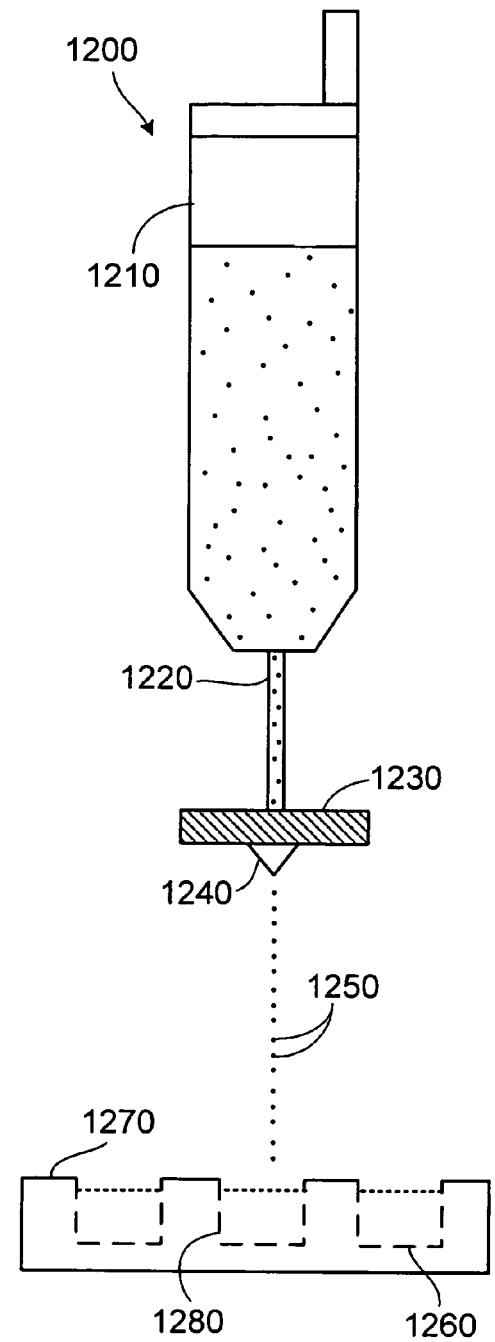

For example, FIG. 20A shows a drop generator 1200 including a vessel 1210, a shaft 1220, a vibrating membrane 1230, and a nozzle 1240. Drop generator 1200 forms drops 1250 that fall into a solution 1265 contained in a cavity 1260 in a block 1270. After a certain period of time has passed, block 1270 shifts in the direction of arrow A2, such that, as shown in FIG. 20B, drops 1250 now fall into a different cavity 1280 in block 1270.

Collecting drops in different cavities can allow different groupings of drops to be collected in different cavities during one drop generation process, without the drop generation process being stopped. For example, in certain embodiments, differently shaped and/or sized drops can be collected in different cavities. As an example, spherical drops may be collected in one cavity, while cylindrical drops are collected in another cavity. In some embodiments, drops that are formed of different materials can be collected in different cavities. In certain embodiments, the collection of drops in different cavities can allow for a more uniform amount of reaction of the drops (e.g., if the drops contain a gelling precursor and the cavities contain a gelling agent). For example, drops can be collected in a cavity over a relatively short time period (e.g., 30 seconds), and then can be allowed to react in the cavity while another cavity is used to collect additional drops that are being generated. In some embodiments, collecting drops in a cavity over a relatively short time period can allow the drops all to be reacted (e.g., cross-linked, gelled) over a similar amount of time, such that the drops can all be relatively uniform in composition.

Drops and/or particles that are formed using one of the processes described herein can have any of a number of different sizes and/or shapes. In general, a drop and/or particle can have a diameter of at most about 3,000 microns (e.g., from about two microns to about 3,000 microns, from about 10 microns to about 3,000 microns, from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns). In some embodiments, a drop and/or particle can have a diameter of at most about 3,000 microns (e.g., at most about 2,500 microns; at most about 2,000 microns; at most about 1,500 microns; at most about 1,200 microns; at most about 1,000 microns; at most about 900 microns; at most about 700 microns; at most about 500 microns; at most about 400 microns; at most about 300 microns; at most about 100 microns), and/or at least about two microns (e.g., at least about 10 microns, at least about 100 microns; at least about 300 microns; at least about 400 microns; at least about 500 microns; at least about 700 microns; at least about 900 microns; at least about 1,000 microns; at least about 1,200 microns; at least about 1,500 microns; at least about 2,000 microns; at least about 2,500 microns).

In certain embodiments, a plurality of drops and/or particles can have an arithmetic mean diameter of at most about 3,000 microns (e.g., at most about 2,500 microns; at most about 2,000 microns; at most about 1,500 microns; at most about 1,200 microns; at most about 900 microns; at most about 700 microns; at most about 500 microns; at most about 400 microns; at most about 300 microns; at most about 100 microns), and/or at least about 10 microns (e.g., at least about 100 microns; at least about 300 microns; at least about 400 microns; at least about 500 microns; at least about 700 microns; at least about 900 microns; at least about 1,200 microns; at least about 1,500 microns; at least about 2,000 microns; at least about 2,500 microns). Exemplary ranges for the arithmetic mean diameter of drops and/or particles (e.g., particles delivered to a subject) include from about 100 microns to about 500 microns; from about 100 microns to about 300 microns; from about 300 microns to about 500 microns; from about 500 microns to about 700 microns; and from about 900 microns to about 1,200 microns. In general, the particles delivered to a subject in a composition can have an arithmetic mean diameter in approximately the middle of the range of the diameters of the individual particles, and a variance of at most about 20 percent (e.g., at most about 15 percent, at most about 10 percent).

The arithmetic mean diameter of a group of drops and/or particles can be determined using a Beckman Coulter Rapid-VUE Image Analyzer version 2.06 (Beckman Coulter, Miami, Fla.), described above. The arithmetic mean diameter of a group of drops and/or particles (e.g., in a composition) can be determined by dividing the sum of the diameters of all of the drops and/or particles in the group by the number of drops and/or particles in the group.

In some embodiments, multiple particles can be combined with a carrier fluid (e.g., a pharmaceutically acceptable carrier, such as a saline solution, a contrast agent, or both) to form an embolic composition. In general, the density of the particles (e.g., as measured in grams of material per unit volume) is such that they can be readily suspended in the carrier fluid and remain suspended during delivery. In some embodiments, the density of a particle is from about 1.1 grams per cubic centimeter to about 1.4 grams per cubic centimeter. As an example, for suspension in a saline-contrast solution, the density can be from about 1.2 grams per cubic centimeter to about 1.3 grams per cubic centimeter.

Embolic compositions can be used in, for example, neural, pulmonary, and/or AAA (abdominal aortic aneurysm) applications. The compositions can be used in the treatment of, for example, fibroids, tumors, internal bleeding, arteriovenous malformations (AVMs), and/or hypervascular tumors. The compositions can be used as, for example, fillers for aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the subject, or the amount sufficient to prophylactically treat a subject. The embolic compositions can be administered as pharmaceutically acceptable compositions to a subject in any therapeutically acceptable dosage, including those administered to a subject intravenously, subcutaneously, percutaneously, intratrachealy, intramuscularly, intramucosaly, intracutaneously, intra-articularly, orally or parenterally.

An embolic composition can include a mixture of particles (e.g., particles that include different types of therapeutic agents), or can include particles that are all of the same type. In some embodiments, an embolic composition can be prepared with a calibrated concentration of particles for ease of delivery by a physician. A physician can select an embolic composition of a particular concentration based on, for example, the type of embolization procedure to be performed. In certain embodiments, a physician can use an embolic composition with a relatively high concentration of particles during one part of an embolization procedure, and an embolic composition with a relatively low concentration of particles during another part of the embolization procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about ten minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

Figure 21B:
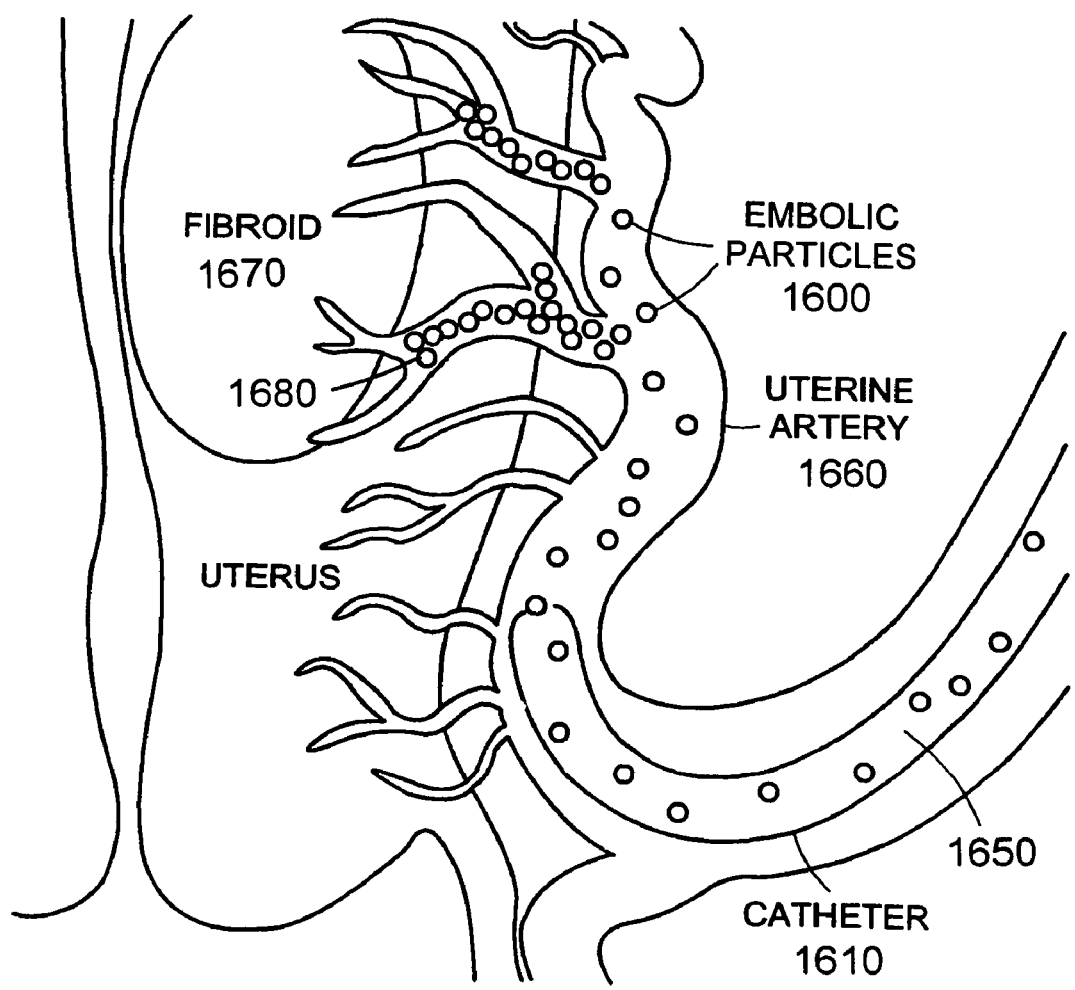
FIG. 21B is an enlarged view of region 21B in FIG. 21A.

FIGS. 21A and 21B show an embolization procedure in which an embolic composition including embolic particles 1600 and a carrier fluid is injected into a vessel through an instrument such as a catheter 1610. Catheter 1610 is connected to a syringe barrel 1620 with a plunger 1630. The embolic composition is loaded into syringe barrel 1620, and catheter 1610 is inserted, for example, into a femoral artery 1640 of a patient. Plunger 1630 of syringe barrel 1620 is then compressed to deliver the embolic composition through catheter 1610 into a lumen 1650 of a uterine artery 1660 that leads to a fibroid 1670 located in the uterus of the patient. The embolic composition can, for example, occlude uterine artery 1660.

As shown in FIG. 21B, uterine artery 1660 is subdivided into smaller uterine vessels 1680 (e.g., having a diameter of about two millimeters or less) which feed fibroid 1670. Particles 1600 in the embolic composition partially or totally fill the lumen of uterine artery 1660, either partially or completely occluding the lumen of the uterine artery 1660 that feeds uterine fibroid 1670.

In some embodiments, among the particles delivered to a subject in an embolic composition, the majority (e.g., about 50 percent or more, about 60 percent or more, about 70 percent or more, about 80 percent or more, about 90 percent or more) of the particles can have a diameter of about 3,000 microns or less (e.g., about 2,500 microns or less; about 2,000 microns or less; about 1,500 microns or less; about 1,200 microns or less; about 900 microns or less; about 700 microns or less; about 500 microns or less; about 400 microns or less; about 300 microns or less; about 100 microns or less) and/or about ten microns or more (e.g., about 100 microns or more; about 300 microns or more; about 400 microns or more; about 500 microns or more; about 700 microns or more; about 900 microns or more; about 1,200 microns or more; about 1,500 microns or more; about 2,000 microns or more; about 2,500 microns or more).

In some embodiments, the arithmetic mean diameter of the particles delivered to a subject in an embolic composition can vary depending upon the particular condition to be treated. As an example, in embodiments in which the particles in an embolic composition are used to treat a liver tumor, the particles delivered to the subject can have an arithmetic mean diameter of about 500 microns or less (e.g., from about 100 microns to about 300 microns; from about 300 microns to about 500 microns). As another example, in embodiments in which the particles in an embolic composition are used to treat a uterine fibroid, the particles delivered to the subject in an embolic composition can have an arithmetic mean diameter of about 1,200 microns or less (e.g., from about 500 microns to about 700 microns; from about 700 microns to about 900 microns; from about 900 microns to about 1,200 microns).

Particles can have any of a number of different shapes. For example, particles can be conical, diamond-shaped, spheroidal, or cylindrical. In certain embodiments, particles can be substantially spherical. In some embodiments, a particle can have a sphericity of about 0.8 or more (e.g., about 0.85 or more, about 0.9 or more, about 0.95 or more, about 0.97 or more).

In some embodiments, the sphericity of a particle after compression in a catheter (e.g., after compression to about 50 percent or more of the cross-sectional area of the particle) can be about 0.8 or more (e.g., about 0.85 or more, about 0.9 or more, about 0.95 or more, about 0.97 or more). The particle can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more).

The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as $Da/Dp$ (where $Da=\sqrt{(4A/\pi)}$; $Dp=P/\pi$; $A$=pixel area; $P$=pixel perimeter), is a value from zero to one, with one representing a perfect circle.

In some embodiments, a particle can be substantially non-spherical. In certain embodiments, a particle can be mechanically shaped during or after the particle formation process to be nonspherical (e.g., ellipsoidal). In some embodiments, a particle can be shaped (e.g., molded, compressed, punched, and/or agglomerated with other particles) at different points in the particle manufacturing process. As an example, in certain embodiments in which a particle is formed using a gelling agent, the particle can be physically deformed into a specific shape and/or size after the particle has been contacted with the gelling agent, but before the polymer(s) in the particle have been cross-linked. After shaping, the polymer(s) (e.g., polyvinyl alcohol) in the particles can be cross-linked, optionally followed by substantial removal of gelling precursor (e.g., alginate). In some embodiments, a nonspherical particle can be formed by post-processing the particle (e.g., by cutting or dicing into other shapes). Particle shaping is described, for example, in Baldwin et al., U.S. Published Patent Application No. US 2003/0203985 A1, which is incorporated herein by reference.

Particles can include any of a number of different materials. For example, particles may include one or more polymers and/or gelling precursors.

Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides (e.g., nylon), polyureas, polyurethanes, polyesters, polyethers, polystyrenes, polysaccharides (e.g., alginate, agarose), polylactic acids, polyethylenes, polymethylmethacrylates, polyethylacrylate, polycaprolactones, polyglycolic acids, poly(lactic-co-glycolic) acids (e.g., poly(d-lactic-co-glycolic) acids), and copolymers or mixtures thereof. In certain embodiments, the polymer can be a highly water insoluble, high molecular weight polymer. An example of such a polymer is a high molecular weight polyvinyl alcohol (PVA) that has been acetalized. The polymer can be substantially pure intrachain 1,3-acetalized PVA and substantially free of animal derived residue such as collagen.

Examples of gelling precursors include alginates, alginate salts (e.g. sodium alginate), xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. A preferred sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel.

As described above, in some embodiments, particles can be formed by contacting drops with one or more gelling agents and/or cross-linking agents.

Examples of gelling agents include divalent cations such as alkali metal salts, alkaline earth metal salts or transition metal salts that can ionically cross-link with a gelling precursor. In some embodiments, an inorganic salt, such as a calcium, barium, zinc or magnesium salt, can be used as a gelling agent. In certain embodiments (e.g., embodiments in which a gelling precursor is alginate), a suitable gelling agent is calcium chloride. The calcium cations have an affinity for carboxylic groups in the gelling precursor. The cations complex with carboxylic groups in the gelling precursor, resulting in encapsulation of the base polymer in a matrix of gelling precursor.

Examples of cross-linking agents include aldehydes (e.g., formaldehyde, glyoxal, benzaldehyde, aterephthalaldehyde, succinaldehyde, glutaraldehyde). In some embodiments in which a polyvinyl alcohol solution is used to generate drops, one or more aldehydes can be used to react the polyvinyl alcohol by acetilizing the polyvinyl alcohol. In certain embodiments, one or more acids can be used in conjunction with a cross-linking agent, to react with drops and form particles. Examples of acids include strong acids (e.g., sulfuric acid, hydrochloric acid, nitric acid) and weak acids (e.g., acetic acid, formic acid, phosphoric acid).

In some embodiments, a particle can include one or more therapeutic agents (e.g., drugs). The therapeutic agent can, for example, be encapsulated within a particle so that when the particle bursts, it releases the therapeutic agent (e.g., to a target site). Alternatively or additionally, in an embodiment of a particle including a coating, the coating can include one or more therapeutic agents (e.g., thrombogenic agents). In some embodiments, a particle can have a coating that includes a high concentration of one or more therapeutic agents. One or more of the therapeutic agents can also be loaded into the interior region of a particle. Thus, the surface of the particle can release an initial dosage of therapeutic agent after which the body of the particle can provide a burst release of therapeutic agent. The therapeutic agent on the surface of the particle can be the same as or different from the therapeutic agent in the body of the particle. The therapeutic agent on the surface can be applied by exposing the particle to a high concentration solution of the therapeutic agent. The therapeutic agent coated particle can include another coating over the surface the therapeutic agent (e.g., a degradable and/or bioabsorbable polymer which erodes when the particle is administered). The coating can assist in controlling the rate at which therapeutic agent is released from the particle. For example, the coating can be in the form of a porous membrane. The coating can delay an initial burst of therapeutic agent release. The coating can be applied by dipping or spraying the particle. The coating can include therapeutic agent or can be substantially free of therapeutic agent. The therapeutic agent in the coating can be the same as or different from an agent on a surface layer of the particle and/or within the particle. A polymer coating (e.g. an erodible coating) can be applied to the particle surface in embodiments in which a high concentration of therapeutic agent has not been applied to the particle surface. Coatings are described, for example, in U.S. Patent Application Publication No. US 2004/0076582 A1, published on Apr. 22, 2004, and entitled "Agent Delivery Particle", which is incorporated herein by reference.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death (e.g., anti-apoptotic Bcl-2 family factors and Akt kinase).

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

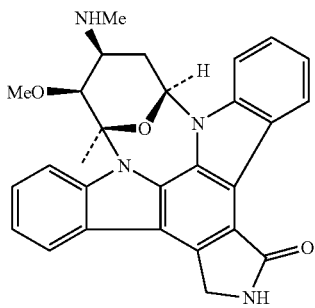

as well as diindoloalkaloids having one of the following general structures:

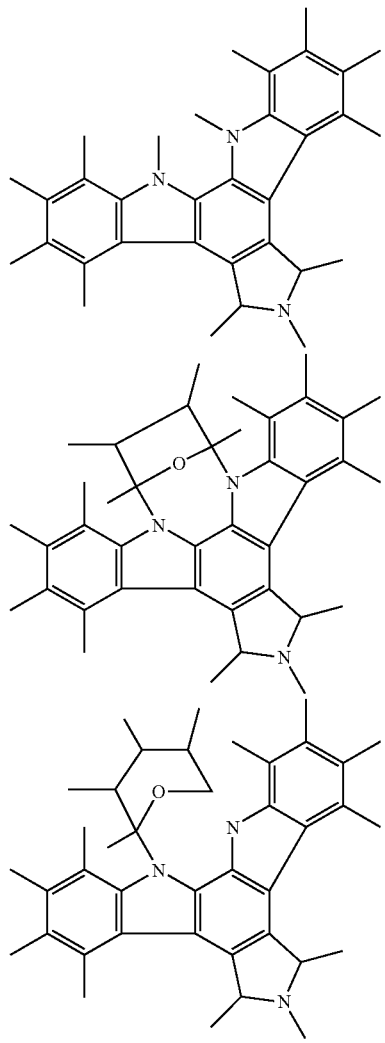

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nor-dihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, antisense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in co-pending U.S. Patent Application Publication No. US 2004/0076582 A1, published on Apr. 22, 2004, and entitled "Agent Delivery Particle", in Pinchuk et al., U.S. Pat. No. 6,545,097, and in Schwarz et al., U.S. Pat. No. 6,368,658, all of which are incorporated herein by reference.

In some embodiments, a particle can include a shape memory material, which is capable of being configured to remember (e.g., to change to) a predetermined configuration or shape. In certain embodiments, a particle that includes a shape memory material can be selectively transitioned from a first state to a second state. For example, a heating device provided in the interior of a delivery catheter can be used to cause a particle including a shape memory material to transition from a first state to a second state. Shape memory materials and particles that include shape memory materials are described in, for example, U.S. Patent Application Publication No. US 2004/0091543 A1, published on May 13, 2004, and entitled "Embolic Compositions", and U.S. patent application Ser. No. 10/791,103, filed Mar. 2, 2004, and entitled "Embolic Compositions", both of which are incorporated herein by reference.

In certain embodiments, a particle can include a surface preferential material. Surface preferential materials are described, for example, in U.S. patent application Ser. No. 10/791,552, filed on Mar. 2, 2004, and entitled "Embolization", which is incorporated herein by reference.

In some embodiments, a particle can include one or more bioerodible and/or bioabsorbable materials. Examples of bioerodible and/or bioabsorbable materials include polysaccharides (e.g., alginate); polysaccharide derivatives; inorganic, ionic salts; water soluble polymers (e.g., polyvinyl alcohol, such as polyvinyl alcohol that has not been cross-linked); biodegradable poly DL-lactide-poly ethylene glycol (PELA); hydrogels (e.g., polyacrylic acid, hyaluronic acid, gelatin, carboxymethyl cellulose); polyethylene glycol (PEG); chitosan; polyesters (e.g., polycaprolactones); poly(lactic-co-glycolic) acid (e.g., a poly(d-lactic-co-glycolic) acid); and combinations thereof. In some embodiments, a particle can include sodium alginate.

In certain embodiments, a particle can include one or more diagnostic agents (e.g., a radiopaque material, a material that is visible by magnetic resonance imaging (an MRI-visible material), an ultrasound contrast agent). In some embodiments, a particle can include one or more ferromagnetic materials. In some embodiments, a diagnostic agent and/or ferromagnetic material can be added to a particle by, e.g., injection of the diagnostic agent and/or ferromagnetic material into the particle and/or by soaking the particle in the diagnostic agent and/or ferromagnetic material. Diagnostic agents and ferromagnetic materials are described in U.S. Patent Application Publication No. US 2004/0101564 A1, published on May 27, 2004, and entitled "Embolization", which is incorporated herein by reference.

While certain embodiments have been described, other embodiments are possible.

As an example, in some embodiments, multiple variations on a drop generation process can be used together. For example, in certain embodiments, a non-laminar stream of a mixture flowing through a drop generator can be exposed to a non-uniform membrane vibration frequency. In some embodiments, a non-laminar stream of a mixture flowing through a drop generator can be exposed to a non-square or non-rectangular membrane vibration waveform.

As another example, while a dual-channel frequency generator has been described, in certain embodiments, a drop generator can include a frequency generator having more than two (e.g., three, four, five) channels.

As an additional example, in some embodiments, drops can contact both a gelling agent and a cross-linking agent at the same time. In certain embodiments, the gelling agent and the cross-linking agent can be combined together in a mixture (e.g., a mixture that is contained in a vessel). In some embodiments, drops can fall into a vessel containing a gelling agent, which can cause the drops to gel. After the drops have gelled, the gelling agent can be removed (e.g., drained) from the vessel and the cross-linking agent can be added into the vessel.

Figure 22:
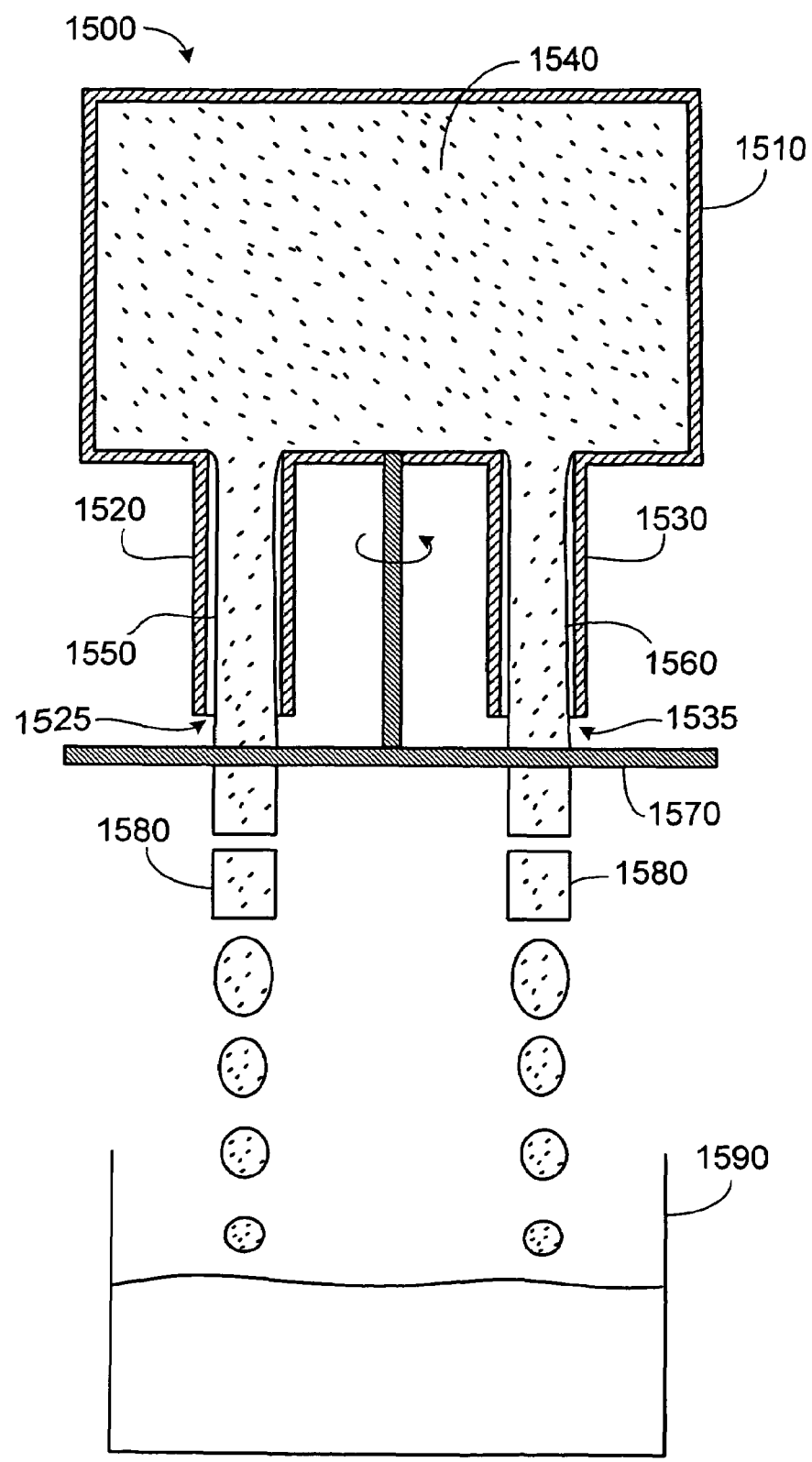
FIG. 22 is a side view of an embodiment of a process for manufacturing particles.

As a further example, while examples of certain drop generators have been described, in some embodiments, drops can be generated using other types of drop generators. In certain embodiments, drops can be generated by a drop generator that employs a cutting mechanism. For example, FIG. 22 shows a drop generator 1500 that includes a vessel 1510 and shafts 1520 and 1530. Vessel 1510 contains a solution 1540. Solution 1540 travels through shafts 1520 and 1530, forming streams 1550 and 1560 that exit through orifices 1525 and 1535 in shafts 1520 and 1530. Shortly after streams 1550 and 1560 exit the orifices, they are cut by a rotating cutter 1570, which forms cylindrical drops 1580 out of streams 1550 and 1560. As drops 1580 fall toward a vessel 1590 containing a gelling agent 1595, drops 1580 lose their cylindrical shape and gradually turn spheroidal and then substantially spherical. In some embodiments, vessel 1590 can be located closer to shafts 1520 and 1530, such that drops 1580 can be captured while they still are in their cylindrical or spheroidal shape. An example of a commercially available drop generator that uses a cutting mechanism to form drops is the Genialab® JetCutter Type S (from Genialab).

While a drop generator with a cutting mechanism, a vessel, and two shafts has been shown, in some embodiments, the drop generator may include only one shaft or may include more than two shafts (e.g., three shafts, four shafts, five shafts). In certain embodiments, a drop generator may include more than one vessel (e.g., two vessels, three vessels). In some embodiments, a drop generator may use a cutting mechanism that does not include a rotating cutter. As an example, a drop generator may use a cutting mechanism that includes a gas pulse (e.g., an air knife).

As an additional example, in some embodiments, the flow rate of a stream of material (e.g., a stream of solution that is used to form drops) can be measured using, for example, a flowmeter. In certain embodiments, the flow rate of a stream of material can be measured to determine whether the viscosity of the stream is increasing or decreasing.

As another example, while the use of sprayers to apply a cross-linking agent to drops has been described, in some embodiments, drops can be cross-linked using other methods, either in addition to, or as an alternative to, using a cross-linking agent. For example, in certain embodiments, drops can be cross-linked by applying a laser, ultraviolet radiation, and/or heat to the drops.

As a further example, in some embodiments, a gas (e.g., air, nitrogen, argon, krypton, helium, neon) can be bubbled through a mixture or solution (e.g., a gelling agent solution) contained in a gelling vessel. In certain embodiments, bubbling a gas through a mixture can reduce the surface tension of the mixture.

As an additional example, in certain embodiments, a mixture or solution in a gelling vessel (e.g., a gelling agent solution) can be heated to a temperature greater than room temperature, such as a temperature of about 30° C. or more (e.g., about 40° C. or more, about 50° C. or more, about 60° C. or more, about 70° C. or more, about 80° C. or more, about 90° C. or more). For example, in some embodiments, a gelling agent mixture or solution can be heated to a temperature of about 80° C. In certain embodiments, heating a gelling agent mixture or solution can reduce the surface tension of the mixture or solution and/or can result in the formation of particles that are substantially spherical.

As a further example, in some embodiments, particles having different shapes, sizes, physical properties, and/or chemical properties, can be used together in an embolization procedure. The different particles can be delivered into the body of a subject in a predetermined sequence or simultaneously. In certain embodiments, mixtures of different particles can be delivered using a multi-lumen catheter and/or syringe. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in U.S. Patent Application Publication No. US 2004/0091543 A1, published on May 13, 2004, and entitled "Embolic Compositions", and in U.S. patent application Ser. No. 10/791,103, filed on Mar. 2, 2004, and entitled "Embolic Compositions", both of which are incorporated herein by reference.

As an additional example, in some embodiments particles can be used for tissue bulking. As an example, particles can be placed (e.g., injected) into tissue adjacent to a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in co-pending U.S. Patent Application Publication No. US 2003/0233150 A1, published on Dec. 18, 2003, and entitled "Tissue Treatment", which is incorporated herein by reference.

Figure 23:
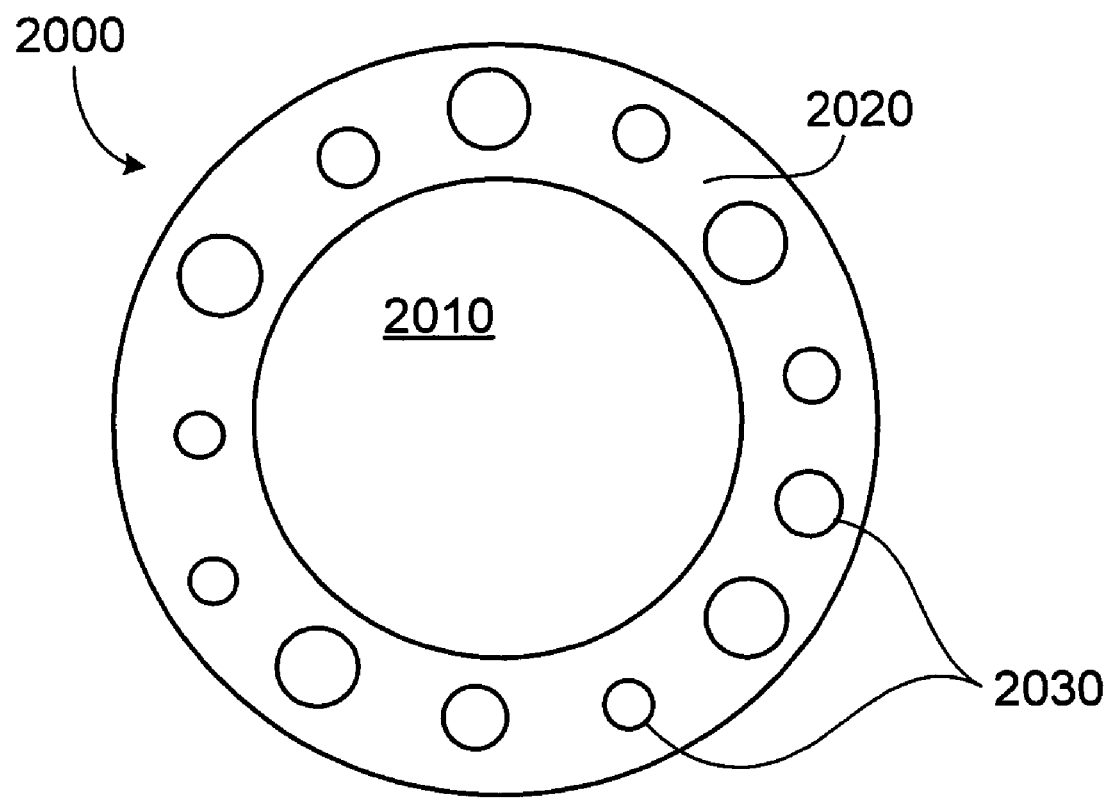
FIG. 23 is a side cross-sectional view of an embodiment of a particle.

As a further example, in some embodiments, a particle (either porous or non-porous) can include at least one cavity (a hollow central region in the particle). In certain embodiments in which a particle includes a cavity, the particle can further include pores in the material surrounding the cavity. For example, FIG. 23 shows a particle 2000 with a cavity 2010 surrounded by a matrix material 2020 (e.g., a polymer) that includes pores 2030.

As another example, in some embodiments a particle can be porous and/or can include one or more cavities. In certain embodiments, the particle can have a substantially uniform pore structure. In some embodiments, the particle can have a non-uniform pore structure. For example, the particle can have a substantially non-porous interior region (e.g., formed of a polyvinyl alcohol) and a porous exterior region (e.g., formed of a mixture of a polyvinyl alcohol and alginate). Porous particles are described in U.S. Published Patent Application No. US 2004/0096662 A1, published on May 20, 2004, which is incorporated herein by reference.

As an additional example, in certain embodiments, particles can be linked together to form particle chains. For example, the particles can be connected to each other by links that are formed of one or more of the same material(s) as the particles, or of one or more different material(s) from the particles. Particle chains and methods of making particle chains are described, for example, in U.S. patent application Ser. No. 10/830,195, filed on Apr. 22, 2004, and entitled "Embolization", which is incorporated herein by reference.

As another example, while embodiments of drop generators including a vibrating membrane have been disclosed, in some embodiments, the drop generators can additionally or alternatively include a cutting mechanism. Furthermore, while embodiments of drop generators including a cutting mechanism have been disclosed, in some embodiments, the drop generators can additionally or alternatively include a vibrating membrane.

As a further example, while vibrating membranes have been disclosed, in some embodiments, one or more other devices can be used to generate a periodic disturbance of a stream of a mixture. For example, in certain embodiments, one or more piezoelectric elements may be used.

As an additional example, in some embodiments, drops can be rinsed (e.g., with water) after the drops have contacted a gelling agent. For example, in certain embodiments, drops including a gelling precursor can fall into a vessel containing a gelling agent (e.g., calcium chloride). After the gelling agent has caused the gelling precursor in the drops to gel, the gelled drops can be removed from the vessel and rinsed (e.g., with water) to remove extra gelling agent that may be on the drops.

As another example, in certain embodiments, a non-uniform membrane vibration frequency may be used to generate drops of different shapes. For example, FIG. 24A shows a drop generator 2200 forming a conical drop 2210, a cylindrical drop 2220, and a spherical drop 2230. Drop generator 2200 includes a membrane that is vibrating at a frequency represented by a membrane vibration waveform 2240, shown in FIG. 24B.

As a further example, in some embodiments, a gas (e.g., air, nitrogen, argon, krypton, helium, neon) can be bubbled through a gelling agent mixture in a vessel. In certain embodiments, an air pump (e.g., an Accuculture air pump) can be used to pump air into a gelling agent mixture. Without wishing to be bound by theory, it is believed that in some embodiments, bubbling a gas through a gelling agent mixture may reduce the surface tension of the mixture and/or result in the formation of relatively small particles (e.g., particles having a diameter of less than about 500 microns).

As an additional example, in some embodiments, one or more mirrors may be used to observe a drop generation process. In certain embodiments, the mirror(s) may be used in combination with one or more other observation devices.

As another example, in certain embodiments, coatings may be formed on drops by submerging the drops in a mixture (e.g., a solution) including the coating material.

Other embodiments are in the claims.

What is claimed is

1. A method comprising:
    forming a liquid stream of a mixture comprising a polymer and a gelling precursor;
    exposing the liquid stream to a vibration generated by a dual-channel frequency generator, the vibration having a waveform selected from the group consisting of triangular waveforms, and sawtooth waveforms to form a stream of non-spherical drops comprising the polymer and the gelling precursor;
    observing the stream of drops at a frequency generated by the dual-channel frequency generator, the frequency of observing being different from a frequency of the vibration, the difference between the frequency of observing and the frequency of the vibration being at most about 10 Hertz;
    contacting the stream of drops with a gelling agent to form first particles comprising a gel; and
    removing the gel from the first particles to provide second particles having pores.

2. The method of claim 1, wherein the waveform is a sawtooth waveform.

3. The method of claim 1, wherein the waveform is a triangular waveform.

4. The method of claim 1, wherein the liquid stream is laminar.

5. The method of claim 1, wherein the liquid stream is non-laminar.

6. The method of claim 1, wherein the second particles are conical.

7. The method of claim 1, wherein the second particles are diamond-shaped or spheroidal.

8. The method of claim 1, wherein the second particles are cylindrical.

9. The method of claim 1, wherein forming the liquid stream comprises forming the stream with a drop generator.

10. The method of claim 9, wherein the gelling agent is contained in a vessel, and a surface of the gelling agent is located at most about five inches below the drop generator.

11. The method of claim 1, wherein the method includes using a system comprising a temperature sensor or a pressure sensor.

12. A method, comprising:
    forming a stream of non-spherical drops at a first frequency using a dual-channel frequency generator, the stream of drops comprising a mixture of a polymer and a gelling precursor;
    observing the stream of drops at a second frequency generated by the dual-channel frequency generator;
    treating the stream of drops with a gelling agent to form first particles, wherein the first particles comprise a gel; and
    removing the gel from the first particles to provide second particles having pores.

13. The method of claim 12, wherein the second particles have an arithmetic mean diameter of at most about 3,000 microns.

14. The method of claim 12, wherein the dual-channel frequency generator has a first channel and a second channel, the first frequency is generated using the first channel, and the second frequency is generated using the second channel.

15. The method of claim 14, wherein the dual-channel frequency generator further comprises a third channel.

16. The method of claim 12, wherein observing the stream of drops at a second frequency comprises observing the stream of drops with a light.

17. The method of claim 16, wherein the light is a strobe light.

18. The method of claim 12, wherein observing the stream of drops at the second frequency comprises observing the stream of drops with a camera.

19. The method of claim 12, wherein observing the stream of drops comprises viewing the stream of drops using a combination of observation devices.

20. The method of claim 12, wherein the first frequency is at least about one Hertz.

21. The method of claim 12, wherein the first frequency is at most about 5,000 Hertz.

22. The method of claim 12, wherein the second frequency is at least about one Hertz.

23. The method of claim 12, wherein the second frequency is at most about 5,000 Hertz.

24. The method of claim 12, wherein the second frequency is about one Hertz.

25. The method of claim 12, wherein the method comprises forming the stream of drops at the first frequency and a third frequency.

26. The method of claim 12, wherein the method includes using a system comprising a temperature sensor or a pressure sensor.

* * * * *